US012600772B2

(12) United States Patent
Kato

(10) Patent No.: US 12,600,772 B2
(45) Date of Patent: Apr. 14, 2026

(54) THERAPEUTIC AGENT FOR ASTHMA CONTAINING IL-6 INHIBITOR

(71) Applicant: Motokazu Kato, Osaka (JP)

(72) Inventor: Motokazu Kato, Osaka (JP)

(73) Assignee: Motokazu Kato, Osaka (JP)

( * ) Notice: Subject to any disclaimer, the term of this patent is extended or adjusted under 35 U.S.C. 154(b) by 169 days.

(21) Appl. No.: 16/963,311

(22) PCT Filed: Jan. 31, 2019

(86) PCT No.: PCT/JP2019/003438
§ 371 (c)(1),
(2) Date: Jul. 20, 2020

(87) PCT Pub. No.: WO2019/151418
PCT Pub. Date: Aug. 8, 2019

(65) Prior Publication Data
US 2021/0363238 A1    Nov. 25, 2021

(30) Foreign Application Priority Data

Jan. 31, 2018    (JP) ................................. 2018-015983
Oct. 2, 2018    (JP) ................................. 2018-187251

(51) Int. Cl.
| | |
|---|---|
| A61K 39/00 | (2006.01) |
| A61K 9/00 | (2006.01) |
| A61K 38/00 | (2006.01) |
| A61K 39/395 | (2006.01) |
| A61K 45/06 | (2006.01) |
| A61P 11/00 | (2006.01) |
| C07K 16/00 | (2006.01) |
| C07K 16/24 | (2006.01) |
| C07K 16/28 | (2006.01) |

(52) U.S. Cl.
CPC .......... *C07K 16/248* (2013.01); *A61K 39/395* (2013.01); *A61K 45/06* (2013.01); *A61P 11/00* (2018.01); *C07K 16/2866* (2013.01)

(58) Field of Classification Search
None
See application file for complete search history.

(56) References Cited

U.S. PATENT DOCUMENTS

| | | | |
|---|---|---|---|
| 5,126,250 | A | 6/1992 | Mcdonough et al. |
| 5,216,128 | A | 6/1993 | Novick et al. |
| 5,530,101 | A | 6/1996 | Queen et al. |
| 5,621,077 | A | 4/1997 | Novick et al. |
| 5,639,455 | A | 6/1997 | Shimamura et al. |
| 5,670,373 | A | 9/1997 | Kishimoto |
| 5,795,965 | A | 8/1998 | Tsuchiya et al. |
| 5,817,790 | A | 10/1998 | Tsuchiya et al. |
| 5,856,135 | A | 1/1999 | Tsuchiya et al. |
| 5,888,510 | A | 3/1999 | Kishimoto et al. |
| 6,074,643 | A | 6/2000 | Barbera-Guillem |

| | | | |
|---|---|---|---|
| 6,121,423 | A | 9/2000 | Tsuchiya et al. |
| 6,261,560 | B1 | 7/2001 | Tsujinaka et al. |
| 6,309,636 | B1 | 10/2001 | do Couto et al. |
| 6,552,083 | B1 | 4/2003 | Isobe et al. |
| 6,723,319 | B1 | 4/2004 | Ito et al. |
| 7,291,721 | B2 | 11/2007 | Giles-Komar et al. |
| 7,320,792 | B2 | 1/2008 | Ito et al. |
| 7,414,024 | B2 | 8/2008 | Blay et al. |
| 7,438,907 | B2 | 10/2008 | Schuurman et al. |
| 7,479,543 | B2 | 1/2009 | Tsuchiya et al. |
| 7,521,052 | B2 | 4/2009 | Okuda et al. |
| 7,582,298 | B2 | 9/2009 | Stevens et al. |
| 7,759,472 | B2 | 7/2010 | Shima et al. |
| 7,781,617 | B2 | 8/2010 | Kudou et al. |
| 7,824,674 | B2 | 11/2010 | Ito et al. |
| 7,825,109 | B2 | 11/2010 | Nakade et al. |
| 7,884,196 | B2 | 2/2011 | Lawless |
| 7,935,340 | B2 | 5/2011 | Garcia-Martinez et al. |
| 7,955,590 | B2 | 6/2011 | Gillies et al. |
| 8,017,121 | B2 | 9/2011 | Kishimoto et al. |
| 8,226,611 | B2 | 7/2012 | Chen et al. |

(Continued)

FOREIGN PATENT DOCUMENTS

| | | |
|---|---|---|
| AR | 068564 A1 | 11/2009 |
| CA | 1332367 C | 10/1994 |

(Continued)

OTHER PUBLICATIONS

Kazuhiro et al. Real-world effects of two inhaled corticosteroid/long-acting β2-agonist combinations in the treatment of asthma. The Journal of asthma : official journal of the Association for the Care of Asthma, Abstract. vol. 51, No. 7, pp. 762-768 (Sep. 2014)(Electronic Publication Date: May 13, 2014). (Year: 2014).*
Saglani, S.Obesity, systemic inflammation and respiratory disease. Pediatric Pulmonology, (Jun. 2017) vol. 52, Supp. Supplement 46, pp. S89-S91. Abstract Number: #2. Meeting Info: 16th CIPP 2017. Lisbon, Portugal. Jun. 22, 2017-Jun. 25, 2017 (Year: 2017).*
NCT02794519 (ClinicalTrials.gov. A phase 2a study to evaluate the effects of sirukumab in subject with severe poorly controlled asthma, pp. 1-23 (Jun. 2016). (Year: 2016).*
Ano et al. Transcription Factors GATA-3 and RORyt Are Important for Determining the Phenotype of Allergic Airway Inflammation in a Murine Model of Asthma. J Immunol vol. 190 (3): 1056-1065; (2013). (Year: 2013).*
ADIS R&D Profile. Atlizumab. Anti-IL-6 receptor antibody—Chugai, Anti-interleukin-6 receptor antibody—Chugai, MRA—Chugai. Biodrugs vol. 17 (5): 369-372, (2003) (Year: 2003).*

(Continued)

*Primary Examiner* — Bridget E Bunner
*Assistant Examiner* — Regina M DeBerry
(74) *Attorney, Agent, or Firm* — Nixon & Vanderhye P.C.

(57) ABSTRACT

The present invention provides therapeutic agents for treating human asthma through administration of an IL-6 inhibitor to humans. Representative IL-6 inhibitors in the present invention include IL-6 receptor antibodies and IL-6 antibodies. Therapeutic agents of the present invention can yield therapeutic effects in severe asthma patients who need administration of high-dose steroids and such for alleviation of symptoms, or even in patients whose symptoms are difficult to control by common treatment.

9 Claims, No Drawings

Specification includes a Sequence Listing.

(56) References Cited

U.S. PATENT DOCUMENTS

| | | | |
|---|---|---|---|
| 8,323,649 | B2 | 12/2012 | Garcia-Martinez et al. |
| 8,398,980 | B2 | 3/2013 | Kano et al. |
| 8,470,316 | B2 | 6/2013 | Yasunami |
| 8,562,991 | B2 | 10/2013 | Igawa et al. |
| 8,580,264 | B2 | 11/2013 | Zhang et al. |
| 8,623,355 | B2 | 1/2014 | Okada et al. |
| 8,771,686 | B2 | 7/2014 | Ishida |
| 8,945,558 | B2 | 2/2015 | Kobara |
| 9,017,677 | B2 | 4/2015 | Mihara |
| 9,096,651 | B2 | 8/2015 | Igawa et al. |
| 9,260,516 | B2 | 2/2016 | Nishimoto et al. |
| 9,334,331 | B2* | 5/2016 | Igawa ...................... A61P 7/00 |
| 9,539,322 | B2 | 1/2017 | Nishimura |
| 9,688,762 | B2 | 6/2017 | Igawa et al. |
| 9,725,514 | B2 | 8/2017 | Takahashi et al. |
| 10,421,807 | B2* | 9/2019 | Gonzales ............... A61P 43/00 |
| 10,662,245 | B2 | 5/2020 | Igawa et al. |
| 10,697,883 | B2 | 6/2020 | Yamamura et al. |
| 10,717,781 | B2 | 7/2020 | Mitsunaga et al. |
| 10,774,148 | B2 | 9/2020 | Kakehi et al. |
| 10,782,290 | B2 | 9/2020 | Yamamura et al. |
| 2001/0001663 | A1 | 5/2001 | Kishimoto et al. |
| 2002/0119150 | A1 | 8/2002 | Kirk et al. |
| 2002/0187150 | A1 | 12/2002 | Mihara et al. |
| 2004/0018540 | A1 | 1/2004 | Yamamura et al. |
| 2004/0028681 | A1 | 2/2004 | Ito et al. |
| 2004/0071706 | A1 | 4/2004 | Ito et al. |
| 2004/0170626 | A1 | 9/2004 | Schuurman et al. |
| 2005/0096257 | A1 | 5/2005 | Shima et al. |
| 2005/0142635 | A1 | 6/2005 | Tsuchiya et al. |
| 2005/0158317 | A1 | 7/2005 | Blay et al. |
| 2005/0182007 | A1 | 8/2005 | McSWIGGEN et al. |
| 2005/0261229 | A1 | 11/2005 | Gillies et al. |
| 2005/0272634 | A1 | 12/2005 | Bahlmann et al. |
| 2006/0039902 | A1 | 2/2006 | Young et al. |
| 2006/0111316 | A1 | 5/2006 | Lawless |
| 2006/0134113 | A1 | 6/2006 | Mihara |
| 2006/0165696 | A1 | 7/2006 | Okano et al. |
| 2006/0188502 | A1 | 8/2006 | Giles-Komar et al. |
| 2006/0193772 | A1 | 8/2006 | Ochiai et al. |
| 2006/0251653 | A1 | 11/2006 | Okuda et al. |
| 2006/0292147 | A1 | 12/2006 | Yoshizaki et al. |
| 2007/0036785 | A1 | 2/2007 | Kishimoto et al. |
| 2007/0134242 | A1 | 6/2007 | Nishimoto et al. |
| 2007/0167425 | A1 | 7/2007 | Nakade et al. |
| 2007/0280945 | A1 | 12/2007 | Stevens et al. |
| 2008/0032923 | A1 | 2/2008 | Kudou et al. |
| 2008/0081041 | A1 | 4/2008 | Nemeth |
| 2009/0022719 | A1 | 1/2009 | Mihara et al. |
| 2009/0022726 | A1 | 1/2009 | Zaki et al. |
| 2009/0028784 | A1 | 1/2009 | Garcia-Martinez et al. |
| 2009/0220499 | A1 | 9/2009 | Yasunami |
| 2009/0220500 | A1 | 9/2009 | Kobara |
| 2009/0263384 | A1 | 10/2009 | Okada et al. |
| 2009/0269335 | A1 | 10/2009 | Nakashima et al. |
| 2009/0291076 | A1 | 11/2009 | Morichika et al. |
| 2010/0008907 | A1 | 1/2010 | Nishimoto et al. |
| 2010/0034811 | A1 | 2/2010 | Ishida |
| 2010/0061986 | A1 | 3/2010 | Takahashi et al. |
| 2010/0129357 | A1 | 5/2010 | Garcia-Martinez et al. |
| 2010/0247523 | A1 | 9/2010 | Kano et al. |
| 2010/0298542 | A1 | 11/2010 | Igawa et al. |
| 2010/0316636 | A1 | 12/2010 | Radin et al. |
| 2011/0076275 | A1 | 3/2011 | Igawa et al. |
| 2011/0098450 | A1 | 4/2011 | Igawa et al. |
| 2011/0111406 | A1 | 5/2011 | Igawa et al. |
| 2011/0150869 | A1 | 6/2011 | Mitsunaga et al. |
| 2011/0245473 | A1 | 10/2011 | Igawa et al. |
| 2012/0045453 | A1 | 2/2012 | Chen et al. |
| 2012/0183539 | A1 | 7/2012 | Maeda |
| 2012/0253016 | A1 | 10/2012 | Igawa et al. |
| 2012/0301460 | A1 | 11/2012 | Bao et al. |
| 2013/0034554 | A1* | 2/2013 | Garcia-Martinez ..... A61P 37/06 435/375 |
| 2013/0202588 | A1 | 8/2013 | Nishimura |
| 2013/0274133 | A1* | 10/2013 | Nielsen .............. A61K 39/3955 424/133.1 |
| 2013/0317203 | A1 | 11/2013 | Igawa et al. |
| 2015/0166666 | A1* | 6/2015 | Igawa ........................ A61P 3/00 435/69.6 |
| 2016/0022812 | A1 | 1/2016 | Mitsunaga et al. |
| 2016/0139117 | A1 | 5/2016 | Yamamura et al. |
| 2017/0056621 | A1* | 3/2017 | Stein ....................... A61P 11/00 |
| 2017/0121412 | A1 | 5/2017 | Igawa et al. |
| 2017/0362304 | A1 | 12/2017 | Fukuda et al. |
| 2018/0148509 | A1 | 5/2018 | Kakehi et al. |
| 2019/0085085 | A1 | 3/2019 | Igawa et al. |
| 2020/0231688 | A1 | 7/2020 | Igawa et al. |
| 2021/0017286 | A1 | 1/2021 | Kakehi et al. |
| 2021/0206862 | A1 | 7/2021 | Igawa et al. |
| 2022/0033489 | A1* | 2/2022 | Chatila ................ C07K 16/248 |
| 2022/0041741 | A1 | 2/2022 | Igawa et al. |
| 2022/0204608 | A1 | 6/2022 | Honda et al. |
| 2022/0220210 | A1 | 7/2022 | Takeshita et al. |
| 2022/0306755 | A1 | 9/2022 | Igawa et al. |
| 2023/0159648 | A1 | 5/2023 | Igawa et al. |
| 2024/0010738 | A1 | 1/2024 | Igawa et al. |
| 2024/0150477 | A1 | 5/2024 | Kakehi et al. |
| 2024/0158518 | A1 | 5/2024 | Ozawa et al. |
| 2024/0301075 | A1 | 9/2024 | Igawa et al. |
| 2024/0417480 | A1 | 12/2024 | Kakehi et al. |

FOREIGN PATENT DOCUMENTS

| | | |
|---|---|---|
| CA | 2203182 A1 | 5/1996 |
| CA | 2443294 A1 | 10/2002 |
| CA | 2523577 A1 | 11/2004 |
| CA | 2549467 A1 | 7/2005 |
| CA | 2560953 A1 | 9/2005 |
| CA | 2625773 A1 | 4/2007 |
| CA | 2626688 A1 | 4/2007 |
| CA | 2648644 A1 | 10/2007 |
| CA | 2700394 A1 | 4/2009 |
| CA | 2700498 A1 | 4/2009 |
| CA | 2203182 C | 11/2009 |
| CA | 2549467 C | 12/2012 |
| CA | 2443294 C | 9/2013 |
| CA | 2700498 C | 1/2016 |
| CA | 2700394 C | 10/2017 |
| CN | 1164194 A | 11/1997 |
| CN | 1297357 A | 5/2001 |
| CN | 1694894 A | 11/2005 |
| CN | 1849135 A | 10/2006 |
| CN | 100374159 C | 3/2008 |
| CN | 100374457 C | 3/2008 |
| CN | 101849006 A | 9/2010 |
| CN | 101849006 B | 5/2013 |
| CN | 103476793 A | 12/2013 |
| EP | 0361902 A2 | 4/1990 |
| EP | 0361902 B1 | 2/1994 |
| EP | 0628639 A1 | 12/1994 |
| EP | 0721783 A1 | 7/1996 |
| EP | 0783893 A1 | 7/1997 |
| EP | 0791359 A1 | 8/1997 |
| EP | 0811384 A1 | 12/1997 |
| EP | 0628639 B1 | 6/1999 |
| EP | 0931544 A2 | 7/1999 |
| EP | 0983767 A1 | 3/2000 |
| EP | 1004315 A1 | 5/2000 |
| EP | 1074268 A1 | 2/2001 |
| EP | 1108435 A1 | 6/2001 |
| EP | 1197210 A1 | 4/2002 |
| EP | 1334731 A1 | 8/2003 |
| EP | 1374900 A1 | 1/2004 |
| EP | 0721783 B1 | 3/2005 |
| EP | 1562968 A1 | 8/2005 |
| EP | 1197210 B1 | 10/2005 |
| EP | 0811384 B1 | 6/2006 |
| EP | 1690550 A1 | 8/2006 |
| EP | 1707215 A1 | 10/2006 |
| EP | 1728801 A1 | 12/2006 |
| EP | 1733740 A1 | 12/2006 |
| EP | 1074268 B1 | 1/2008 |
| EP | 1334731 B1 | 2/2008 |

(56) References Cited

FOREIGN PATENT DOCUMENTS

| | | | |
|---|---|---|---|
| EP | 1004315 | B1 | 5/2008 |
| EP | 1941907 | A1 | 7/2008 |
| EP | 1941908 | A1 | 7/2008 |
| EP | 0983767 | B1 | 9/2008 |
| EP | 1967207 | A1 | 9/2008 |
| EP | 1967209 | A1 | 9/2008 |
| EP | 1990060 | A1 | 11/2008 |
| EP | 2025346 | A1 | 2/2009 |
| EP | 2123302 | A1 | 11/2009 |
| EP | 2174667 | A1 | 4/2010 |
| EP | 2194066 | A1 | 6/2010 |
| EP | 2196220 | A1 | 6/2010 |
| EP | 2202245 | A1 | 6/2010 |
| EP | 2206775 | A1 | 7/2010 |
| EP | 2275443 | A1 | 1/2011 |
| EP | 2305306 | A1 | 4/2011 |
| EP | 2330193 | A1 | 6/2011 |
| EP | 1707215 | B1 | 3/2012 |
| EP | 0783893 | B1 | 4/2012 |
| EP | 1967209 | B1 | 6/2012 |
| EP | 1690550 | B1 | 8/2012 |
| EP | 2578233 | A1 | 4/2013 |
| EP | 1562968 | B1 | 8/2013 |
| EP | 2639305 | A1 | 9/2013 |
| EP | 2196220 | B1 | 12/2014 |
| EP | 2330193 | B1 | 6/2015 |
| EP | 1941908 | B1 | 8/2015 |
| EP | 2123302 | B1 | 12/2015 |
| EP | 2275443 | B1 | 12/2015 |
| EP | 2305306 | B1 | 2/2016 |
| EP | 1941907 | B1 | 3/2016 |
| EP | 3009518 | A1 | 4/2016 |
| EP | 1967207 | B1 | 6/2016 |
| EP | 2206775 | B1 | 6/2016 |
| EP | 2202245 | B1 | 8/2016 |
| EP | 2174667 | B1 | 1/2017 |
| EP | 2578233 | B1 | 4/2017 |
| EP | 3483283 | A1 | 5/2019 |
| ES | 2276525 | T3 | 6/2007 |
| FR | 2694767 | A1 | 2/1994 |
| FR | 2694767 | B1 | 10/1994 |
| JP | H02163096 | A | 6/1990 |
| JP | H06505253 | A | 6/1994 |
| JP | H06237772 | A | 8/1994 |
| JP | H0746998 | A | 2/1995 |
| JP | H07505609 | A | 6/1995 |
| JP | H08208514 | A | 8/1996 |
| JP | H1189582 | A | 4/1999 |
| JP | 2925181 | B2 | 7/1999 |
| JP | H11180873 | A | 7/1999 |
| JP | 3067987 | B2 | 7/2000 |
| JP | 2002527354 | A | 8/2002 |
| JP | 3345419 | B2 | 11/2002 |
| JP | 2003525243 | A | 8/2003 |
| JP | 2004028926 | A | 1/2004 |
| JP | 3525221 | B2 | 5/2004 |
| JP | 3614183 | B2 | 1/2005 |
| JP | 2005524606 | A | 8/2005 |
| JP | 2005281235 | A | 10/2005 |
| JP | 2006503001 | A | 1/2006 |
| JP | 2006512325 | A | 4/2006 |
| JP | 2006524685 | A | 11/2006 |
| JP | 3856734 | B2 | 12/2006 |
| JP | 2007528691 | A | 10/2007 |
| JP | 2008037875 | A | 2/2008 |
| JP | 2008037876 | A | 2/2008 |
| JP | 2008538931 | A | 11/2008 |
| JP | 2008297315 | A | 12/2008 |
| JP | 4468578 | B2 | 5/2010 |
| JP | 2010527615 | A | 8/2010 |
| JP | 4609877 | B2 | 1/2011 |
| JP | 4698652 | B2 | 6/2011 |
| JP | 4763043 | B2 | 8/2011 |
| JP | 4799516 | B2 | 10/2011 |
| JP | 2012500020 | A | 1/2012 |
| JP | 4869063 | B2 | 2/2012 |
| JP | 2013541594 | A | 11/2013 |
| JP | 5530635 | B2 | 6/2014 |
| JP | 5685535 | B2 | 3/2015 |
| JP | 5833823 | B2 | 12/2015 |
| KR | 20060010765 | A | 2/2006 |
| KR | 20070035482 | A | 3/2007 |
| RU | 2127117 | C1 | 3/1999 |
| RU | 2147442 | C1 | 4/2000 |
| RU | 2195960 | C2 | 1/2003 |
| RU | 2430111 | C1 | 9/2011 |
| TW | 200803895 | A | 1/2008 |
| TW | 201021829 | A | 6/2010 |
| TW | 201302219 | A1 | 1/2013 |
| TW | I440469 | B | 6/2014 |
| TW | 201642902 | A | 12/2016 |
| WO | WO 9212729 | A1 | 8/1992 |
| WO | WO-9219759 | A1 | 11/1992 |
| WO | WO-9308817 | A1 | 5/1993 |
| WO | WO-9420488 | A1 | 9/1994 |
| WO | WO-9428159 | A1 | 12/1994 |
| WO | WO-9509873 | A1 | 4/1995 |
| WO | WO-9611020 | A1 | 4/1996 |
| WO | WO-9612503 | A1 | 5/1996 |
| WO | WO-9625174 | A1 | 8/1996 |
| WO | WO-9836061 | A2 | 8/1998 |
| WO | WO-9842377 | A1 | 10/1998 |
| WO | WO-9908707 | A1 | 2/1999 |
| WO | WO-9947170 | A1 | 9/1999 |
| WO | WO-9958572 | A1 | 11/1999 |
| WO | WO-9960013 | A2 | 11/1999 |
| WO | WO-0010607 | A1 | 3/2000 |
| WO | WO-0105394 | A1 | 1/2001 |
| WO | WO-0145678 | A2 | 6/2001 |
| WO | WO 0164214 | A2 | 9/2001 |
| WO | WO-0203492 | A1 | 1/2002 |
| WO | WO-0234292 | A1 | 5/2002 |
| WO | WO-02080969 | A1 | 10/2002 |
| WO | WO-03048205 | A2 | 6/2003 |
| WO | WO-03105861 | A1 | 12/2003 |
| WO | WO-2004007701 | A1 | 1/2004 |
| WO | WO-2004039826 | A1 | 5/2004 |
| WO | WO-2004045507 | A2 | 6/2004 |
| WO | WO-2004045512 | A2 | 6/2004 |
| WO | WO 2004045520 | A2 | 6/2004 |
| WO | WO-2004071404 | A2 | 8/2004 |
| WO | WO-2004073741 | A1 | 9/2004 |
| WO | WO-2004096273 | A1 | 11/2004 |
| WO | WO-2005028514 | A1 | 3/2005 |
| WO | WO-2005037315 | A1 | 4/2005 |
| WO | WO-2005044848 | A1 | 5/2005 |
| WO | WO-2005061000 | A1 | 7/2005 |
| WO | WO-2005080429 | A1 | 9/2005 |
| WO | WO-2005090405 | A1 | 9/2005 |
| WO | WO-2005107800 | A1 | 11/2005 |
| WO | WO-2006009092 | A1 | 1/2006 |
| WO | WO-2006023144 | A2 | 3/2006 |
| WO | WO-2006070286 | A2 | 7/2006 |
| WO | WO-2006072954 | A2 | 7/2006 |
| WO | WO-2006119115 | A2 | 11/2006 |
| WO | WO-2007043641 | A1 | 4/2007 |
| WO | WO-2007046489 | A1 | 4/2007 |
| WO | WO-2007058194 | A1 | 5/2007 |
| WO | WO-2007061029 | A1 | 5/2007 |
| WO | WO-2007067976 | A2 | 6/2007 |
| WO | WO-2007074880 | A1 | 7/2007 |
| WO | WO-2007076927 | A1 | 7/2007 |
| WO | WO-2007086490 | A1 | 8/2007 |
| WO | WO-2007114319 | A1 | 10/2007 |
| WO | WO-2007116962 | A1 | 10/2007 |
| WO | WO-2007137984 | A2 | 12/2007 |
| WO | WO-2007143168 | A2 | 12/2007 |
| WO | WO-2008020079 | A1 | 2/2008 |
| WO | WO-2008090901 | A1 | 7/2008 |
| WO | WO-2008144763 | A2 | 11/2008 |
| WO | WO-2009010539 | A2 | 1/2009 |
| WO | WO-2009014263 | A1 | 1/2009 |
| WO | WO-2009041613 | A1 | 4/2009 |
| WO | WO-2009041621 | A1 | 4/2009 |

(56) References Cited

FOREIGN PATENT DOCUMENTS

| WO | WO-2009041643 A1 | 4/2009 | |
| WO | WO-2009044774 A1 | 4/2009 | |
| WO | WO-2009125825 A1 | 10/2009 | |
| WO | WO-2009148148 A1 | 12/2009 | |
| WO | WO-2010021697 A2 | 2/2010 | |
| WO | WO 2010035769 A1 | 4/2010 | |
| WO | WO-2010065078 A1 | 6/2010 | |
| WO | WO2010106812 A1 | 9/2010 | |
| WO | WO2010107108 A1 | 9/2010 | |
| WO | WO-2011013786 A1 | 2/2011 | |
| WO | WO-2011131749 A1 * | 10/2011 | ............ C07H 17/08 |
| WO | WO-2011149046 A1 | 12/2011 | |
| WO | WO-2011149051 A1 | 12/2011 | |
| WO | WO 2011154139 A2 | 12/2011 | |
| WO | WO-2012063875 A1 | 5/2012 | |
| WO | WO 2012064627 A2 | 5/2012 | |
| WO | WO-2012118750 A2 | 9/2012 | |
| WO | WO-2014200018 A1 | 12/2014 | |
| WO | WO-2016027859 A1 | 2/2016 | |
| WO | WO-2016104777 A1 | 6/2016 | |
| WO | WO-2016136933 A1 | 9/2016 | |
| WO | WO-2016186154 A1 | 11/2016 | |
| WO | WO-2018008750 A1 | 1/2018 | |
| WO | WO-2018203545 A1 | 11/2018 | |
| WO | WO 2019078344 A1 | 4/2019 | |
| WO | WO-2020117929 A1 | 6/2020 | |
| WO | WO-2020202839 A1 | 10/2020 | |
| WO | WO-2020213665 A1 | 10/2020 | |
| WO | WO2022191306 A1 | 9/2022 | |
| WO | WO2023095852 A1 | 6/2023 | |
| WO | WO2023140269 A1 | 7/2023 | |

OTHER PUBLICATIONS

Neil C. Thomson. Novel approaches to the management of non-eosinophilic asthma. Therapeutic advances in respiratory disease. vol. 10(3):211-234 (2016). (Year: 2016).*

Edwards et al. The remarkable flexibility of the human antibody repertoire; isolation of over one thousand different antibodies to a single protein, BLyS. Journal of Molecular Biology 334:103-118; (2003). (Year: 2003).*

Lloyd et al. Modelling the human immune response: performance of a 10(11) human antibody repertoire against a broad panel of therapeutically relevant antigens. Protein Engineering, Eng. Design & Selection 22(3): 159-168; (2009). (Year: 2009).*

Goel et al. Plasticity within the antigen-combining site may manifest as molecular mimicry in the humoral immune response. J. Immunol. 173: 7358-7367; (2004). (Year: 2004).*

Khan et al. Adjustable locks and flexible keys: plasticity of epitope-paratope interactions in germline antibodies. J. Immunol. 192: 5398-5405; (2014) (Year: 2014).*

Poosarla et al. teach Computational De Novo Design of Antibodies Binding to a Peptide With High Affinity. Biotechn. Bioeng. 114(6): 1331-1342; (2017). (Year: 2017).*

Almand, B., et al., "Clinical Significance of Defective Dendritic Cell Differentiation in Cancer," Clin Cancer Res., 6:1755-1766 (2000).

Almand, B., et al., "Increased Production of Immature Myeloid Cells in Cancer Patients: A Mechanism of Immunosuppression in Cancer," J Immunol., 166:678-689 (2001).

Ano, S., et al., "Transcription Factors GATA-3 and RORγt Are Important for Determining the Phenotype of Allergic Airway Inflammation in a Murine Model of Asthma," J Immunol., 190:1056-1065 (2013).

346: Anti-IL-6 treatment in two pediatric patients with severe persistent asthma with the IL4R576 variant, Presentation, AAAAI/WAO Joint Congress, Mar. 2-5, 2018, Orlando, FL, USA, https://aaaai.confex.com/aaaai/wao18/webprogram/Paper34378.html.

ANZCTR, registered trial, Trial Review, Reg. No. ACTRN12614000123640, Registered Feb. 3, 2014.

Araki, M., et al., "Efficacy of the anti-IL-6 receptor antibody tocilizumab in neuromyelitis optica," Neurology, 82:1302-1306 (2014).

Araki, M., et al., "Latest Treatments and Prospects for Neuromyelitis Optica," The Medical Frontline, 71(6):1159-1167 (2016).

Burska, A. N., et al., "Gene expression analysis in RA: towards personalized medicine," Pharmacogenomics J., 14:93-106 (2014).

Capelo, A. V., et al., "Visceral adiposity is associated with cytokines and decrease in lung function in women with persistent asthma," Rev Port Pneumol., 22(5):255-261 (2016).

Chu, D. K., et al., "Therapeutic potential of anti-IL-6 therapies for granulocytic airway inflammation in asthma," Allergy Asthma Clin Immunol., 11:14 (2015), 6 pages.

ClinicalTrials.gov, "A Phase 2a Study to Evaluate the Effects of Sirukumab in Subjects With Severe Poorly Controlled Asthma," ID: NCT02794519, Sponsored by GlaxoSmithKline, Jun. 9, 2016.

Dall'Acqua, W. F., et al., "Properties of Human IgG1s Engineered for Enhanced Binding to the Neonatal Fc Receptor (FcRn)," J Biol Chem., 281(33):23514-23524 (2006).

Doganci, A., et al., "The IL-6R a chain controls lung CD4+CD25+ Treg development and function during allergic airway inflammation in vivo," J Clin Invest., 115(2):313-325 (2005).

Feaver, R., et al., "The Anti-IL-6 Antibody Sirukumab Inhibits Vascular Inflammation in a Human Surrogate Model of Atherosclerosis," American College of Rheumatology Meeting Abstracts, Abstract No. 439 (2014).

Habara, T., et al., "The biological effects of antiadhesion agents on activated RAW264.7 macrophages," J Biomed Mater Res., 61:628-633 (2002).

Hashizume, M., et al., "IL-6 plays an essential role in neutrophilia under inflammation," Cytokine, 54:92-99 (2011).

Hashizume, M. and Ohsugi, Y., "IL-6 as a target in autoimmune disease and inflammation," Folia Pharmacol Jpn., 144:172-177 (2014).

Hisanaga, K., "Neuro-Behcet disease and neuro-Sweet disease," Clin Neurol., 52:1234-1236, (2012), English abstract.

Holmdahl, L., "The Role of Fribrinolysis in Adhesion Formation," Eur J Surg., Suppl 577:24-31 (1997).

Hong, D. S., et al., "Interleukin-6 and Its Receptor in Cancer," Cancer, 110:1911-1928 (2007).

Igawa, T., et al., "pH-dependent antigen-binding antibodies as a novel therapeutic modality," Biochim Biophys Acta., 1844(11):1943-1950 (2014).

Ishikawa, S., et al., "[SAT0079] DNA Microarray of SLE Related Genes That Respond to IL-6 Blockade with Tocilizumab an Anti-IL-6 Receptor Monoclonal Antibody," Ann Rheum Dis., 65(Suppl II):474 (2006).

Jacob, A., et al., "Detrimental role of granulocyte-colony stimulating factor in neuromyelitis optica: clinical case and histological evidence," Mult Scler J., 18(12):1801-1803 (2012).

Koch, S., et al., "IL-6 activated integrated BATF/IRF4 functions in lymphocytes are T-bet-independent and reversed by subcutaneous immunotherapy," Sci Rep., 3:1754 (2013), 9 pages.

Kosaka, H., et al., "Intergeron-γ is a therapeutic target molecule for prevention of postoperative adhesion formation," Nat Med., 14(4):437-441 (2008).

Lechner, M. G., et al., "Characterization of Cytokine-Induced Myeloid-Derived Suppressor Cells from Normal Human Peripheral Blood Mononuclear Cells," J Immunol., 185:2273-2284 (2010).

Lin, Y.-L., et al., "Critical role of IL-6 in dendritic cell-induced allergic inflammation of asthma," J Mol Med., 94:51-59 (2016).

Massoud, A. H., et al., "An asthma-associated IL4R variant exacerbates airway inflammation by promoting conversion of regulatory T cells to $T_H17$-like cells," Nat Med., 22(9):1013-1022 (2016).

Masui, T., et al., "Expression of IL-6 Receptor in Pancreatic Cancer: Involvement in VEGF Induction," Anticancer Res., 22:4093-4100 (2002).

Mulhearn, B., et al., "Using the Immunophenotype to Predict Response to Biologic Drugs in Rheumatoid Arthritis," J Pers Med., 9:46 (2019), 15 pages.

Nishimoto, N., et al., "Anti-interleukin 6 receptor antibody treatment in rheumatic disease," Ann Rheum Dis., 59(suppl 1):i21-i27 (2000).

(56)                References Cited

OTHER PUBLICATIONS

Nishimoto, N., et al., "Expressions of Immune Response Related Genes Were Normalised After Tocilizumab Treatment in Rheumatoid Arthritis (RA) Patients," Ann Rheum Diseases, 71 (Suppl 3):380, Abstract FRI0198 (2013).
Ohashi, K., et al., "Interferon γ and plasminogen activator inhibitor 1 regulate adhesion formation after partial hepatectomy," Br J Surg., 101:398-407 (2014).
Pérez-Sánchez, C., et al., "Diagnostic potential of NETosis-derived products for disease activity, atherosclerosis and therapeutic effectiveness in Rheumatoid Arthritis patients," J Autoimmun., 82:31-40 (2017).
Peters, M. C., et al., "Plasma IL6 levels, metabolic dysfunction, and asthma severity: a cross-sectional analysis of two cohorts," Lancet Respir Med., 4(7):574-584 (2016).
Reed, K. L., et al., "A neurokinin 1 receptor antagonist decreases postoperative peritoneal adhesion formation and increases peritoneal fibrinolytic activity," PNAS, 101(24):9115-9120 (2004).
Revez, J. N. M. A., "The Role of the Interleukin-6 Pathway in Asthma," Thesis, University of Queensland, 78-115 (2018), retrieved on Mar. 13, 2019, https://espace.library.ug.edu.au/view/UQ:5f9d90b/s43414462)_final_thesis.pdf.
Ruiz-Limón, P., et al., "Tocilizumab improves the proatherothrombotic profile of rheumatoid arthritis patients modulating endothelial dysfunction, NETosis, and inflammation," Transl Res., 183:87-103 (2017).
Saadoun, S., et al., "Neutrophil Protease Inhibition Reduces Neuromyelitis Optica-Immunoglobulin G-Induced Damage in Mouse Brain," Ann Neurol., 71:323-333 (2012).
Saba, A. A., et al., "Effects on Interleukin-6 and its Neutralizing Antibodies on Peritoneal Adhesion Formation and Wound Healing," Am Surg., 62(7):569-572 (1996).
Sanayama, Y., et al., "Prediction of Therapeutic Responses to Tocilizumab in Patients With Rheumatoid Arthritis," Arthritis Rheumatol., 66(6):1421-1431 (2014).
Shinriki, S., et al., "Humanized Anti-Interleukin-6 Receptor Antibody Suppresses Tumor Angiogenesis and In vivo Growth of Human Oral Squamous Cell Carcinoma," Clin Cancer Res., 15(17):5426-5434 (2009).
Sideleva, O., et al., "Obesity and Asthma: An Inflammatory Disease of Adipose Tissue Not the Airway," Am J Respir Crit Care Med., 186(7):598-605 (2012).
Sparano, A., et al., "Modulation of Th1 and Th2 Cytokine Profiles and Their Association with Advanced Head and Neck Squamous Cell Carcinoma," Otolaryngol Head Neck Surg., 131:573-576 (2004).
Suzuki, M., et al., "Anti-inflammatory mechanism of tocilizumab, a humanized anti-IL-6R antibody: effect on the expression of chemokine and adhesion molecule," Rheumatol Int., 30:309-315 (2010).
Tanaka, T., et al., "Therapeutic Targeting of the Interleukin-6 Receptor," Annu Rev Pharmacol Toxicol., 52:199-219 (2012).
Wang, J., et al., "Endogenous and Exogenous IL-6 Inhibit Aeroallergen-Induced Th2 Inflammation," J Immunol., 165:4051-4061 (2000).
Wang, J., et al., "IL-6 pathway-driven investigation of response to IL-6 receptor inhibition in rheumatoid arthritis," BMJ Open, 3:e003199 (2013), 10 pages.
Wei, G., et al., "Keratinocyte Growth Factor Combined with a Sodium Hyaluronate Gel Inhibits Postoperative Intra-Abdominal Adhesions," Int J Mol Sci., 17:1611 (2016), 17 pages.
Wright, H. L., et al., "Neutrophil biomarkers predict response to therapy with tumor necrosis factor inhibitors in rheumatoid arthritis," J Leukoc Biol., 101:785-795 (2017).
Yamamura, T., "Anti-IL-6 receptor therapy for neuromyelitis optica," Neuro Therapeut., 33(5):S120 (2016).
Yamamura, T., "Anti-IL-6 receptor antibody therapy against Neuromyelitis Optica (NMO)," The 34th Annual Meeting of the Japanese Society of Neurological Therapeutics, Nov. 4, 2016.
Yamamura, T., "Treatment failures in NMO are due to specific immunologic mechanisms," 9th Annual International Roundtable Conference on NMO, Los Angeles, Mar. 13-14, 2017.

U.S. Appl. No. 15/877,894, filed Jan. 23, 2018, Maeda, related application.
U.S. Appl. No. 16/609,053, 371(c) date Oct. 28, 2019, Matsuoka, et al., related application.
U.S. Appl. No. 16/756,404, 371(c) date Apr. 15, 2020, Fujimoto, et al., related application.
U.S. Appl. No. 16/983,115, filed Aug. 3, 2020, Kakehi, et al., related application.
U.S. Appl. No. 17/097,298, filed Nov. 13, 2020, Igawa, et al., related application.
U.S. Appl. No. 15/877,894, filed Jan. 23, 2018, Maeda.
U.S. Appl. No. 16/609,053, 371(c) date Oct. 28, 2019, Matsuoka, et al.
U.S. Appl. No. 16/756,404, 371(c) date Apr. 15, 2020, Fujimoto, et al.
U.S. Appl. No. 16/983,115, filed Aug. 3, 2020, Kakehi, et al.
U.S. Appl. No. 17/097,298, filed Nov. 13, 2020, Igawa, et al.
U.S. Appl. No. 12/085,065, filed Jun. 1, 2009, Okada, et al.
U.S. Appl. No. 12/090,061, filed Mar. 6, 2009, Yasunami.
U.S. Appl. No. 12/090,676, filed Feb. 25, 2009, Kobara.
U.S. Appl. No. 12/094,644, filed Feb. 27, 2009, Nakashima, et al.
U.S. Appl. No. 12/524,041, filed Sep. 18, 2009, Takahashi, et al.
U.S. Appl. No. 12/996,162, filed Mar. 7, 2011, Mitsunaga, et al.
U.S. Appl. No. 13/387,292, filed Apr. 3, 2012, Maeda.
U.S. Appl. No. 13/524,528, filed Jun. 15, 2012, Igawa, et al.
U.S. Appl. No. 13/700,355, filed Apr. 2, 2013, Nishimura.
U.S. Appl. No. 13/959,489, filed Aug. 5, 2013, Igawa, et al.
U.S. Appl. No. 14/878,163, filed Oct. 8, 2015, Mitsunaga, et al.
U.S. Appl. No. 14/897,498, filed Dec. 10, 2015, Yamamura, et al.
U.S. Appl. No. 15/263,617, filed Sep. 13, 2016, Igawa, et al.
U.S. Appl. No. 16/041,976, filed Jul. 23, 2018, Igawa, et al.
U.S. Appl. No. 17/437,448, filed Sep. 9, 2021, Takeshita, et al.
U.S. Appl. No. 17/509,128, filed Oct. 25, 2021, Igawa, et al.
U.S. Appl. No. 17/601,831, filed Oct. 6, 2021, Honda et al.
U.S. Appl. No. 17/829,641, filed Jun. 1, 2022, Igawa, et al.
Airoldi, I., et al., "IL-12 Can Target Human Lung Adenocarcinoma Cells and Normal Bronchial Epithelial Cells Surrounding Tumor Lesions," PLoS One, 4(7):e6119 (2009).
Chugai Seiyaku Kabushiki Kaisha Presentation of the results of the phase III international joint clinical trial of Satralizumab on Neuromyelitis Optica Spectrum Disorder at the European Committee for Treatment and Research in Multiple Sclerosis (ECTRIMS) Oct. 15, 2018.
F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Poland; submitted to clinicaltrialsregister.eu on Oct. 15, 2013; downloaded from clinicaltrialsregister.eu archive on Sep. 5, 2019 as https://www.clinicaltrialsregister.eu/ctr-search/trial/2013-003752-21/PL, 7 pages.
F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Spain; submitted to clinicaltrialsregister.eu on Mar. 11, 2015; downloaded from clinicaltrialsregister.eu archive on Sep. 5, 2019 as https://www.clinicaltrinlsnoisteceu/ctr-search/tdal/20l:-003752-21/ES, 7 pages.
F. Hoffmann-La Roche Ltd., "Efficacy and Safety Study of Satralizumab (SA237) as Add-on Therapy to Treat Participants With Neuromyelitis Optica (NMO) and NMO Spectrum Disorder (NMOSD)," Study NCT02028884, first posted on clinicaltrialsregister.eu on Jan. 7, 2014 and last updated on Apr. 13, 2021; downloaded from clinicaltrialsregister.eu archive on May 19, 2021, https://clinicaltrials.gov/ct2/show/NCT02028884.
F. Hoffmann-La Roche Ltd., "Efficacy and Safety Study of Satralizumab (SA237) as Monotherapy to Treat Participants With Neuromyelitis Optica (NMO) and Neuromyelitis Optica Spectrum Disorder (NMOSD)," Study NCT02073279, first posted on clinicaltrialsregister.eu on Feb. 27, 2014 and last updated on Mar. 24, 2021; downloaded from clinicaltrialsregister.eu archive on May 19, 2021.

(56)                References Cited

OTHER PUBLICATIONS

Hinton, P.R., et al., "An Engineered Human IgG1 Antibody With Longer Serum Half-life," Journal of Immunology, 176(1):346-356 (2006).

Kakuron III, "Section 9 Opticospinal Multiple Sclerosis," Tahatsusei Kokasho Chiryo Guideline, 104-109 (2010).

Kardas, G., et al., "Biological Therapies of Severe Asthma and Their Possible Effects on Airway Remodeling," Front Immunol., 11(1134), 8 pages (2020).

Nakamura, et al., "Clinical Characteristics of Multiple Sclerosis with High Peripheral Blood Plasmablast Frequency," Meeting Abstract, 54th Annual Meeting of the Japanese Society of Neurology, Japan (Apr. 2013).

Rikiishi, H., et al., "The roles of cytokine in organ-specific tumor metastasis," Hum Cell, 6(1):21-28 (1993). Abstract Only.

"Severe Asthma," American Academy of Allergy, Asthma & Immunology, Jul. 29, 2019, 3 pgs.

Shang, G-S., et al., "IL-6 and TNF-α promote metastasis of lung cancer by inducing epithelial- mesenchymal transition," Oncol Lett., 13:4657-4660 (2017).

Snow, M. H., "Myogenic Cell Formation in Regenerating Rat Skeletal Muscle Injured by Mincing," Anat Rec., 188:181-200 (1977).

Wikipedia, "Interleukin 6," Feb. 22, 2019, XP055598802, accessed on https://protect-us.mimecast.com/s/6UxpCmZ28nsApl8JuGhTki?domain=en.wikipedia.org, accessed on Jun. 24, 2019, 20 pages.

U.S. Appl. No. 12/680,087, filed Jan. 3, 2011, Igawa et al., related application.

U.S. Appl. No. 12/680,112, filed Jun. 23, 2010, Igawa et al., related application.

U.S. Appl. No. 12/161,733, filed Mar. 9, 2009, Ishida, related application.

U.S. Appl. No. 12/296,193, filed Apr. 15, 2009, Nishimoto et al., related application.

U.S. Appl. No. 14/520,423, filed Oct. 22, 2014, Igawa et al., related application.

U.S. Appl. No. 15/503,441, filed Feb. 13, 2017, Fukuda et al.

U.S. Appl. No. 15/553,609, filed Aug. 25, 2017, Kakehi et al., related application.

U.S. Appl. No. 15/575,027, filed Nov. 17, 2017, Yamamura et al., related application.

U.S. Appl. No. 16/838,415, filed Apr. 2, 2020, Igawa et al., related application.

U.S. Appl. No. 18/096,066, filed Jan. 12, 2023, Igawa et al., related application.

U.S. Appl. No. 18/330,420, filed Jun. 7, 2023, Kakehi et al., related application.

U.S. Appl. No. 18/340,168, filed Jun. 23, 2023, Matsuoka et al., related application.

Abdalla, A. M. E., et al., "Current Challenges of Cancer Anti-angiogenic Therapy and the Promise of Nanotherapeutics," Theranostics 8(2):533-549 (2018).

Abiatari, I., et al., "Consensus Transcriptome Signature of Perineural Invasion in Pancreatic Carcinoma," Molecular Cancer Therapeutics 8:1494-1504 (2009).

Actemra (tocilizumab), Highlights of Prescribing Information, as revised in Aug. 2017 (1 page).

Akira, S. and Kishimoto T., "The Evidence for Interleukin-6 as an Autocrine Growth Factor in Malignancy," Seminars in Cancer Biology 3(1):17-26 (1992).

Akira, S., et al., "Interleukin-6 in Biology and Medicine," Advances in immunology 54:1-78 (1993).

Alvarez, B., et al., "Tumor Necrosis Factor-a Exerts Interleukin-6-Dependent and- Independent Effects on Cultured Skeletal Muscle Cells," Biochimica et Biophysica Acta (BBA) 1542(1-3): 66-72 (2002).

Ando, K., et al., "Tocilizumab, a Proposed Therapy for the Cachexia of Interleukin6-Expressing Lung Cancer," PLOS One, 9(7):e102436 (2014).

Annual Report 2012, "Integrated Edition Including CSR Report," Chugai Pharmaceutical Co., Ltd., 154 (2013).

Araki, M., et al., "Clinical Improvement in a Patient With Neuromyelitis Optica Following Therapy With the Anti-il-6 Receptor Monoclonal Antibody Tocilizumab," Modern Rheumatology 23(4):827-831 (2013).

Araki, M., et al., "Efficacy of the Anti-il-6 Receptor Antibody Tocilizumab in Neuromyelitis Optica," Neurology 82(15): 1302-1306 (2014).

Aricha, R., et al., "Blocking of Il-6 Suppresses Experimental Autoimmune Myasthenia Gravis," Journal of Autoimmunity 36(2): 135-141 (2011).

Arima, Y., et al., "Regional Neural Activation Defines a Gateway for Autoreactive T Cells to Cross the Blood-Brain Barrier," Cell 148(3):447-457 (2012).

Armour, K.L., et al., "Recombinant Human IgG Molecules Lacking Fcgamma Receptor I Binding and Monocyte Triggering Activities," European Journal of Immunology 29(8):2613-2624 (1999).

Armstrong, C.A., et al., "Melanoma-derived Interleukin 6 Inhibits in Vivo Melanoma Growth," The Journal of Investigative Dermatology 102(3):278-284 (1994).

Ashizawa, T., et al., "Clinical Significance of Interleukin-6 (IL-6) in the Spread of Gastric Cancer: Role of IL-6 as a Prognostic Factor", Gastric Cancer 8:124-131 (2005).

Audenet, F., et al., "The Evolution of Bladder Cancer Genomics: What Have We Learned and How Can We Use It?," Urologic Oncology 36(7):313-320 (2018).

Balint, B., et al., "Alterations of the peripheral B cell compartment in paediatric-onset multiple sclerosis," J Neurol 258(1):S202, Abstract No. P732 (2011).

Barkhof, F., et al., "Comparison of MRI Criteria at First Presentation to Predict Conversion to Clinically Definite Multiple Sclerosis", Brain 120:2059-2069 (1997).

Bartelds, G.M., et al., "Clinical Response to Adalimumab: Relationship to Anti-Adalimumab Antibodies and Serum Adalimumab Concentrations in Rheumatoid Arthritis," Annals of the Rheumatic Diseases 66(7):921-926 (2007).

Barton-Davis, E.R., et al., "Viral Mediated Expression of Insulin-Like Growth Factor I Blocks the Aging-related Loss of Skeletal Muscle Function," PNAS 95(26):15603-15607 (1998).

Beck, J., et al., "Brief Report: Alleviation of Systemic Manifestations of Castleman's Disease by Monoclonal Anti-interleukin-6 Antibody," The New England Journal of Medicine 330(9):602-605 (1994).

Becker, Y., "Molecular Immunological Approaches to Biotherapy of Human Cancers—A Review, Hypothesis and Implications", Anticancer Research 29:1113-1134 (2006).

Bellomo, R., "The Cytokine Network in the Critically Ill," Anaesthesia and Intensive Care 20(3): 288-302 (1992).

Benda, B. and Korsgren, O., "Interleukin-6 in Islet Xenograft Rejection," Transplant international 14(2):63-71 (2001).

Bender, N.K., et al., "Immunogenicity, Efficacy and Adverse Events of Adalimumab in RA Patients," Rheumatology International 27(3):269-274 (2007).

Berger, T., et al., "Disruption of the Lon2 Gene in Mice Suppresses Primary Mammary Tumor Formation but Does Not Decrease Lung Metastasis", PNAS 107:2995-3000 (2010).

Bertagnolli, M.M., et al., "IL-4-Supported Induction of Cytolytic T Lymphocytes Requires IL-2 and IL-6," Cellular Immunology 133(2):327-341 (1991).

Besada, E., "Potential Patient Benefit of a Subcutaneous Formulation of Tocilizumab for the Treatment of Rheumatoid Arthritis: a Critical Review," Patient Preference and Adherence 8: 1051-1059 (2014).

Besse, B., et al., "Phase 2 Study of Frontline Bortezomib in Patients With Advanced Non-small Cell Lung Cancer," Lung Cancer 76(1):78-83 (2012).

Biswas, P.S., et al., "Involvement of IL-6 in the Paracrine Production of VEGF in Ocular HSV-1 Infection," Experimental Eye Research 82(1):46-54 (2006).

Bogdanovich, S., et al., "Functional Improvement of Dystrophic Muscle by Myostatin Blockade," Nature 420: 418-421 (2002).

(56)     References Cited

OTHER PUBLICATIONS

Bonapace, L., et al., "Cessation of CCL2 Inhibition Accelerates Breast Cancer Metastasis by Promoting Angiogenesis," Nature 515(7525):130-133 (2014).

Bond, M., et al., "Synergistic Upregulation of Metalloproteinase-9 by Growth Factors and Inflammatory Cytokines: an Absolute Requirement for Transcription Factor Nf-kappa B," FEBS Letters 435(1):29-34 (1998).

Borg, A.J., et al., "15-Deoxyspergualin Inhibits Interleukin 6 Production in in Vitro Stimulated Human Lymphocytes", Transplant Immunology 4:133-143 (1996).

Bork, P. and Bairoch, A., "Go Hunting in Sequence Databases But Watch Out for the Traps," Trends in Genetics 12(10):425-427 (1996).

Bork, P., "Powers and Pitfalls in Sequence Analysis: the 70% Hurdle," Genome Research 10(4): 398-400 (2000).

Borsellino, N., et al., "Blocking Signaling Through the Gp130 Receptor Chain by Interleukin-6 and Oncostatin M Inhibits Pc-3 Cell Growth and Sensitizes the Tumor Cells to Etoposide and Cisplatin-mediated Cytotoxicity," Cancer 85(1):134-144 (1999).

Brenner, S.E., "Errors in Genome Annotation," Trends in Genetics 15(4):132-133 (1999).

Bromberg, "The IL-6/Jak/Stat3 Pathway: Targeting Metastatic Breast Cancer Research Update," www.mountainsofhopefoundation.org, 4 pages (2009).

Brown, M., et al., "Tolerance of Single, but Not Multiple, Amino Acid Replacements in Antibody Vh Cdr 2: a Means of Minimizing B Cell Wastage From Somatic Hypermutation?," Journal of Immunology 156(9):3285-3291 (1996).

Busse, W. W., et al., "Randomized, Double-Blind, Placebo-controlled Study of Brodalumab, a Human Anti-IL-17 Receptor Monoclonal Antibody, in Moderate to Severe Asthma," Am J Respir Crit Care Med., 188(11):1294-1302 (2013).

Cabillic, F., et al., "Interleukin-6 and Vascular Endothelial Growth Factor Release by Renal Cell Carcinoma Cells Impedes Lymphocyte-dendritic Cell Cross-talk," Clinical and Experimental Immunology 146(3):518-523 (2006).

Campbell, I.L., et al., "Essential Role for Interferon-gamma and Interleukin-6 in Autoimmune Insulin-dependent Diabetes in NOD/Wehi Mice", The Journal of Clinical Investigation 87:739-742 (1991).

Campbell, I.L., et al., "Evidence for IL-6 Production by and Effects on the Pancreatic Beta-Cell," Journal of Immunology 143(4):1188-1191 (1989).

Campo, S., et al., "Comparative Activity of Sant7 and Anti-IL-6, II-6R Monoclonal Antibodies in a Murine Model of B-cell Lymphoma," Cytokine 31(5): 368-374 (2005).

Campochiaro, P.A., "Retinal and Choroidal Neovascularization, "Journal of Cellular Physiology 184(3):301-310 (2000).

Ceyhan, G.O., et al., "Neural Invasion in Pancreatic Cancer: A Mutual Tropism Between Neurons and Cancer Cells," Biochemical and Biophysical Research Communications 374:442-447 (2008).

Chargé, S.B., and Rudnicki, M.A., "Cellular and Molecular Regulation of Muscle Regeneration," Physiological Reviews 84(1): 209-238 (2004).

Chau, L.A., et al., "HuM291 (Nuvion), a Humanized Fc Receptor-Nonbinding Antibody Against CD3, Anergizes Peripheral Blood T Cells as Partial Agonist of the T Cell Receptor," Transplantation 71(7):941-950 (2001).

Cheong, Y.C., et al., "Peritoneal Healing and Adhesion Formation/Reformation," Human Reproduction Update 7(6):556-566 (2001).

Chien, N.C., et al., "Significant Structural and Functional Change of an Antigen-binding Site by a Distant Amino Acid Substitution: Proposal of a Structural Mechanism," PNAS 86(14):5532-5536 (1989).

Chihara, et al., "Autoantibody Producing Cells in Neuromyelitis Optica," Journal of Clinical and Experimental Medicine 240:534-535 (2012).

Chihara, N., et al., "Interleukin 6 Signaling Promotes Anti-Aquaporin 4 Autoantibody Production from Plasmablasts in Neuromyelitis Optica," PNAS 108(9):3701-3706 (2011).

Chirino, A.J., et al., "Minimizing the Immunogenicity of Protein Therapeutics," Drug Discovery Today 9(2):82-90 (2004).

Choi, S.E., et al., "IL-6 Protects Pancreatic Islet Beta Cells From Pro-inflammatory Cytokines-Induced Cell Death and Functional Impairment in Vitro and in Vivo," Transplant Immunology 13(1): 43-53 (2004).

Choy, E., "Inhibiting Interleukin-6 in Rheumatoid Arthritis," Current Rheumatology Reports 10(5):413-417 (2008).

Christensen, J.R., et al., "Systemic Inflammation in Progressive Multiple Sclerosis Involves Follicular T-Helper, Th17- and Activated B-Cells and Correlates with Progression," PLoS One vol. 8:e57820 (2013).

Chu, G.C., et al., "Accumulation of Succinimide in a Recombinant Monoclonal Antibody in Mildly Acidic Buffers Under Elevated Temperatures," Pharmaceutical Research 24(6):1145-1156 (2007).

Chugai NMO Clinical Trial Webinar, Sakura Star Study, dated Dec. 12, 2014, downloaded on Sep. 5, 2019 from https://s3.amazonaws.com/gjcf-wp-uploads/wp-content/uploads/2016/05/16162202/12_12_14_Chugai_Webinar_PPT_Complete_Deck_FINAL.pdf, 18 pages.

Chugai Pharmaceutical, A Phase I, Multiple-dose Study of SA237, Study JapicCTI—No. 121786; submitted to Clinicaltrials.jp on Jan. 31, 2014; downloaded from clinicaltrials.jp archive on Sep. 5, 2019 as https:/ /www.clinicaltrials.jp/cti -user/trial/Show .jsp, 5 pages.

Chugai Pharmaceutical, A phase I, multiple-dose study of SA237, Study JapicCTI—No. 121786; submitted to Clinicaltrials.jp on Jun. 19, 2012; downloaded from clinicaltrials.jp archive on Sep. 5, 2019 as https://www.clinicaltrials.jp/ctiuser/ trial/Show.jsp, 5 pages.

Chugai Pharmaceutical, A phase I, Multiple-Dose Study of SA237, Study JapicCTI—No. 121786; Submitted to Clinicaltrials.jp on Mar. 19, 2012; downloaded from clinicaltrials.jp archive on Sep. 5, 2019 as https://www.clinicaltrials.jp/cti-user/trial/Show.jsp, 5 pages.

Chugai Pharmaceutical, "Efficacy and Safety Study of Satralizumab (SA237) as Add-on Therapy to Treat Participants With Neuromyelitis Optica (NMO) and NMO Spectrum Disorder (NMOSD)," Study NCT02028884, Version 1, ClinicalTrials.gov, Jan. 6, 2014, accessed at https://clinicaltrials.gov/ct2/history/NCT02028884?V1= View#StudyPageTop, accessed on Sep. 4, 2019, 6 pages.

Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 2; submitted to ClinicalTrials.gov on Feb. 25, 2014; downloaded from ClinicalTrials.gov archive on Sep. 4, 2019 as https://clinicaltrials.gov/ct2/history/NCT02028884?V2=View#StudyPage Top, 6 pages.

Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 3; submitted to ClinicalTrials.gov on Sep. 4, 2015; downloaded from ClinicalTrials.gov archive on Sep. 4, 2019 as https://clinicaltrials.gov/ct2/history/NCT02028884?V3=View#StudyPageTop, 6 pages.

Chugai Pharmaceutical, "Efficacy and Safety Study of Satralizumab (SA237) as Add-on Therapy to Treat Participants With Neuromyelitis Optica (NMO) and NMO Spectrum Disorder (NMOSD)" Study NCT02028884, version 4, Submitted to ClinicalTrials.gov on Dec. 8, 2015; Downloaded from ClinicalTrials.gov archive on Sep. 4, 2019 as https://clinicaltrials.gov/ct2/history/NCT02028884?V4=View#StudyPageTop, 6 pages.

Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)," Study NCT02073279, Version 1, ClinicalTrials.gov, Feb. 25, 2014, accessed at https://clinicaltrials.gov/ct2/history/NCT02073279?V1=View#StudyPageTop, accessed on Sep. 4, 2019, 6 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 10; submitted to ClinicalTrials.gov on Jul. 7, 2015; downloaded from ClinicalTrials.gov archive on Sep.

(56) References Cited

OTHER PUBLICATIONS 5, 2019 as https://clinicaltrials.gov/ct2/history/NCT02073279?V IO=View#StudyPageTop, 9 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 11; submitted to ClinicalTrials.gov on Aug. 3, 2015; downloaded from ClinicalTrials.gov archive on Sep. 5, 2019 as https://clinicaltrials.gov/ct2/history/NCT02073279?V 11=View#StudyPageTop, 10 pages.

Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)", Study NCT02073279, version 12; submitted to ClinicalTrials.gov on Sep. 3, 2015; downloaded from ClinicalTrials.gov archive on Sep. 5, 2019 as https://clinicaltrials.gov/ct2/history/NCT02073279? V12=View#StudyPageTop, 10 pages.

Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)," Study NCT02073279, Version 13, ClinicalTrials.gov, Oct. 5, 2015, acccessed at https://clinicaltrials.gov/ct2/history/ NCT02073279?V13=View#StudyPageTop, accessed on Sep. 5, 2019, 10 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 14; submitted to ClinicalTrials.gov on Dec. 8, 2015; downloaded from ClinicalTrials.gov archive on Sep. 5, 2019 as https://clinicaltrials.gov/ct2/history/NCT02073279?V 14=View#StudyPage Top, 10 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 2; submitted to ClinicalTrials.gov on Jul. 22, 2014; downloaded from ClinicalTrials.gov archive on Sep. 5, 2019 as https://clinicaltrials.gov /ct2/history/NCT02073279?V 2= View#StudyPageTop, 6 pages.

Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)", Study NCT02073279, version 3; submitted to ClinicalTrials.gov on Dec. 15, 2014; downloaded from ClinicalTrials.gov archive on Sep. 5, 2019 as https://clinicaltrials.gov /ct2/history/ NCT02073279?V3= View#StudyPageTop, 7 pages.

Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)", Study NCT02073279, Version 4; Submitted to ClinicalTrials.gov on Feb. 5, 2015; downloaded from ClinicalTrials.gov archive on Sep. 5, 2019 as https://clinicaltrials.gov/ct2/history/NCT02073279? V4=View#StudyPageTop, 8 pages.

Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)," Study NCT02073279, Version 5, ClinicalTrials.gov, Feb. 6, 2015, accessed at https://clinicaltrials.gov/ct2/history/ NCT02073279?V5=View#StudyPageTop, accessed on Sep. 5, 2019, 8 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 6; submitted to ClinicalTrials.gov on Mar. 4, 2015; downloaded from ClinicalTrials.gov archive on Sep. 5, 2019 as https://clinicaltrials.gov/ct2/history/NCT02073279?V 6=View#StudyPageTop, 9 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 7; submitted to ClinicalTrials.gov on Apr. 1, 2015; downloaded from ClinicalTrials.gov archive on Sep. 5, 2019 as https://clinicaltrials.gov/ct2/history/NCT02073279?V 7=View#StudyPageTop, 9 pages.

Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)", Study NCT02073279, version 8; submitted to ClinicalTrials.gov on May 7, 2015; downloaded from ClinicalTrials.gov archive on Sep. 5, 2019 as https://clinicaltrials.gov/ct2/history/NCT02073279? V8=View#StudyPageTop, 9 pages.

Chugai Pharmaceutical, "Efficacy and Safety Study of Satralizumab (SA237) as Monotherapy to Treat Participants With Neuromyelitis Optica (NMO) and Neuromyelitis Optica Spectrum Disorder (NMOSD)," Study NCT02073279, Version 9, ClinicalTrials.gov, Jun. 5, 2015, accessed at https://clinicaltrials.gov/ct2/history/ NCT02073279?V9=View#StudyPageTop, accessed on Sep. 5, 2019, 9 pages.

Chung, Y.C., and Chang, Y.F., "Serum Interleukin-6 Levels Reflect the Disease Status of Colorectal Cancer," Journal of Surgical Oncology 83(4): 222-226 (2003).

Chuntharapai, A and Kim, K.J., "Generation of Monoclonal Antibodies to Chemokine Receptors," Methods in Enzymology 288:15-27 (1997).

Cocco, M., et al., "In Vitro Generation of Long-Lived Human Plasma Cells", Journal of Immunology 189(12):5773-5785 (2012).

Cole, M.S., et al., "Human IgG2 Variants of Chimeric Anti-CD3 are Nonmitogenic to T Cells," Journal of Immunology 159(7):3613-3621 (1997).

Cordoba, A.J., et al., "Non-Enzymatic Hinge Region Fragmentation of Antibodies in Solution," Journal of Chromatography B 818(2):115-121 (2005).

Costa, L., et al., "Efficacy of Tocilizumab in a Patient with Refractory Psoriatic Arthritis," Clinical Rheumatology 33(9):1355-1357 (2014).

Culig, Z., et al., "Interleukin-6 Regulates Androgen Receptor Activity and Prostate Cancer Cell Growth", Molecular and Cellular Endocrinology 197:231-238 (2002).

Damschroder, M.M., et al., "Framework Shuffling of Antibodies to Reduce Immunogenicity and Manipulate Functional and Biophysical Properties," Molecular Immunology 44(11):3049-3060 (2007).

Dangott, B., et al., "Dietary Creatine Monohydrate Supplementation Increases Satellite Cell Mitotic Activity During Compensatory Hypertrophy," International Journal of Sports Medicine 21(1):13-16 (2000).

Darr, K.C. and Schultz, E., "Hindlimb Suspension Suppresses Muscle Growth and Satellite Cell Proliferation," Journal of Applied Physiology 67(5): 1827-1834 (1989).

Davies, G., et al., "The Hgf/sf Antagonist Nk4 Reverses Fibroblast-and Hgf-induced Prostate Tumor Growth and Angiogenesis in Vivo," International Journal of Cancer 106(3):348-354 (2003).

Davies, J., et al., "Affinity Improvement of Single Antibody VH Domains: Residues in All Three Hypervariable Regions Affect Antigen Binding", Immunotechnology 2:169-179 (1996).

De Pascalis, R., et al., "Grafting of "Abbreviated" Complementarity-Determining Regions Containing Specificity-Determining Residues Essential for Ligand Contact to Engineer a Less Immunogenic Humanized Monoclonal Antibody," Journal of Immunology 169(6):3076-3084 (2002).

De Vita, F., et al., "Serum Levels of Interleukin-6 as a Prognostic Factor in Advanced Non-small Cell Lung Cancer," Oncology Reports 5(3): 649-652 (1998).

Demir, I.E., et al., "Nerve-cancer Interactions in the Stromal Biology of Pancreatic Cancer," Frontiers in Physiology 3(97):1-22 (2012).

Dillon, T.M., et al., "Structural and Functional Characterization of Disulfide Isoforms of the Human IgG2 Subclass," The Journal of Biological Chemistry 283(23):16206-16215 (2008).

Ding, W., et al., "The Change of Plasma Interleukin-6 Level and Cardiac Protective Effect of Monoclonal Antibody to IL-6 During Myocardial Infarction Reperfusion," Chinese Journal of Cardiology 27(1):29-32, (1998) (with English Abstract).

Doerks, T., et al., "Protein Annotation: Detective Work for Function Prediction," Trends in Genetics 14(6): 248-250 (1998).

(56)            References Cited

OTHER PUBLICATIONS

Duluc, D., et al., "Tumor-associated Leukemia Inhibitory Factor and II-6 Skew Monocyte Differentiation Into Tumor-associated Macrophage-like Cells", Blood 110:4319-4330 (2007).

Ebos, J. M. L., et al., "Accelerated Metastasis after Short-Term Treatment with a Potent Inhibitor of Tumor Angiogenesis," Cancer Cell 15(3):232-239 (2009).

Eder, I.E., et al., "Targeting the Androgen Receptor in Hormone-refractory Prostate Cancer—new Concepts," Future Oncology 1(1): 93-101 (2005).

Esty, B., et al., "Treatment of severe persistent asthma with IL-6 receptor blockade," Clin Comm., 7(5):P1639-1642.E4 (2019).

Ewert, S., et al., "Stability Improvement of Antibodies for Extracellular and Intracellular Applications: CDR Grafting to Stable Frameworks and Structure-based Framework Engineering," Methods (San Diego, Calif.), 34(2):184-199 (2004).

F. Hoffmann-La Roche Ltd., "A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD)," Study EudraCT 2013-003752-21 in Germany; submitted to clinicaltrialsregister.eu on Dec. 20, 2013; downloaded from clinicaltrialsregister.eu archive on Sep. 5, 2019 as https://www.clinicaltrialsregister.eu/ctr-search!trial/2013-003752-21/DE, 7 pages.

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Hungary; submitted to clinicaltrialsregister.eu on Feb. 25, 2015; downloaded from clinicaltrialsregister.eu archive on Sep. 5, 2019 ashttps://www.clinicaltrialsregister.eu/ctr-search/trial/2013-003752-21/HU, 6 pages.

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Italy; submitted to clinicaltrialsregister.eu on Feb. 6, 2014; downloaded from clinicaltrialsregister.eu archive on Sep. 5, 2019 as https://www.clinicaltrialsregister.eu/ctr-search/trial/2013-003752-21/IT, 5 pages.

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Poland; submitted to clinicaltrialsregister.eu on Jul. 4, 2014; downloaded from clinicaltrialsregister.eu archive on Sep. 5, 2019 ashttps://www.clinicaltrialsregister.eu/ctr-search/trial/2013-003752-21/GB, 7 pages.

F. Hoffmann-La Roche Ltd., "A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD)," Study EudraCT 2013-003752-21 in Spain; submitted to clinicaltrialsregister.eu on Mar. 11, 2015; downloaded from clinicaltrialsregister.eu archive on Sep. 5, 2019 as https://www.clinicaltrialsregister.eu/ctr-search/trial/2013-003752-21/ES, 7 pages.

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in the United Kingdom; submitted to clinicaltrialsregister.eu on Oct. 15, 2013; downloaded from clinicaltrialsregister.eu archive on Sep. 5, 2019 ashttps://www.clinicaltrialsregister.eu/ctr-search/trial/2013-003752-21/GB, 6 pages.

F. Hoffmann-La Roche Ltd., "A Multicenter, Randomized, Double-blind, Placebo- controlled, Phase 3 Study to Evaluate the Efficacy and Safety of Satralizumab (SA237) as Monotherapy in Patients With Neuromyelitis Optica (NMO) and Neuromyelitis Optica Spectrum Disorder (NMOSD)," Study EudraCT 2015-005431-41 in Croatia; submitted to clinicaltrialsregister.eu on Dec. 15, 2016; downloaded from clinicaltrialsregister.eu archive on Sep. 5, 2019 as https://www.clinicaltrialsregister.eu/ctr-search!trial/2015-005431-41/HR, 6 pages.

F. Hoffmann-La Roche Ltd., A Multicenter, Randomized, Double-blind, Placebo- controlled, Phase 3 Study to Evaluate the Efficacy and Safety of Satralizumab (SA237) as Monotherapy in Patients With Neuromyelitis Optica (NMO) and Neuromyelitis Optica Spectrum Disorder (NMOSD), Study EudraCT 2015-005431-41 in Poland; submitted to clinicaltrialsregister.eu on Apr. 7, 2016; downloaded from clinicaltrialsregister.eu archive on Sep. 5, 2019 as https://www.clinicaltrialsregister.eu/ctr-search/trial/2015-005431-41/PL, 6 pages.

F. Hoffmann-La Roche Ltd., "A multicenter, randomized, addition to baseline treatment, double-blind, placebo-controlled, Phase 3 study to evaluate the efficacy and safety of Satralizumab (SA237) in patients with neuromyelitis," Clinical Trials Register for SA-307JG, European Medicines Agency, May 19, 2014.

Finkel, M.S., et al., "Negative Inotropic Effects of Cytokines on the Heart Mediated by Nitric Oxide," Science 257(5068):387-389 (1992).

Fisniku, O., et al., "Protective Effects of PG490-88 on Chronic Allograft Rejection by Changing Intragraft Gene Expression Profiles," Transplantation Proceedings 37:1962-1964 (2005).

Fitzgerald, J. M., et al., "Benralizumab, an-anti-interleukin-5 receptor a monoclonal antibody, as add-on treatment for patients with severe, uncontrolled, eosinophilic asthma (CALIMA): a randomized, double-blind, placebo-controlled phase 3 trial," Lancet, 388(10056):2128-2141 (2016).

Ford, H.R., et al., "Evidence that Production of Interleukin 6 within the Rejecting Allograft Coincides with Cytotoxic T Lymphocyte Development," Transplantation 51 (3):656-661 (1991).

Fraunberger, P., et al., "Cytokine and Cytokine-receptor Profiles After Liver and Heart Transplantation," Transplantation Proceedings 27(3):2023-2027 (1995).

Fredj, S., et al., "Role of Interleukin-6 in Cardiomyocyte/Cardiac Fibroblast Interactions During Myocyte Hypertrophy and Fibroblast Proliferation", Journal of Cellular Physiology 204:428-436 (2005).

Fuchs, M., et al., "Role of Interleukin-6 for LV Remodeling and Survival After Experimental Myocardial Infarction," FASEB Journal 17(14):2118-2120 (2003).

Fujita, J., et al., "Anti-interleukin-6 Receptor Antibody Prevents Muscle Atrophy in Colon-26 Adenocarcinoma-bearing Mice With Modulation of Lysosomal and Atp-ubiquitin-dependent Proteolytic Pathways," International Journal of Cancer 68(5): 637-643 (1996).

Fujiwara, et al., "Control of Tumor Immunity by B Cells and Th2 Cytokines," Annual Reviews 257-269 (1999) (with an unverified English translation).

Furukawa, Y., et al., "Cytokine Gene Expression During the Development of Graft Coronary Artery Disease in Mice", Japanese Circulation Journal 63:775-782 (1999).

Furuya, Y., et al., "Interleukin-6 as a Potential Therapeutic Target for Pulmonary Arterial Hypertension," International Journal of Rheumatology 2010:720305 (2010).

Gao, S. P., et al., "Mutations in the EGFR Kinase Domain Mediate STAT3 Activation via IL-6 Production in Human Lung Adenocarcinomas," The Journal of Clinical Investigation 117(12): 3846-3856 (2007).

Garry, D.J., et al., "Myogenic Stem Cell Function is Impaired in Mice Lacking the Forkhead/winged Helix Protein Mnf," PNAS 97(10):5416-5421 (2000).

Garry, D.J., et al., "Persistent Expression of MNF Identifies Myogenic Stem Cells in Postnatal Muscles," Developmental Biology 188:280-294 (1997).

Gastroenterology, Digestive Disease Week Meeting 2006/107th Annual Meeting of the American Gastroenterological Association, 130(4) Suppl 2, 750A (May 2006).

Gessner, J.E., et al., "The IgG Fc Receptor Family," Annals of Hematology 76(6):231-248 (1998).

Ghetie, V., et al., "Increasing the Serum Persistence of an IgG Fragment by Random Mutagenesis," Nature Biotechnology 15(7):637-640 (1997).

Ghosh, S. and Karin, M., "Missing Pieces in the NF-KB Puzzle," Cell 109:S81-S96 (2002).

(56)                  References Cited

OTHER PUBLICATIONS

Giugliano, G., et al., "Verapamil Inhibits Interleukin-6 and Vascular Endothelial Growth Factor Production in Primary Cultures of Keloid Fibroblasts," British Journal of Plastic Surgery 56(8):804-809 (2003).

Greenberg, A.S., et al., "Interleukin 6 Reduces Lipoprotein Lipase Activity in Adipose Tissue of Mice in Vivo and in 3t3-l1 Adipocytes: a Possible Role for Interleukin 6 in Cancer Cachexia," Cancer Research 52(15): 4113-4116 (1992).

Greten, F.R., et al., "IKKbeta Links Inflammation and Tumorigenesis in a Mouse Model of Colitis-associated Cancer," Cell 118(3):285-296 (2004).

Grossniklaus, H.E. and Green, W.R., "Choroidal Neovascularization," American Journal of Ophthalmology 137:496-503 (2004).

Guerne, P.A., et al., "Synovium as a Source of Interleukin 6 in Vitro. Contribution to Local and Systemic Manifestations of Arthritis," The Journal of Clinical Investigation 83(2):585-592 (1989).

Guice, K.S., et al., "Anti-tumor Necrosis Factor Antibody Augments Edema Formation in Caerulein-induced Acute Pancreatitis," The Journal of Surgical Research 51(6): 495-499 (1991).

Guillen, I., et al., "Cytokine Signaling During Myocardial Infarction: Sequential Appearance of IL-1 Beta and IL-6," The American Journal of Physiology 269(2 Pt 2):R229-R235 (1995).

Guyre, P.M., et al., "Increased Potency of Fc-Receptor-Targeted Antigens," Cancer Immunology 45(3-4):146-148 (1997).

Gwechenberger, M., et al., "Cardiac Myocytes Product Interleukin-6 in Culture and in Viable Border Zone of Reperfused Infarctions", Circulation 99:546-551 (1999).

Hanahan, D and Weinberg, R.A., "Hallmarks of Cancer: the Next Generation," Cell 144(5):646-674 (2011).

Hanes, J., et al., "Picomolar Affinity Antibodies From a Fully Synthetic Naive Library Selected and Evolved by Ribosome Display," Nature Biotechnology 18(12):1287-1292 (2000).

Hashizume, M., et al., "Tocilizumab, a Humanized Anti-interleukin-6 Receptor Antibody, Improved Anemia in Monkey Arthritis by Suppressing IL-6-induced Hepcidin Production," Rheumatology International, 30(7):917-923 (2010).

Hatzi, E., et al., "N-myc Oncogene Overexpression Down-Regulates IL-6; Evidence that IL-6 Inhibits Angiogenesis and Suppresses Neuroblastoma Tumor Growth", Oncogene 21:3552-3561 (2002).

Hirai, I., et al., "Perineural Invasion in Pancreatic Cancer," Pancreas 24(1):15-25 (2002).

Hirano et al., "Complementary DNA for a novel human interleukin (BSF-2) that induces B lymphocytes to produce immunoglobulin," Nature 324: 73-76 (1986).

Hirano, T., et al., "Excessive Production of Interleukin 6/b Cell Stimulatory Factor-2 in Rheumatoid Arthritis," European Journal of Immunology 18(11):1797-1801 (1988).

Hirata, Y., et al., "Characterization of IL-6 Receptor Expression by Monoclonal and Polyclonal Antibodies", Journal of Immunology 143:2900-2906 (1989).

Hirota, H., et al., "Loss of a gp130 Cardiac Muscle Cell Survival Pathway is a Critical Event in the Onset of Heart Failure During Biomechanical Stress," Cell 97:189-198 (1999).

Hirota, H., et al., "Continuous Activation of gp130, a Signal-transducing Receptor Component for Interleukin 6-related Cytokines, Causes Myocardial Hypertrophy in Mice," PNAS 92(11):4862-4826 (1995).

Hocking, D.C., et al., "Mechanisms of Pulmonary Edema Induced by Tumor Necrosis Factor-α," Circulation Research 67:68-77 (1990).

Hoffmann, S., et al., "Inhibitory Effects of Verapamil Isomers on the Proliferation of Choroidal Endothelial Cells," Graefe's archive for clinical and experimental ophthalmology 244(3):376-381 (2006).

Holt, L.J., et al., "Domain Antibodies: Proteins for Therapy", Trends in Biotechnology 21:484-490 (2003).

Honda, S., et al., "Marginal Zone B Cells Exacerbate Endotoxic Shock via Interleukin-6 Secretion Induced by Fca/uR-coupled TLR4 Signalling," Nature Communications 7:11498 (2016).

Horinaga, M., et al., "Clinical and Pathologic Significance of Activation of Signal Transducer and Activator of Transcription 3 in Prostate Cancer," Urology 66:671-675 (2005).

Hornick, P. and Rose, M., "Chronic Rejection in the Heart," Methods in Molecular Biology 333:131-144 (2006).

Hosokawa, T., et al., "The Response to Treatment with Interferon Beta-lb in Patients with Multiple Sclerosis," Shinkei Chiryo 25:589-595 (2008) (English translation).

Houssiau, F.A., et al., "Interleukin-6 in Synovial Fluid and Serum of Patients With Rheumatoid Arthritis and Other Inflammatory Arthritides," Arthritis and Rheumatism 31(6):784-788 (1988).

Houzen, H., et al., "Increased Prevalence, Incidence, and Female Predominance of Multiple Sclerosis in Northern Japan," Journal of the Neurological Sciences 15:323(1-2):117-122 (2012).

Huang, C., et al., "Inhibition of STAT3 Activity with AG490 Decreases the Invasion of Human Pancreatic Cancer Cells in Vitro", Cancer Science 97:1417-1423 (2006).

Huang, C., et al., "Inhibitory Effect of AG490 on Invasion and Metastasis of Human Pancreatic Cancer Cells in Vitro," Chinese Journal of Oncology 28(12):890-892 (2006).

Huang, Y.W. and Vitetta, E.S., "A Monoclonal Anti-Human IL-6 Receptor Antibody Inhibits the Proliferation of Human Myeloma Cells," Hybridoma 12(5):621-630 (1993).

Hudes, G. R., et al., "Preliminary Results of a Phase I Study: A Chimeric Monoclonal Anti IL-6 Antibody CNTO 328 in Combination with Docetaxel in Patients with Hormone Refractory Prostate Cancer," Journal of Clinical Oncology 25:18S (2007).

Huizinga, T.W., et al., "Sarilumab, A Fully Human Monoclonal Antibody Against IL-6Ra in Patients with Rheumatoid Arthritis and an Inadequate Response to Methotrexate: Efficacy and Safety Results from the Randomised Saril-Ra-Mobility Part A Trial", Annals of the Rheumatic Diseases 73:1626-1634 (2014).

Hwang, W.Y., et al., "Use of Human Germline Genes in a CDR Homology-based Approach to Antibody Humanization," Methods (San Diego, Calif.) 36(1):35-42 (2005).

Idezawa, T., et al., "Interleukin-6 Functions as An Autocrine Invasion Factor of Human Pancreatic Cancer Cells," Yamanashi Medical Journal 19(2):53-67 (2004).

Idezawa, T., et al., "Interleukin-6 Functions as An Autocrine Invasion Factor of Human Pancreatic Cancer Cells," Yamanashi Medical Journal 20(2):xxxvi (2005).

Iijima, T., et al., "Tocilizumab Improves Systemic Rheumatoid Vasculitis With Necrotizing Crescentic Glomerulonephritis," Modern Rheumatology 25:138-142 (2015).

Ito, et al., Journal of Japan Surgical Society 107 (special extra issue 2):387, PS-014-5 (2006) (English translation included).

Ito, N., et al., "Induction of Interleukin-6 by Interferon Alfa and Its Abrogation by a Serine Protease Inhibitor in Patients with Chronic Hepatitis C," Hepatology 23(4):669-675 (1996).

Ito, W., et al., "The His-Probe Method: Effects of Histidine Residues Introduced into the Complementarity-Determining Regions of Antibodies on Antigen-Antibody Interactions at Different pH Values," FEBS Letters 309(1):85-88 (1992).

Itoh, et al., "Anti-IL-6 Receptor Antibody Down-Regulates Pro-Inflammation Cytokine Production of Gr-1 *CD11b* Cells and Prevents Early Loss ofIslet Grafts in the Liver of Mice in Association with Engraftments," Transplantation, 82(Supp. 3), World Transplant Congress, Abstract No. 2838 (2006).

Iwanaga, Y., et al., Immunosuppressive therapy in islet transplantation, Suizou, 26(2):197-203 (2011) (English abstract).

Izawa, A., et al., "Critical Role of Interleukin-6 and its Crosstalk with AT1 R Signaling in Acute Rejection of Murine Cardiac Allografts," Circulation Journal 71 (Suppl. 1):392 (#PE-269) (2007).

Izawa, A., et al., "Interleukin-6 Blockade Attenuates the Development of Both Acute and Chronic Rejection of Murine Cardiac Allografts: A Potential Crosstalk between Interleukin-6 and Signaling through Angiotensin II Type 1 Receptor," American Journal of Transplantation 7 (Suppl. 11):426 (#1084) (2007).

Japanese Society of Neurological Therapeutics, "Standard Neurological Therapeutics: Neuromyelitis Optica (NMO)," 30(6):777-794, (2003) (including a partial English translation).

(56) References Cited

OTHER PUBLICATIONS

Jego, G., et al., "Interleukin-6 is a Growth Factor for Nonmalignant Human Plasmablasts," Blood 97(6):1817-1822, American Society of Hematology, United States (Mar. 2001).

Jejurikar, S. S., et al., "Skeletal Muscle Denervation Increases Satellite Cell Susceptibility to Apoptosis," Plastic and Reconstructive Surgery 110:160-168 (2002).

Jeron, A., et al., "Systemic Immunosuppression Fails to Suppress Cardiac Cytokine Induction in Pressure Overload Hypertrophy in Rats," Immunobiology 205(1):51-60 (2002).

Johnson, K.A., et al., "Cation Exchange-HPLC and Mass Spectrometry Reveal C-Terminal Amidation of an IgG1 Heavy Chain," Analytical Biochemistry 360(1):75-83 (2007).

Jones, S.W., et al., "Disuse Atrophy and Exercise Rehabilitation in Humans Profoundly Affects the Expression of Genes Associated with the Regulation of Skeletal Muscle Mass," FASEB Journal 18(9):1025-1027 (2004).

Jones, T.D., et al., "Identification and Removal of a Promiscuous CD4+ T Cell Epitope From the C1 Domain of Factor VIII," Journal of Thrombosis and Haemostasis 3(5):991-1000 (2005).

Jourdan, M., et al., "An in Vitro Model of Differentiation of Memory B Cells Into Plasmablasts and Plasma Cells Including Detailed Phenotypic and Molecular Characterization", Blood 114:5173-5181 (2009).

Kallen, K.-J., et al., "New Developments in Il-6 Dependent Biology and Therapy: Where Do We Stand and What Are the Options?," Expert Opinion on Investigational Drugs 8:1327-1349 (1999).

Kami, K., et al., "Gene Expression of Receptors for IL-6, Lif, and CNTF in Regenerating Skeletal Muscles", Journal of Histochemistry and Cytochemistry 48:1203-1213 (2000).

Kamohara et al., "IL-6 no Suigan Saibo no Zoshoku-Ten'i Oyobosu Eikyo to Kanshitsu Saibo ni yoru Hatsugen Seigyo Kika," Japanese Journal of Gastroenterological Surgery 39(7):1356 (Abstract 2529) (2006).

Kampan, N.C., et al., "Immunotherapeutic Interleukin-6 or Interleukin-6 Receptor Blockade in Cancer: Challenges and Opportunities," Current Medicinal Chemistry 25(36):4785-4806 (2018).

Kan, S., et al., "The Effect of Anti-Cancer Agents on CD4+FoxP3+ Regulatory T Cell," Dai 68 Kai Annual Meeting of the Japan Cancer Association, p. 286, P-0539 (2009).

Kanda, T. and Takahashi, T., "Interleukin-6 and Cardiovascular Diseases," Japanese Heart Journal 45(2):183-193 (2004).

Karin, M. and Lin, A., "Nf-KB at the Crossroads of Life and Death", Nature Immunology 3:221-227 (2002).

Karin, M., et al., "NF-kappaB In Cancer: From Innocent Bystander to Major Culprit," Nature Reviews Cancer 2(4):301-310 (2002).

Kato, "A Case of Bronchial Asthma Where IL-6 is Considered to Have Been Involved in Making It Refractory," Shindan To Chiryo, 106(10):1287-1291 (2018).

Kayahara et al., "The Nature of Neural Invasion by Pancreatic Cancer," Pancreas 35:218- 223 (2007).

Kayahara, M., et al., "Neural Invasion and Lymph Node Metastasis in the Head of the Pancreas Carcinoma," The Japanese Journal of Gastroenterological Surgery 24(3):813-817 (1991).

Kim, S., et al., "Carcinoma-Produced Factors Activate Myeloid Cells Through TLR2 to Stimulate Metastasis," Nature 457(7225):102-106 (2009).

Kim, S.J., et al., "Antibody Engineering for the Development of Therapeutic Antibodies," Molecules and Cells 20(1):17-29 (2005).

Kishimoto, T., "Interleukin-6 and its Receptor in Autoimmunity," Journal of Autoimmunity, 5(Supp A):123-132 (1992).

Kishimoto, T., "The Biology of Interleukin-6," Blood, 74(1):1-10 (1989).

Kitahara, M., et al., "The in Vivo Anti-Tumor Effect of Human Recombinant Interleukin-6", Japanese Journal of Cancer Research 81:1032-1038 (1990).

Kitazawa, R., et al., "Interleukin-1 Receptor Antagonist and Tumor Necrosis Factor Binding Protein Decrease Osteoclast Formation and Bone Resorption in Ovariectomized Mice," The Journal of Clinical Investigation 94(6):2397-2406 (1994).

Klein, B., et al., "Interleukin-6 in Human Multiple Myeloma," Blood 85(4): 863-872 (1995).

Knulst, A.C., et al., "Cytokine Detection and Modulation in Acute Graft vs. Host Disease in Mice," Mediators of Inflammation 3(1):33-40 (1994).

Kobara, M., et al., "Antibody Against Interleukin-6 Receptor Attenuates Left Ventricular Remodelling After Myocardial Infarction in Mice," Cardiovascular Research 87:424-430 (2010).

Kobara, M., et al., "Inhibition of Interleukin-6 Signaling Attenuates Left Ventricular Remodeling After Myocardian Infarction in Mice," Journal of the American Heart Association 112(851) (2005).

Kobatake, K., et al., "Kdm6a Deficiency Activates Inflammatory Pathways, Promotes M2 Macrophage Polarization, and Causes Bladder Cancer in Cooperation with p53 Dysfunction," Clinical Cancer Research 26(8):2065-2079 (2020).

Koide, N., et al., "Establishment of Perineural Invasion Models and Analysis of Gene Expression Revealed an Invariant Chain (CD74) as a Possible Molecule Involved in Perineural Invasion in Pancreatic Cancer," Clinical Cancer Research 12(8):2419-2426 (2006).

Kondo, M., et al., "A Case of Overlap Syndrome Successfully Treated with Tocilizumab: A Hopeful Treatment Strategy for Refractory Dermatomyositis?", Rheumatology 53:1907-1908 (2014).

Konopatskaya, O., et al., Molecular Vision, Monday, May 1, 2006, 11:15 AM-1:00PM Hall B/C Poster Session Program Number/Board# Range: 1749-1764/B836-B851, 244. Antiangiogenesis: Basic Mechanisms.

Kotake et al., "Interleukin-6 and Soluble Interleukin-6 Receptors in the Synovial Fluids From Rheumatoid Arthritis Patients Are Responsible for Osteoclast-like Cell Formation," Journal of Bone and Mineral Research, 11(1):88-95 (1996).

Krieckaert, C.L., et al., "Immunogenicity of Biologic Therapies-We Need Tolerance," Nature Reviews. Rheumatology 6:558-559 (2010).

Kurdi, M., et al., "Increased Expression of IL-6 and LIF in the Hypertrophied Left Ventricle of TGR(mRen2)27 and SHR rats," Molecular and Cellular Biochemistry 269(1-2):95-101 (2005).

Kurek, J.B., et al., "The Role of Leukemia Inhibitory Factor in Skeletal Muscle Regeneration," Muscle Nerve 20:815-822 (1997).

Kurek, J.B., et al., "Up-regulation of Leukaemia Inhibitory Factor and Interleukin-6 in Transected Sciatic Nerve and Muscle Following Denervation," Neuromuscular Disorders 6(2):105-114 (1996).

Kuroda, K., et al., "Prevention of Cancer Cachexia by a Novel Nuclear Factor kB Inhibitor in Prostate Cancer," Clinical Cancer Research 11(15):5590-5594 (2005).

Latulippe, E., et al., "Comprehensive Gene Expression Analysis of Prostate Cancer Reveals Distinct Transcriptional Programs Associated with Metastatic Disease," Cancer Research 62:4499-4506 (2002).

Lancaster, J.M., et al., "Identification of Genes Associated with Ovarian Cancer Metastasis Using Microarray Expression Analysis," International Journal of Gynecological Cancer 16(5):1733-1745 (2006).

Lee, S.O., et al., "Interleukin-6 Protects LNCaP Cells From Apoptosis Induced by Androgen Deprivation Through the Stat3 Pathway," The Prostate 60(3):178-186 (2004).

Ler, L.D., et al., "Loss of Tumor Suppressor KDM6A Amplifies PRC2-Regulated Transcriptional Repression in Bladder Cancer and Can be Targeted Through Inhibition of EZH2," Science Translational Medicine 9(378):eaai8312 (2017).

Li, T., et al., "Phase II Study of the Proteasome Inhibitor Bortezomib (PS-341, Velcade®) in Chemotherapy-Naive Patients with Advanced Stage in Non-Small Cell Lung Cancer (NSCLC)," Lung Cancer 68:89-93 (2010).

Lotz, M., et al., "B Cell Stimulating Factor 2/interleukin 6 is a Costimulant for Human Thymocytes and T Lymphocytes," Journal of Experimental Medicine 167:1253-1258 (1988).

Lucchinetti, C., et al., "Heterogeneity of Multiple Sclerosis Lesions: Implications for the Pathogenesis of Demyelination," Annals of Neurology 47(6):707-717 (2000).

Luo, H., et al., "A Proteasome Inhibitor Effectively Prevents Mouse Heart Allograft Rejection," Transplantation 72(2):196-202 (2001).

Maccallum, R.M., et al., "Antibody-antigen Interactions: Contact Analysis and Binding Site Topography," Journal of Molecular Biology 262(5):732-745 (1996).

(56)　　　　　　References Cited

OTHER PUBLICATIONS

Madhok, R., et al., "Serum Interleukin 6 Levels in Rheumatoid Arthritis: Correlations With Clinical and Laboratory Indices of Disease Activity," Annals of the Rheumatic Diseases 52(3):232-234 (1993).

Maeda et al., "IKKBeta Couples Hepatocyte Death to Cytokine-driven Compensatory Proliferation That Promotes Chemical Hepatocarcinogenesis," Cell 121:977-990 (2005).

Maeda, et al., "Role of iKKbeta I NF-KB Activation for Development of Liver Metastasis," Supplement: The 58th Annual Meeting of the American Association for the Study of Liver Diseases, Hepatol., 46:Issue Supplement SI, AASLD Abstracts, p. 518A, abstract No. 630, AASLD (2007).

Maeda, S., et al., "Ikappa B Kinasebeta/nuclear Factor-kappaB Activation Controls the Development of Liver Metastasis by Way of Interleukin-6 Expression," Hepatology 50:1851-1860 (2009).

Maini, R.N., et al., "Double-blind Randomized Controlled Clinical Trial of the Interleukin-6 Receptor Antagonist, Tocilizumab, in European Patients With Rheumatoid Arthritis Who Had an Incomplete Response to Methotrexate," Arthritis and Rheumatism 54(9):2817-2829 (2006).

Marten, A., et al., "Bortezomib is Ineffective in an Orthotopic Mouse Model of Pancreatic Adenocarcinoma," Molecular Cancer Therapeutics 7:3624-3631 (2008).

Martignoni, M.E., et al., "Role of Mononuclear Cells and Inflammatory Cytokines in Pancreatic Cancer-related Cachexia," Clinical Cancer Research 11(16):5802-5808 (2005).

Matsuda, T., et al., "Establishment of an Interleukin 6 (Il 6)/B Cell Stimulatory Factor 2-Dependent Cell Line and Preparation of Anti-IL 6 Monoclonal Antibodies," European Journal of Immunology 18:951-956 (1988).

Matsumoto, M., et al., "Interleukin-10-Producing Plasmablasts Exert Regulatory Function in Autoimmune Inflammation," Immunity 41(6):1040-1051 (2014).

Matsushita et al., "Lnterleukin-6 soluble Interleukin-6 Receptor Complex Reduces Infarct Size via Inhibiting Myocardial Apoptosis," Laboratory Investigation 85:1210-1223 (2005).

Matzaraki, V., et al., "Evaluation of Serum Procalcitonin and Interleukin-6 Levels as Markers of Liver Metastasis," Clinical Biochemistry 40(5-6):336-342 (2007).

Mauro, A., "Satellite Cell of Skeletal Muscle Fibers," Journal of Biophysical and Biochemical Cytology 9:493-495 (1961).

Maynard et al., "Antibody Engineering," Annual Review of Biomedical Engineering 2:339-76 (2000).

Mccormick, K.M. and Schultz, E., "Role of Satellite Cells in Altering Myosin Expression During Avian Skeletal Muscle Hypertrophy," Developmental Dynamics 199(1):52-63 (1994).

Meng, F., et al., "Acquired Resistance To Chemotherapy in Human Cholangiocarcinoma Is Mediated By An Interleukin (il-6) Dependent Activation of the X-Linked Inhibitor of Apoptosis (xiap) Protein," Gastroenterology 128(4):Supplemental 2:A-30, Abstract No. 165 (2005).

Meng, F., et al., "Over-expression of Interleukin-6 Enhances Cell Survival and Transformed Cell Growth in Human Malignant Cholangiocytes," Journal of Hepatology 44:1055-1065 (2006).

Michalaki, V., et al., "Serum Levels of IL-6 and TNF-a Correlate with Clinicopathological Features and Patient Survival in Patients with Prostate Cancer," British Journal of Cancer 90:2312-2316, 2004.

Mihara, M., et al., "Anti-interleukin 6 Receptor Antibody Inhibits Murine Aa-amyloidosis," The Journal of Rheumatology, 31(6):1132-1138 (2004).

Mihara, M., et al., "Tocilizumab Inhibits Signal Transduction Mediated by both mIL-6R and sIL-6R, but not by the Receptors of Other Members of IL-6 Cytokine Family," Int. Immunopharmacol 5:1731-1740 (2005).

Miller, D.H., et al., "Differential Diagnosis of Suspected Multiple Sclerosis: A Consensus Approach," Multiple Sclerosis 14(9):1157-1174 (2008).

Ming, J. E., et al., "IL-6 Enhances the Generation of Cytolytic T Lymphocytes in the Allogeneic Mixed Leucocyte Reaction," Clinical and Experimental Immunology 89(1):148-153 (1992).

Mitsunaga, S., et al., "Detail Histologic Analysis of Nerve Plexus Invasion in Invasive Ductal Carcinoma of the Pancreas and Its Prognostic Impact," The American Journal of Surgical Pathology 31(11):1636-1644 (2007).

Mitsunaga, S., et al., "Nerve Invasion Distance is Dependent on Lamimin gamma2 in Tumors of Pancreatic Cancer," International Journal of Cancer 127:805-819 (2010).

Miyamoto, Y., et al., "Interleukin-6 Inhibits Radiation Induced Apoptosis in Pancreatic Cancer Cells," Anticancer Research 21(4A):2449-2456 (2001).

Mori, K., et al., "Novel Models of Cancer-related Anemia in Mice Inoculated With II-6-producing Tumor Cells," Biomedical Research, 30(1):47-51 (2009).

Moss, F.P. and Leblond, C.P., "Satellite Cells as the Source of Nuclei in Muscles of Growing Rats," The Anatomical Record 170:421-435 (1971).

Motozawa, N., et al., "Unique Circumferential Peripheral Keratitis in Relapsing Polychondritis: A Case Report," Medicine 96(41):e7951 (2017).

Mozdziak et al., "Hindlimb Suspension Reduces Muscle Regeneration," Journal of Applied Physiology, 78:136-140 (1998).

Mozdziak, P.E., et al., "Muscle Regeneration During Hindlimb Unloading Results in a Reduction in Muscle Size After Reloading," Journal of Applied Physiology 91(1):183-190 (2001).

Mozdziak, P.E., et al., "Quantitation of Satellite Cell Proliferation in Vivo Using Image Analysis," Biotech. Histochem 69:249-252 (1994).

Mozdziak, P.E., et al., "Unloading of Juvenile Muscle Results in a Reduced Muscle Size 9 wk After Reloading," Journal of Applied Physiology 88(1):158-164 (2000).

Mukaida, et al., "Cytokines and Immune Network," Rinsho Kensa 35:447-452 (1991).

Murata, et al., "Development Mechanism and Pathophysiology," Saishin-Igaku 47:49-56 (1992).

Murphy, R., "The effect of mechanical stretch on proliferation and differentiation ofC2C12 cells," FASEBJ, 18:A743 (Abstract#476.6) (2004).

Nagai, et al., "Suppression of Experimental Choroid Neovascularization by Inhibition ofInterleukin-6 Receptor," Inflammation and Regeneration 26:367 (#90) (2006) (English translation included).

Nakamura, et al., "Clinical Features of Multiple Sclerosis with High Plasmablast Frequency in Peripheral Blood," Abstract for Poster Session, Multiple Sclerosis, Keystone Symposia on Molecule and Cellular Biology, Big Sky, Montana, distributed (Jan. 2013).

Nakamura et al., "Clinical Features of Multiple Sclerosis with High Plasmablast Frequency in Peripheral Blood," Abstract, Multiple Sclerosis, Keystone Symposia on Molecule and Cellular Biology, Big Sky, Montana, published online Dec. 11, 2012.

Nakamura et al., "Clinical Features of Multiple Sclerosis with High Plasmablast Frequency in Peripheral Blood," Poster Session, 54th Annual Meeting of the Japanese Society of Neurology, Tokyo, Japan, presented Jun. 1, 2013 (with English translation).

Nakamura., et al., "Clinical Features of Multiple Sclerosis with High Plasmablast Frequency in Peripheral Blood," Poster Session, Multiple Sclerosis, Keystone Symposia on Molecular and Cellular Biology, Big Sky, Montana, (Jan. 2013).

Nakamura, et al., "IL-6-dependent Plasmablasts in Pathological Conditions of Relapsing- Remitting Multiple Sclerosis," Japanese Journal of Clinical Immunology 36:345, W5-5 (2013).

Nakamura, M., et al., "Plasmablast in the Pathology of Multiple Sclerosis," Japanese Journal of Clinical Immunology 38(5):403-411 (2015).

Nakamura, The Basics and Clinical Aspects of Angiogenesis—[II] Angiogenesis and Tumors. Invasion/Metastasis/Tumor Suppression of Angiogenesis-Inhibitory Factor NK4 (2002).

Nakashima et al., "Serum Interleukin 6 as a Prognostic Factor in Patients with Prostate Cancer," Clinical Cancer Research 6:2702-2706 (2000).

Narazaki, M., et al., "Therapeutic Effect of Tocilizumab on Two Patients with Polymyositis," Rheumatology, 50(7):1344-1346 (2011).

(56) References Cited

OTHER PUBLICATIONS

Narita, et al., "Gemcitabine Selectively Depletes CDIIb+ Gr-1 +Immature Myeloid Cells in Tumor-Bearing Mice and Enhances Anti-Tumor Immune Response," Society for Fundamental Cancer Immunology Sakai Shoroku 10:49, 2006 (with an unverified English translation).

National Cancer Institute publication (online), "Metastatic Cancer: Questions and Answers," reviewed Sep. 1, 2004, accessed Nov. 22, 2014.

National Cancer Institute, Statistical Summaries:Cancer Stat Facts:Cancer of the Pancreas https://seer.cancer.gov/statfacts/html/pancreas.html (2017).

Naugler, W.E., et al., "Gender Disparity in Liver Cancer Due to Sex Differences in MyD88-Dependent IL-6 Production," Science 317:121-124 (2007).

Negoro, S., et al., "Activation of JAK/STAT Pathway Transduces Cytoprotective Signal in Rat Acute Myocardial Infarction," Cardiovascular Research 47(4):797-805 (2000).

Ngo, J.T., et al The Protein Folding Problem and Tertiary Structure Prediction, Merz, Jr et al. Editors, Birkhauser Boston, 433-506 (1994).

Nishimoto, N., "Clinical Studies in Patients With Castleman's Disease, Crohn's Disease, and Rheumatoid Arthritis in Japan," Clinical Reviews in Allergy & Immunology 28(3):221-30 (2005).

Nishimoto, N, and Kishimoto T., "Inhibition of IL-6 for the Treatment of Inflammatory Diseases," Current Opinion in Pharmacology 4:386-391 (2004).

Nishimoto, N., et al., "Humanized Anti-interleukin-6 Receptor Antibody Treatment of Multicentric Castleman Disease," Blood 106(8):2627-2632 (2005).

Nishimoto, N., et al., "Interleukin 6: From Bench to Bedside," Nature Clinical Practice. Rheumatology 2(11):619-626 (2006).

Novick, et al., "Monoclonal Antibodies to the Soluble Human IL-6 Receptor: Affinity Purification, ELISA, and Inhibition of Ligand Binding," Hybridoma 10:137-146 (1991).

Ogata, T., et al., "Anti-IL-6 Receptor Antibody Does Not Ameliorate Radiation Pneumonia in Mice," Experimental and Therapeutic Medicine 4:273-276 (2012).

Ogata, T., et al., "Early Administration of IL-6RA Does Not Prevent Radiation-Induced Lung Injury in Mice," Radiation Oncology 5:26 (2010).

Ohno, S., et al., "Antigen-Binding Specificities of Antibodies Are Primarily Determined by Seven Residues of VH," PNAS 82(9):2945-2949 (1985).

Ohsugi, et al., "Success Story of Pre-market Approved Pipeline," Pharm. Stage 7:13-18 (2007) (English translation included).

Ohsugi, Y. and Tsuchimoto, N., "Pharmacological and Clinical Profile ofHumanized Anti-human IL-6 Receptor Antibody (Tocilizumab), a Therapeutic Drug for Castleman's Disease," Folia Pharmacologica Japonica 126(6):419-425 (2005) (with English translation).

Ohtsuka et al., "Relation of Circulating Interleukin-6 to Left Ventricular Remodeling in Patients With Reperfused Anterior Myocardial Infarction," Clinical Cardiology 27(7):417-420 (2004).

Okabe, H., Presentation, "Proprietary Innovative Antibody Engineering Technologies in Chugai Pharmaceutical," 1-78 (2012).

Okada, et al., "IL-6/BSF-2 Functions as a Killer Helper Factor in the in Vitro Induction of Cytotoxic T Cells," Journal of Immunology 141:1543-1549 (1988).

Okada, S., et al., "Elevated Serum Interleukin-6 Levels in Patients with Pancreatic Cancer," Japanese Journal of Clinical Oncology 28:12-15 (1998).

Okada, Y., et al., "Experimental Implication of Celiac Ganglionotropic Invasion of Pancreatic- Cancer Cells Bearing C-Ret Proto-Oncogene With Reference to Glial-cell-line-derived Neurotrophic Factor (GDNF)," International Journal of Cancer 81(1):67-73 (1999).

Okamoto, et al., "Inhibition of Interleukin-6 Signaling Attenuates Left Ventricular Remodeling After Experimental Myocardial Infarction," Journal of Cardiac Failure 11 (9): P066 (2005).

Okamoto, M., et al., "Interleukin-6 as a Paracrine and Autocrine Growth Factor in Human Prostatic Carcinoma Cells in Vitro," Cancer Research 57:141-146 (1997).

Okazaki, M., et al., "Characterization of Anti-Mouse Interleukin-6 Receptor Antibody," Immunology Letters 84(3):231-240 (2002).

Okiyama, N., et al., "Therapeutic Effects of Interleukin-6 Blockade in a Murine Model of Polymyositis That Does Not Require Interleukin-17A," Arthritis & Rheumatism 60(8):2505-2512 (2009).

Onda, M., et al., "Lowering the Isoelectric Point of the Fv Portion of Recombinant Immunotoxins Leads to Decreased Nonspecific Animal Toxicity Without Affecting Antitumor Activity," Cancer Research 61(13):5070-5077 (2001).

Ono, et al., "The Effect of IL-6 on the Des-gamma-carboxy Prothrombin Synthesis in Human Hepatoma Cells," Gastroenterologia Japonica 27:745-750 (1992).

Ono, K., et al., "Cytokine Gene Expression After Myocardial Infarction in Rat Hearts: Possible Implication in Left Ventricular Remodeling," Circulation 98(2):149-156 (1998).

Ozaki, H., et al., "Effectiveness of Multimodality Treatment for Resectable Pancreatic Cancer," International Journal of Pancreatology 7:195-200 (1990).

Ozaki, H., et al., "The Prognostic Significance of Lymph Node Metastasis and Intrapancreatic Perineural Invasion in Pancreatic Cancer After Curative Resection," The Japanese Journal of Surgery 29:16-22 (1999).

Padlan, E.A., et al., "Structure of an Antibody-antigen Complex: Crystal Structure of the HyHEL-10 Fab-Lysozyme Complex," PNAS 86(15):5938-5942 (1989).

Paez-Ribes, M., et al., "Antiangiogenic Therapy Elicits Malignant Progression of Tumors to Increased Local Invasion and Distant Metastasis," Cancer Cell 15(3):220-231 (2009).

Park, H., et al., "Interleukin-6 Protects MIN6 Beta Cells from Cytokin-Induced Apoptosis," Annals of the New York Academy of Sciences 1005:242-249 (2003).

Patel, N.S., et al., "Endogenous Interleukin-6 Enhances the Renal Injury, Dysfunction, and Inflammation Caused by Ischemia/Reperfusion," The Journal of Pharmacology and Experimental Therapeutics 312(3):1170-1178 (2005).

Paul, W.E., "Transplantation and Graft Rejection," Fundamental Immunology 1124-1125, Third Edition (1993).

Paul, W. E., editor, "Fundamental Immunology," Fifth Edition, 801-840 (2003).

Paule, B., "Reappraisal of the Concept of Hormone Therapy in Metastatic Prostate Cancer and Implications for Treatment," European Urology 47(6):729-735 (2005).

Pauleikhoff, "Neovascular Age-related Macular Degeneration," Retina 25:1065-84 (2005).

Pavlou, A.K. and Belsey, M.J, "The Therapeutic Antibodies Market to 2008," European Journal of Pharmaceutics and Biopharmaceutics 59(3):389-396 (2005).

Phillips, A.J., "The Challenge of Gene Therapy and DNA Delivery," The Journal of Pharmacy and Pharmacology 53(9):1169-1174 (2001).

Pikarsky, E., et al., "NF-KB Functions as a Tumour Promoter in Inflammationassociated Cancer," Nature 431:461-466 (2004).

Pini, A., et al., "Design and Use of a Phage Display Library. Human Antibodies With Subnanomolar Affinity Against a Marker of Angiogenesis Eluted From a Two-dimensional Gel," The Journal of Biological Chemistry 273(34):21769-21776 (1998).

Pirollo, K.F. and Chang, E.H., "Targeted Delivery of Small Interfering RNA: Approaching Effective Cancer Therapies," Cancer Research 68:1247-1250 (2008).

Poli, V., et al., "Interleukin-6 Deficient Mice Are Protected From Bone Loss Caused by Estrogen Depletion," The EMBO Journal 13(5):1189-1196 (1994).

Polman et al., "Diagnostic Criteria for Multiple Sclerosis: 2010 Revisions to the McDonald Criteria," Annals of Neurology 69(2):292-302 (2011).

Porgador, A., et al., "Interleukin 6 Gene Transfection Into Lewis Lung Carcinoma Tumor Cells Suppresses the Malignant Phenotype and Confers Immunotherapeutic Competence Against Parental Metastatic Cells," Cancer Research 52:3679-3686 (1992).

(56) References Cited

OTHER PUBLICATIONS

Puhakka, M., et al., "Interleukin-6 and Tumor Necrosis Factor Alpha in Relation to Myocardial Infarct Size and Collagen Formation," Journal of Cardiac Failure 9(4):325-332 (2003).

Q&A de wakaru himan to tounyoubyou, 3(6):982-984 (2004) (with English translation).

Quentmeier, H., et al., "Role of IL-6, IL-2, and IL-4 in the In Vitro Induction of Cytotoxic T Cells," Journal of Immunology 149(10):3316-3320 (1992).

Rajpal, A., et al., "A General Method for Greatly Improving the Affinity of Antibodies by Using Combinatorial Libraries," Proceedings of the National Academy of Sciences of the United States of America 102(24):8466-8471 (2005).

Ramzy, D., et al., "Cardiac Allograft Vasculopathy: A Review," Canadian Journal of Surgery 48(4):319-327 (2005).

Reddy, M.P., et al., "Elimination of Fc Receptor-dependent Effector Functions of a Modified IgG4 Monoclonal Antibody to Human Cd4," Journal of Immunology 164(4):1925-1933 (2000).

Reichert, J. M., "Antibodies to watch in 2014," mAbs 6(4): 799-802 (2014).

Reichert, J.M., et al., "Monoclonal Antibody Successes in the Clinic," Nature Biotechnology 23(9):1073-1078 (2005).

Roitt, et al., Immunology, Moscow, Mir, 110 (2000).

Rothe, A., et al., "Ribosome Display for Improved Biotherapeutic Molecules," Expert Opinion on Biological Therapy 6(2):177-187 (2006).

Rudikoff, S., et al., "Single Amino Acid Substitution Altering Antigen-binding Specificity," Proceedings of the National Academy of Sciences of the United States of America 79(6):1979-1983 (1982).

Sacchi, et al., "Treatment With Monoclonal Antibody to a Lewis Lung Carcinoma- Associated Antigen: Different Effects on Primary Tumor and its Metastases," Cancer Treatment Reviews 69:985-991 (1985).

Sack, U., et al., "Interleukin-6 in Synovial Fluid is Closely Associated With Chronic Synovitis in Rheumatoid Arthritis," Rheumatology International 13(2):45-51 (1993).

Salfeld, J.G., "Isotype Selection in Antibody Engineering," Nature Biotechnology 25(12):1369-1372 (2007).

Salgado, R., et al., "Circulating Interleukin-6 Predicts Survival in Patients with Metastatic Breast Cancer," International Journal of Cancer 103(5):642-646 (2003).

Sansone, P., et al., "IL-6 Triggers Malignant Features in Mammospheres From Human Ductal Breast Carcinoma and Normal Mammary Gland," Journal of Clinical Investigation 117(12):3988-4002 (2007).

Sarkar, F. H., et al., "Back to the Future: COX-2 Inhibitors for Chemoprevention and Cancer Therapy," Mini-Reviews in Medicinal Chemistry 7(6):599-608 (2007).

Sato, K., et al., "Reshaping a Human Antibody to Inhibit the Interleukin 6-dependent Tumor Cell Growth," Cancer Research 53(4):851-856 (1993).

Schultz, E., "Satellite Cell Proliferative Compartments in Growing Skeletal Muscles," Developmental Biology 175:84-94 (1996).

Schultz, E., et al., "Acute Effects of Hindlimb Unweighting on Satellite Cells of Growing Skeletal Muscle," Journal of applied physiology 76(1):266-70 (1994).

Schultz et al., "Response of Satellite Cells to Focal Skeletal Muscle Injury," Muscle Nerve 8:217-222 (1985).

Sebba, A., "Tocilizumab: The First Interleukin-6-Receptor Inhibitor," American Journal of Health-System Pharmacy 65(15):1413-1418 (2008).

Seddon et al., "Progression of Age-related Macular Degeneration," Arch. Ophthalmol, 123:774-782 (2005).

Serada, S., et al., "IL-6 Blockade Inhibits the Induction of Myelin Antigen-Specific Th17 Cells and Th1 Cells in Experimental Autoimmune Encephalomyelitis," Proceedings of the National Academy of Sciences 105:9041-9046 (2008).

Shewach, D. S. and Lawrence, T. S., "Gemcitabine and Radiosensitization in Human Tumor Cells," Investigational New Drugs 14:257-263 (1996).

Shima, Y., et al., "Tocilizumab, a Humanized Anti-Interleukin-6 Receptor Antibody, Ameliorated Clinical Symptoms and MRI Findings of a Patient with Ankylosing Spondylitis," Modern Rheumatology, 21(4):436-439 (2011).

Shimazaki, et al., "Hito Kotsuzuishu Model to Ko hito IL-6 Juyotai Kotai no Ko Shuyo Koka," Rinsho Ketsueki 38:281-284 (1997) (English translation provided).

Shimizu, J., et al., "IFNβ-1b May Severely Exacerbate Japanese Optic-spinal Ms in Neuromyelitis Optica Spectrum," Neurology 75(16):1423-1427 (2010).

Shimizu, H., et al., "KRP-203, a Novel Synthetic Immunosuppressant, Prolongs Graft Survival and Attenuates Chronic Rejection in Rat Skin and Heart Allografts," Circulation 111(2):222-229 (2005).

Shimizu, H., et al., "Successful Treatment with Tocilizumab for Refractory Scleritis Associated with Relapsing Polychondritis," Scandinavian Journal of Rheumatology 46:418-419 (2017).

Shimizu, K. and Oku, N., "Cancer Anti-Angiogenic Therapy," Biological and Pharmaceutical Bulletin 27(5):599-605, (2004).

Shire, S.J., et al., "Challenges in the Development of High Protein Concentration Formulations," Journal of Pharmaceutical Sciences 93(6):1390-1402 (2004).

Silpa-Archa, S., et al., "Outcome of Tocilizumab Treatment in Refractory Ocular Inflammatory Diseases," Acta Ophthalmol., 94:e400-e406 (2016).

Skolnick, J. and Fetrow, U.S., "From Genes to Protein Structure and Function: Novel Applications of Computational Approaches in the Genomic Era," Trends in Biotechnology 18(1):34-39 (2000).

Skurkovich, S.V., et al., "Anticytokine Therapy—New Approach to the Treatment of Autoimmune and Cytokine-Disturbance Diseases," Oncology and Immunopathology 2:71-80 (2003) (Partial English translation).

Sleeman, J. and Steeg, P. S., "Cancer metastasis as a therapeutic target," Eur J Cancer, 46(7):1177-1180 (2010).

Smith, P. C. and Keller, E. T., "Anti-Interleukin-6 Monoclonal Antibody Induces Regression of Human Prostate Cancer Xenografts in Nude Mice," Prostate 48:47-53 (2001).

Smith, T.F., et al., "The Challenges of Genome Sequence Annotation or "the Devil is in the Details"," Nature Biotechnology 15(12):1222-1223 (1997).

Snow, M.H., "Satellite Cell Response in Rat Soleus Muscle Undergoing Hypertrophy Due to Surgical Ablation of Synergists," The Anatomical Record 227(4):437-446 (1990).

Snow, M.H., "Myogenic Cell Formation in Regenerating Rat Skeletal Muscle Injured by Mincing. II. An Autoradiographic Study," The Anatomical Record 188:201-217 (1977).

Srivastava, et al., "Potassium Channel KIR4.1 as an Immune Target in Multiple Sclerosis," The New England Journal of Medicine 12, 367:115-123 (2012).

Stan, A.C., et al., "In Vivo Inhibition of Angiogenesis and Growth of the Human U-87 Malignant Glial Tumor by Treatment With an Antibody Against Basic Fibroblast Growth Factor," Journal of Neurosurgery 82(6):1044-1052 (1995).

Steeg, P. S. and Theodorescu, D., "Metastasis: a Therapeutic Target for Cancer," Nature Clinical Practice Oncology 5(4):206-219 (2008).

Steeg, P. S., "Tumor Metastasis: Mechanistic Insights and Clinical Challenges," Nature Medicine 12(8):895-904 (2006).

Strand, V., et al., "Biologic Therapies in Rheumatology: Lessons Learned, Future Directions," Nature Reviews. Drug Discovery 6(1):75-92 (2007).

Strassmann, G., et al., "Evidence for the Involvement of Interleukin 6 in Experimental Cancer Cachexia," The Journal of Clinical Investigation 89(5):1681-1684 (1992).

Studebaker et al., "Fibroblasts Isolated From Common Sites of Breast Cancer Metastasis Enhance Cancer Cell Growth Rates and Invasiveness in an Interleukin-6-dependent Manner," Cancer Research 68(21):9087-9095 (2008).

Sugahara, H., et al., "Expression of Interleukin-6 in Human Intrahepatic Biliary Tract and its Pathologic Significance; An Inununohistochemical and In situ Hybridization Study," Juzen Medical Society 105:819-833 (1996).

(56) References Cited

OTHER PUBLICATIONS

Sumida, K., et al., "Anti-IL-6 receptor mAb eliminates myeloid-derived suppressor cells and inhibits tumor growth by enhancing T-cell responses," Eur J Immunol., 42:2060-2072 (2012).

Suzuki, et al., "Gemcitabine Selectively Eliminates Splenic Gr-1+/CDIIb+ Myeloid Suppressor Cells in Tumor-Bearing Animals and Enhances Antitumor Immune Activity," Clinical Cancer Research 11:6713-6721 (2005).

Suzuki, H., et al.,, "Anti-Murine IL-6 Receptor Antibody Inhibits IL-6 Effects in Vivo," Immunology Letters 30(1):17-21 (1991).

Taga, T., et al., "Interleukin-6 Triggers the Association of Its Receptor With a Possible Signal Transducer, gp130," Cell 58(3):573-581 (1989).

Taga, T., et al., "Receptors for B Cell Stimulatory Factor 2" The Journal of Experimental Medicine 166:967-981 (1987).

Takahashi, H., et al., "Antiproteases in Preventing the Invasive Potential of Pancreatic Cancer Cells," Journal of the Pancreas 8(4 Suppl):501-508 (2007).

Takeda, K., et al., "Murine Tumor Cells Metastasizing Selectively in the Liver: Ability to Produce Hepatocyte-Activating Cytokines Interleukin-1 and/or -6," Japanese Journal of Cancer Research 82:1299-1308 (1991).

Takeshita, Y., et al., "Effects of Neuromyelitis Optica-IgG at the Blood-Brain Barrier in Vitro," Neurology Neuroimmunology & Neuroinflammation 4(1):e311 (2016).

Takeshita, et al., Rinsho Shinkeigaku vol. 59(Supplement 224 O-08-6) (2019).

Takeshita, Y., et al., "The Effect of NMO-IgG and Anti-IL-6 Receptor Monoclonal Antibody (SA237) for the Blood-Brain Barrier," Abstract for presentation No. O-08-6, 60th Annual Meeting of the Japanese Society of Neurology, accessed at http://www.neurology-jp.org/neuro2019/abstract/pdf/adoption_03.pdf, accessed on Feb. 18, 2019.

Takizawa, H., et al., "Growth Inhibition of Human Lung Cancer Cell Lines by Interleukin 6 in Vitro: A Possible Role in Tumor Growth via an Autocrine Mechanism," Cancer Research 53:4175-4181 (1993).

Takkinen, K., et al., "Affinity and Specificity Maturation by CDR Walking," Antibody Engineering 38:540-545 (2001).

Tamura, T., et al., "Soluble Interleukin-6 Receptor Triggers Osteoclast Formation by Interleukin 6," PNAS 90:11924-11928 (1993).

Tan, P.H., et al., "Engineering the Isoelectric Point of a Renal Cell Carcinoma Targeting Antibody Greatly Enhances ScFv Solubility," Immunotechnology: an International Journal of Immunological Engineering, 4(2):107-114 (1998).

Tanaka, F., et al., "The Anti-Human Tumor Effect and Generation of Human Cytotoxic T Cells in SCID Mice Given Human Peripheral Blood Lymphocytes by the in Vivo Transfer of the Interleukin-6 Gene Using Adenovirus Vector," Cancer Research 57(7):1335-1343 (1997).

Tantraworasin, A., et al., "Prognostic Factors of Tumor Recurrence in Completely Resected Non-Small Cell Lung Cancer," Cancer Management and Research 5:77-84 (2013).

Teeling, J.L., et al., "The Biological Activity of Human CD20 Monoclonal Antibodies is Linked to Unique Epitopes on CD20," Journal of Immunology (Baltimore, Md.: 1950) 177(1):362-371 (2006).

Tintore, M., et al., "Isolated Demyelinating Syndromes: Comparison of Different MR Imaging Criteria to Predict Conversion to Clinically Definite Multiple Sclerosis," AJNR American Journal of Neuroradiology 21:702-706 (2000).

Tisdale, M.J., "Biology of Cachexia," Journal of the National Cancer Institute 89(23):1763-1773 (1997).

Tobe, T., et al., "Targeted Disruption of the FGF2 Gene does not Prevent Choroidal Neovascularization in the Murine Model," The American Journal of Pathology, 153(5):1641-1646 (1998).

Trikha, M., et al., "Targeted Anti-Interleukin-6 Monoclonal Antibody Therapy for Cancer: A Review of the Rationale and Clinical Evidence," Clinical Cancer Research 9(13):4653-4665 (2003).

Tsuchiya, M., "Therapeutic Antibody," Credit Suisse Seminar at Fuji-Gotemba Research Laboratories, p. 21 (2006) (with English translation).

Tsujinaka, T., et al., "Interleukin 6 Receptor Antibody Inhibits Muscle Atrophy and Modulates Proteolytic Systems in Interleukin 6 Transgenic Mice," The Journal of Clinical Investigation 97(1):244-249 (1996).

Uchida, T., et al., "Increased Cerebrospinal Fluid Metalloproteinase-2 and Interleukin-6 are Associated with Albumin Quotient in Neuromyelitis Optica: Their Possible Role on Blood-Brain Barrier Disruption," Multiple Sclerosis 23(8):1072-1084 (2017).

Ulich, T. R., et al., "Intratracheal Injection of Endotoxin and Cytokines. li. Lnterleukin-6 and Transforming Growth Factor Bela Inhibit Acute Inflammation," The American Journal of Pathology 138(5):1097-1101 (1991).

Unverified English language translation of French Patent FR2694767A1, published Feb. 18, 1994, 12 pages.

U.S. National Library of Medicine (NIH) publication (online), MedlinePius Medical Encyclopedia, "Liver metastases," Accessed Nov. 22, 2014.

Vajdos, F.F., et al., "Comprehensive Functional Maps of the Antigen-binding Site of an Anti-ErbB2 Antibody Obtained With Shotgun Scanning Mutagenesis," Journal of Molecular Biology 320(2):415-428 (2002).

Valantine, H., "Cardiac Allograft Vasculopathy After Heart Transplantation: Risk Factors and Management," The Journal of Heart and Lung Transplantation 23:S187-S193 (2004).

Van Der Meulen, J., et al., "The H3K27me3 Demethylase UTX in Normal Development and Disease," Epigenetics 9(5):658-668 (2014).

Van Haaften, G., et al., "Somatic Mutations of the Histone H3K27 Demethylase Gene UTX in Human Cancer," Nature Genetics 41(5):521-523 (2009).

Van Walle, I., et al., "Immunogenicity Screening in Protein Drug Development," Expert Opinion on Biological Therapy 7(3):405-418 (2007).

Vidal, L., et al., "Making Sense of Antisense," European Journal of Cancer 41:2812-2818 (2005).

Vincent, J., et al., "5-fluorouracil Selectively Kills Tumor-associated Myeloid-derived Suppressor Cells Resulting in Enhanced T Cell-dependent Antitumor Immunity," Cancer Research 70(8):3052-3061 (2010).

Wang, L. and Shilatifard, A., "UTX Mutations in Human Cancer," Cancer Cell 35(2):168-176 (2019).

Wang, H., et al., "Phase II Study of Panobinostat and Bortezomib in Patients with Pancreatic Cancer Progressing on Gemcitabine-Based Therapy," Anticancer Research 32:1027-1032 (2012).

Wang, X.D., et al., "Mechanical Load-dependent Regulation of Satellite Cell and Fiber Size in Rat Soleus Muscle," American Journal of Physiology 290(4):C981-C989 (2006).

Warren, G.L., et al., "Physiological Role of Tumor Necrosis Factor Alpha in Traumatic Muscle Injury," FASEB Journal 16(12):1630-1632 (2002).

Waubant, et al., "Clinical Characteristics of Responders to Interferon Therapy for Relapsing MS," Neurology 61:184-189 (2003).

Weber, G.F., "Why Does Cancer Therapy Lack Effective Anti-Metastasis Drugs?," Cancer Letters 328(2):207-211 (2013).

Webber, S. A., et al., "Heart and lung transplantation in children," Lancet 368:53-69 (2006).

Wells, J.A., "Additivity of Mutational Effects in Proteins," Biochemistry 29(37):8509-8517 (1990).

Weyand, M., et al., "Serial Interleukin-6 Blood Levels Early After Cardiac Transplantation," Transplantation Proceedings 24(6):2546 (1992).

Wilansky, S., "Echocardiography in the Assessment of Complications of Myocardial Infarction," Texas Heart Institute Journal 18(4):237-242 (1991).

Wingerchuk, D.M., et al., "International Consensus Diagnostic Criteria for Neuromyelitis Optica Spectrum Disorders," Neurology 85:177-189 (2015).

Wingerchuk, D.M., et al., "Revised Diagnostic Criteria for Neuromyelitis Optica," Neurology 66(10):1485-1489 (2006).

Wingerchuk, D.M., et al., "The Spectrum of Neuromyelitis Optica," The Lancet. Neurology 6(9):805-815 (2007).

(56)    References Cited

OTHER PUBLICATIONS

Wong, B. W., et al., "Progress in Heart Transplantation," Cardiovascular Pathology 14:176-180 (2005).
Wu, H., et al., "Detory Syncytial Virus Infection in the Upper and Lower Respiratory Tractvelopment of Motavizumab, an Ultrapotent Antibody for the Prevention of Respira," Journal of Molecular biology 368(3):652-665 (2007).
Wu, H., et al., "Humanization of a Murine Monoclonal Antibody by Simultaneous Optimization of Framework and CDR Residues," Journal of Molecular Biology 294(1):151-162 (1999).
Wu, C.T., et al., "Predictive Value of CD44 in Muscle-Invasive Bladder Cancer and Its Relationship with IL-6 Signaling," Annals of Surgical Oncology 25(12):3518-3526 (2018).
Xing, Y., et al., "The Effect of Interleukin-6 on the Proliferation of Prostate Cancer Cells in vitro and the Modulation of This Procedure", Journal of Tongji Medical University 21:225-227 (2001).
Yamakawa, Y., et al., "Astrocytes Promote the Proliferation of Lung Cancer Cells in Brain Metastases via Inflammatory Cytokines, Especially IL-6," Neuroscience 48(2/3):216, P-22 (poster presentation) (2009).
Yamamoto, N., et al., "Regulatory Mechanisms for Production of IFN-$\gamma$ and TNF by Antitumor T Cells or Macroophages in the Tumor-Bearing State," Journal of Immunology 154:2281-2290 (1995).
Yamamura, T., et al., "A Double-Blind Placebo-Controlled Study of Satralizumab (SA237), a Recycling Anti-IL-6 Receptor Monoclonal Antibody, as add-on Therapy for Neuromyelitis Optica (NMO) and NMO Spectrum Disorder (NMOSD)," European Journal of Neurology, 2018, 25 (Suppl. 2), p. 536, abstract EPR3103 for presentation given on Jun. 16, 2018). EPR3103 (https://ipp-ean18.netkey.at/index.php?p=recorddetail&rid=f16c1ff3-f5ec-4b71-8a99-7c39bdc90418&t).
Yamasaki, K., et al., "Cloning and Expression of the Human Interleukin-6 (BSF-2/IFN/3 2) Receptor," Science 241(4867):825-828 (1988).
Yamauchi-Takihara, K., et al., "Hypoxic Stress Induces Cardiac Myocyte-derived Interleukin-6", Circulation 91:1520-1524 (1995).
Yan, L., "(II) Abdominal discomfort and pain," Theory and Practice of Oncology, C43 Shandong Science and Technology Press, 2 pages (2006).
Yang, Y.F., et al., "Enhanced Induction of Antitumor T-Cell Responses by Cytotoxic T Lymphocyte-associated Molecule-4 Blockade: The Effect Is Manifested Only at the Restricted Tumor-bearing Stage," Cancer Research 57: 4036-4041 (1997).
Yokota, S., et al., "Clinical Study of Tocilizumab in Children With Systemic-Onset Juvenile Idiopathic Arthritis," Clinical Reviews in Allergy & Immunology 28(3):231-238 (2005).
Yoshio-Hoshino et al., "Establishment of a New Interleukin-6 (IL-6) Receptor Inhibitor Applicable to the Gene Therapy for IL-6-Dependent Tumor," Cancer Research 67:871-875 (2007).
Yue, P., et al., "Cytokine Expression Increases in Nonmyocytes From Rats With Postinfarction Heart Failure," The American Journal of Physiology 275(1):H250-H258 (1998).
Zaki, M.H., et al., "CNTO 328, A Monoclonal Antibody to IL-6, Inhibits Human Tumor-induced Cachexia in Nude Mice," International Journal of Cancer 111:592-595 (2004).
Zangari, M., et al., "Immunomodulatory Drugs in Multiple Myeloma," Expert Opinion on Investigational Drugs 14(11):1411-1418 (2005).
Zhang, G. J. and Adachi, I., "Serum Interleukin-6 Levels Correlate to Tumor Progression and Prognosis in Metastatic Breast Carcinoma," Anticancer Research 19:1427-1432 (1999).
Zijun, L., "Tissue Infiltration," Tumor Metastasis, Shanxi Science and Technology Press, 5 pages (2007).
U.S. Appl. No. 07/364,056, filed Jun. 9, 1989, Donough, et al.
U.S. Appl. No. 07/530,580, filed May 30, 1990, Novick, et al.
U.S. Appl. No. 07/634,278, filed Dec. 19, 1990, Queen, et al.
U.S. Appl. No. 08/137,117, filed Dec. 20, 1993, Tsuchiya, et al.
U.S. Appl. No. 08/197,834, filed Feb. 17, 1994, Shimamura, et al.
U.S. Appl. No. 08/329,785, filed Oct. 27, 1994, Novick, et al.
U.S. Appl. No. 08/357,080, filed Dec. 15, 1994, Kishimoto.
U.S. Appl. No. 08/436,717, filed May 8, 1995, Tsuchiya, et al.

U.S. Appl. No. 08/553,501, filed Feb. 20, 1996, Tsuchiya, et al.
U.S. Appl. No. 08/817,084, filed Apr. 7, 1997, Kishimoto, et al.
U.S. Appl. No. 08/875,927, filed Aug. 13, 1997, Tsujinaka, et al.
U.S. Appl. No. 08/882,447, filed Jun. 26, 1997, Barbera-Guillem.
U.S. Appl. No. 09/205,231, filed Dec. 4, 1998, Tsuchiya, et al.
U.S. Appl. No. 09/646,188, filed Sep. 14, 2000, Ito, et al.
U.S. Appl. No. 09/756,125, filed Jan. 9, 2001, Kishimoto, et al.
U.S. Appl. No. 10/030,915, filed May 23, 2002, Isobe, et al.
U.S. Appl. No. 10/120,272, filed Apr. 9, 2002, Kirk, et al.
U.S. Appl. No. 10/141,766, filed May 10, 2002, Mihara, et al.
U.S. Appl. No. 10/280,716, filed Oct. 26, 2002, Giles-Komar, et al.
U.S. Appl. No. 10/399,979, filed Apr. 24, 2003, Ito; Hiroaki, et al.
U.S. Appl. No. 10/496,793, filed Nov. 30, 2004, Blay, et al.
U.S. Appl. No. 10/546,149, filed Aug. 22, 2005, Okano, et al.
U.S. Appl. No. 10/554,407, filed Oct. 24, 2005, Okuda, et al.
U.S. Appl. No. 10/569,831, filed Feb. 28, 2006, Nakade, et al.
U.S. Appl. No. 10/573,528, filed Mar. 24, 2006, Ochiai, et al.
U.S. Appl. No. 10/575,455, filed Aug. 9, 2006, Nishimoto, et al.
U.S. Appl. No. 10/593,786, filed Aug. 26, 2008, Kano, et al.
U.S. Appl. No. 10/607,050, filed Jun. 27, 2003, Yamamura, et al.
U.S. Appl. No. 10/677,227, filed Oct. 3, 2003, Ito, et al.
U.S. Appl. No. 10/714,353, filed Nov. 14, 2003, Schuurman, et al.
U.S. Appl. No. 10/837,904, filed May 4, 2004, Tsuchiya, et al.
U.S. Appl. No. 10/922,675, filed Aug. 20, 2004, Mcswiggen, et al.
U.S. Appl. No. 10/926,806, filed Aug. 26, 2004, Shima, et al.
U.S. Appl. No. 11/089,426, filed Mar. 24, 2005, Gillies, et al.
U.S. Appl. No. 11/197,488, filed Aug. 5, 2005, Young, et al.
U.S. Appl. No. 11/244,142, filed Oct. 6, 2005, Lawless.
U.S. Appl. No. 11/340,412, filed Jan. 25, 2006, Mihara.
U.S. Appl. No. 11/514,217, filed Sep. 1, 2006, Yoshizaki, et al.
U.S. Appl. No. 11/585,172, filed Oct. 24, 2006, Kishimoto, et al.
U.S. Appl. No. 11/608,342, filed Dec. 8, 2006, Zaki, et al.
U.S. Appl. No. 11/631,128, filed Feb. 20, 2007, Kudou, et al.
U.S. Appl. No. 11/809,482, filed Jun. 1, 2007, Stevens, et al.
U.S. Appl. No. 11/858,418, filed Sep. 20, 2007, Nemeth.
U.S. Appl. No. 12/085,065, filed Jun. 1, 2009, Okada, et al., related application.
U.S. Appl. No. 12/090,061, filed Mar. 6, 2009, Yasunami, related application.
U.S. Appl. No. 12/090,676, filed Feb. 25, 2009, Kobara, related application.
U.S. Appl. No. 12/094,644, filed Feb. 27, 2009, Nakashima, et al., related application.
U.S. Appl. No. 12/153,612, filed May 21, 2008, Garcia-Martinez, et al.
U.S. Appl. No. 12/159,778, filed Jun. 30, 2008, Morichika, et al.
U.S. Appl. No. 12/161,733, filed Mar. 9, 2009, Ishida.
U.S. Appl. No. 12/232,341, filed Sep. 16, 2008, Mihara, et al.
U.S. Appl. No. 12/296,193, filed Apr. 15, 2009, Nishimoto, et al.
U.S. Appl. No. 12/502,581, filed Jul. 14, 2009, Garcia-Martinez, et al.
U.S. Appl. No. 12/524,041, filed Sep. 18, 2009, Takahashi, et al., related application.
U.S. Appl. No. 12/679,922, filed Oct. 1, 2010, Igawa, et al.
U.S. Appl. No. 12/680,082, filed Jun. 25, 2010, Igawa, et al.
U.S. Appl. No. 12/680,087, filed Jan. 3, 2011, Igawa, et al.
U.S. Appl. No. 12/780,006, filed May 14, 2010, Radin, et al.
U.S. Appl. No. 12/936,587, filed Jan. 3, 2011, Igawa, et al.
U.S. Appl. No. 12/996,162, filed Mar. 7, 2011, Mitsunaga, et al., related application.
U.S. Appl. No. 13/283,177, filed Oct. 27, 2011, Chen, et al.
U.S. Appl. No. 13/290,366, filed Nov. 7, 2011, Zhang, et al.
U.S. Appl. No. 13/387,292, filed Apr. 3, 2012, Maeda, related application.
U.S. Appl. No. 13/524,528, filed Jun. 15, 2012, Igawa, et al., related application.
U.S. Appl. No. 13/700,355, filed Apr. 2, 2013, Nishimura, related application.
U.S. Appl. No. 13/959,489, filed Aug. 5, 2013, Igawa, et al., related application.
U.S. Appl. No. 14/878,163, filed Oct. 8, 2015, Mitsunaga, et al., related application.

(56)     References Cited

OTHER PUBLICATIONS

U.S. Appl. No. 14/897,498, filed Dec. 10, 2015, Yamamura, et al., related application.
U.S. Appl. No. 15/263,617, filed Sep. 13, 2016, Igawa, et al., related application.
U.S. Appl. No. 16/041,976, filed Jul. 23, 2018, Igawa, et al., related application.
U.S. Appl. No. 17/437,448, filed Sep. 9, 2021, Takeshita, et al., related application.
U.S. Appl. No. 17/509,128, filed Oct. 25, 2021, Igawa, et al., related application.
U.S. Appl. No. 17/601,831, filed Oct. 6, 2021, Honda et al., related application.
U.S. Appl. No. 17/829,641, filed Jun. 1, 2022, Igawa, et al., related application.
U.S. Appl. No. 18/280,970, filed Sep. 8, 2023, Ozawa et al., related application.
U.S. Appl. No. 18/464,407, filed Sep. 11, 2023, Igawa et al., related application.
U.S. Appl. No. 18/478,148, filed Sep. 29, 2023, Maeda, related application.
U.S. Appl. No. 18/411,372, filed Jan. 22, 2024, Kakehi et al., related application.
U.S. Appl. No. 18/280,970, filed Sep. 8, 2023, Ozawa et al.
U.S. Appl. No. 18/464,407, filed Sep. 11, 2023, Igawa et al.
U.S. Appl. No. 18/478,148, filed Sep. 29, 2023, Maeda.
U.S. Appl. No. 18/411,372, filed Jan. 22, 2024, Kakehi et al.
U.S. Appl. No. 18/633,674, filed Apr. 12, 2024, Igawa et al., related application.
U.S. Appl. No. 18/651,896, filed May 1, 2024, Igawa et al., related application.
U.S. Appl. No. 18/729,273, filed Jul. 16, 2024, Ozawa et al., related application.
U.S. Appl. No. 18/820,608, filed Aug. 30, 2024, Kakehi et al., related application.
U.S. Appl. No. 18/712,917, filed May 23, 2024, Ozawa et al., related application.
U.S. Appl. No. 18/956,095, filed Nov. 22, 2024, Igawa et al., related application.
U.S. Appl. No. 18/975,370, filed Dec. 10, 2024, Igawa et al., related application.

* cited by examiner

SEQUENCE LISTING

<160> NUMBER OF SEQ ID NOS: 8

<210> SEQ ID NO 1
<211> LENGTH: 119
<212> TYPE: PRT
<213> ORGANISM: Artificial Sequence
<220> FEATURE:
<223> OTHER INFORMATION: An artificially synthesized polypeptide
      sequence

<400> SEQUENCE: 1

Gln Val Gln Leu Gln Glu Ser Gly Pro Gly Leu Val Arg Pro Ser Gln
1               5               10               15

Thr Leu Ser Leu Thr Cys Thr Val Ser Gly Tyr Ser Ile Thr Ser Asp
          20               25               30

His Ala Trp Ser Trp Val Arg Gln Pro Pro Gly Arg Gly Leu Glu Trp
          35               40               45

Ile Gly Tyr Ile Ser Tyr Ser Gly Ile Thr Thr Tyr Asn Pro Ser Leu
          50               55               60

Lys Ser Arg Val Thr Met Leu Arg Asp Thr Ser Lys Asn Gln Phe Ser
65               70               75               80

Leu Arg Leu Ser Ser Val Thr Ala Ala Asp Thr Ala Val Tyr Tyr Cys
          85               90               95

Ala Arg Ser Leu Ala Arg Thr Thr Ala Met Asp Tyr Trp Gly Gln Gly
          100             105            110

Ser Leu Val Thr Val Ser Ser
          115

<210> SEQ ID NO 2
<211> LENGTH: 107
<212> TYPE: PRT
<213> ORGANISM: Artificial Sequence
<220> FEATURE:
<223> OTHER INFORMATION: An artificially synthesized polypeptide
      sequence

<400> SEQUENCE: 2

Asp Ile Gln Met Thr Gln Ser Pro Ser Ser Leu Ser Ala Ser Val Gly
1               5               10               15

Asp Arg Val Thr Ile Thr Cys Arg Ala Ser Gln Asp Ile Ser Ser Tyr
          20               25               30

Leu Asn Trp Tyr Gln Gln Lys Pro Gly Lys Ala Pro Lys Leu Leu Ile
          35               40               45

Tyr Tyr Thr Ser Arg Leu His Ser Gly Val Pro Ser Arg Phe Ser Gly
          50               55               60

Ser Gly Ser Gly Thr Asp Phe Thr Phe Thr Ile Ser Ser Leu Gln Pro
65               70               75               80

Glu Asp Ile Ala Thr Tyr Tyr Cys Gln Gln Gly Asn Thr Leu Pro Tyr
          85               90               95

Thr Phe Gly Gln Gly Thr Lys Val Glu Ile Lys
          100             105

<210> SEQ ID NO 3
<211> LENGTH: 448
<212> TYPE: PRT
<213> ORGANISM: Artificial Sequence
<220> FEATURE:
<223> OTHER INFORMATION: An artificially synthesized polypeptide
      sequence

<400> SEQUENCE: 3

-continued

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
            35                  40                  45

Ile Gly Tyr Ile Ser Tyr Ser Gly Ile Thr Thr Tyr Asn Pro Ser Leu
        50                  55                  60

Lys Ser Arg Val Thr Met Leu Arg Asp Thr Ser Lys Asn Gln Phe Ser
65              70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

-continued

```
Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
        435                 440                 445

<210> SEQ ID NO 4
<211> LENGTH: 214
<212> TYPE: PRT
<213> ORGANISM: Artificial Sequence
<220> FEATURE:
<223> OTHER INFORMATION: An artificially synthesized polypeptide
      sequence

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 5
<211> LENGTH: 119
<212> TYPE: PRT
<213> ORGANISM: Artificial Sequence
<220> FEATURE:
<223> OTHER INFORMATION: An artificially synthesized polypeptide
      sequence

<400> SEQUENCE: 5

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45
```

```
Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser
        115
```

```
<210> SEQ ID NO 6
<211> LENGTH: 107
<212> TYPE: PRT
<213> ORGANISM: Artificial Sequence
<220> FEATURE:
<223> OTHER INFORMATION: An artificially synthesized polypeptide
      sequence

<400> SEQUENCE: 6

Asp Ile Gln Met Thr Gln Ser Pro Ser Ser Leu Ser Ala Ser Val Gly
1               5                   10                  15

Asp Ser Val Thr Ile Thr Cys Gln Ala Ser Thr Asp Ile Ser Ser His
                20                  25                  30

Leu Asn Trp Tyr Gln Gln Lys Pro Gly Lys Ala Pro Glu Leu Leu Ile
            35                  40                  45

Tyr Tyr Gly Ser His Leu Leu Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu
            100                 105
```

```
<210> SEQ ID NO 7
<211> LENGTH: 443
<212> TYPE: PRT
<213> ORGANISM: Artificial Sequence
<220> FEATURE:
<223> OTHER INFORMATION: An artificially synthesized polypeptide
      sequence

<400> SEQUENCE: 7

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
                20                  25                  30

His Ala Trp Ser Trp Val Arg Gln Pro Pro Gly Glu Gly Leu Glu Trp
            35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110
```

-continued

```
Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Ser Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Glu Gly Asn Val Phe Ser Cys Ser Val Met His Glu Ala Leu His Ala
            420                 425                 430

His Tyr Thr Gln Lys Ser Leu Ser Leu Ser Pro
        435                 440

<210> SEQ ID NO 8
<211> LENGTH: 214
<212> TYPE: PRT
<213> ORGANISM: Artificial Sequence
<220> FEATURE:
<223> OTHER INFORMATION: An artificially synthesized polypeptide
      sequence

<400> SEQUENCE: 8

Asp Ile Gln Met Thr Gln Ser Pro Ser Ser Leu Ser Ala Ser Val Gly
1               5                   10                  15

Asp Ser Val Thr Ile Thr Cys Gln Ala Ser Thr Asp Ile Ser Ser His
            20                  25                  30
```

-continued

```
Leu Asn Trp Tyr Gln Gln Lys Pro Gly Lys Ala Pro Glu Leu Leu Ile
        35              40                  45

Tyr Tyr Gly Ser His Leu Leu Ser Gly Val Pro Ser Arg Phe Ser Gly
    50              55                  60

Ser Gly Ser Gly Thr Asp Phe Thr Phe Thr Ile Ser Ser Leu Glu Ala
65              70                  75                  80

Glu Asp Ala Ala Thr Tyr Tyr Cys Gly Gln Gly Asn Arg Leu Pro Tyr
            85                  90                  95

Thr Phe Gly Gln Gly Thr Lys Val Glu Ile Glu Arg Thr Val Ala Ala
            100             105             110

Pro Ser Val Phe Ile Phe Pro Pro Ser Asp Glu Gln Leu Lys Ser Gly
        115             120             125

Thr Ala Ser Val Val Cys Leu Leu Asn Asn Phe Tyr Pro Arg Glu Ala
    130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
            165             170             175

Ser Thr Leu Thr Leu Ser Lys Ala Asp Tyr Glu Lys His Lys Val Tyr
            180             185             190

Ala Cys Glu Val Thr His Gln Gly Leu Ser Ser Pro Val Thr Lys Ser
        195             200             205

Phe Asn Arg Gly Glu Cys
    210
```

THERAPEUTIC AGENT FOR ASTHMA CONTAINING IL-6 INHIBITOR

CROSS-REFERENCE TO RELATED APPLICATIONS

This application is a U.S. National Phase of PCT Application No. PCT/JP2019/003438, filed Jan. 31, 2019, which claims the benefit of Japanese Patent Application No. 2018-015983, filed Jan. 31, 2018, and Japanese Patent Application No. 2018-187251, filed Oct. 2, 2018, each of which is incorporated herein by reference in its entirety.

REFERENCE TO SEQUENCE LISTING SUBMITTED ELECTRONICALLY

The content of the electronically submitted sequence listing (Name: 6663_0143_Sequence_Listing.txt; Size: 16.1 kilobytes; and Date of Creation: Jul. 20, 2020) filed with the application is incorporated herein by reference in its entirety.

TECHNICAL FIELD

The present invention relates to therapeutic agents for asthma containing an IL-6 inhibitor.

BACKGROUND ART

Bronchial asthma is a disease characterized by clinical manifestation of variable airway narrowing (wheezing and dyspnea) and cough, and its essence is chronic inflammation of the airway. In addition to inflammatory cells such as eosinophils, neutrophils, lymphocytes, and mast cells, cells constituting the airway such as airway epithelial cells, fibroblasts, and airway smooth muscle cells, as well as various humoral factors are involved in airway inflammation.

The currently achievable goal for management and treatment is alleviating or ameliorating airway hyperresponsiveness and airflow limitation by dilating the airways and suppressing inflammation through drug therapy and avoidance and removal of factors initiating airway inflammation.

The goal is to consequently normalize the respiratory function as much as possible and improve the QOL of patients so that they can lead daily lives not different from healthy individuals.

Since the essence of asthmatic airway inflammation is mainly eosinophilic inflammation, the drug therapy is performed basically by inhaled steroids (inhaled corticosteroids (ICS)), and bronchodilators such as long-acting β2-agonist (LABA), long-acting anticholinergics (long-acting muscarinic antagonist (LAMA)), leukotriene receptor antagonists (LTRA), and controlled-release theophylline formulations are used in combination depending on the therapeutic step. Oral steroids (oral corticosteroids (OCS)) and biological formulations of anti-IgE antibodies and anti-IL-5 antibodies, etc. are additionally administered when the severity is higher; however, sufficient control may not be achieved despite such treatments.

Such asthma that requires administration of high dose ICS combined with two or more pharmaceutical agents selected from the group consisting of LABA, LTRA, controlled-release theophylline formulations, LAMA, OCS, anti-IgE antibodies, and IL-5 antibodies, or asthma which remains uncontrollable despite such treatments are called refractory asthma or severe asthma (Guidelines for Prevention and Control of Asthma, 2015).

The following definitions are provided in the ERS/ATS severe asthma guidelines. Asthma that required treatment suggested for GINA steps 4 to 5 asthma (high-dose ICS plus LABA or LTRA/theophylline agent) for the previous year or systemic steroid agents for the number of days reaching 50% or more than that of the previous year to prevent it from becoming "uncontrolled", or asthma which remains "uncontrolled" despite the treatments described above, are defined as uncontrolled asthma if at least one of the following apply (Eur. Respir. J. 2014; 43:343-73):

1. Poor symptom control: ACQ score consistently ≥1.5 or ACT score<20 (or "not well controlled" according to the NEAPP/GINA guideline);
2. Frequent severe exacerbations: twice or more bursts (≥3 days each) of systemic steroid agents in the previous year;
3. Serious exacerbations: at least one hospitalization, ICU stay, or mechanical ventilation in the previous year; and
4. Airflow limitation: FEV1 of <80% predicted (FEV1/FVC defined as less than the lower limit of normal) following a withhold of bronchodilators.

Furthermore, asthma which is controlled by high-dose ICS or a systemic steroid agent (or addition of a biological formulation) but worsens on gradual reduction of the dose, is also included (also defined as severe asthma).

The number of asthma patients in Japan is said to be approximately 8,000,000, and approximately 5% of them, which means approximately 400,000 patients, are presumed to be refractory asthma patients. Meanwhile, the number of asthma patients in the world is said to be approximately 300,000,000, and approximately 5 to 10% of them are presumed to be refractory asthma patients.

Regarding effects of an IL-6 receptor antibody on animal models of asthma, it has been reported that administering MR16-1 to neutrophilic asthma models resulted in improvement of airway hyperresponsiveness (NPL 1: The Journal of Immunology, 2013, 190:1056-1065), administering an IL-6R antibody to mouse models of allergic asthma resulted in disappearance of allergic traits (NPL 2: Scientific Reports 3, Article number: 1754 (2013)), and administration of IL-6-specific neutralization antibodies to mice carrying a mutation at position 576 in the α-chain of the IL-4 receptor inhibited differentiation of naive T cells (Th0 cells) into Th17 cells to provide protection of airways from severe inflammation (NPL 3: Nat Med. 2016 September; 22(9): 1013-22. Doi: 10.1038/nm. 4147. Epub 2016 Aug. 1). It has been further reported that airway hyperresponsiveness was improved in IL-6KO mice (NPL 4: Journal of Molecular Medicine, January 2016, vol 94, Issue 1, pp 51-59).

Furthermore, as for effects on humans, it has been reported that the IL-6 concentration is significantly high in the blood and expectoration of severe refractory asthma patients and obese asthma patients (NPL 5: Lancet Respir Med 2016; 4(7):574-84); large amounts of inflammatory cytokines (including IL-6) are produced from white adipocytes in tissues of obese asthma patients, particularly female patients (NPL 6: Am J Respir Crit Care Med. 2012; 186(7): 598-605; Rev Port Pneumol. 2016; 22(5):255-61); and IL-6R mRNA level and IL-6 protein level are high in the expectoration of severe asthma patients (Clin Exp Allergy, 2018 Jan. 6. doi: 10.1111/cea.13085). Furthermore, increased level of IL-6 expression was reported in the fibroblasts of severe asthma patients and mild asthma patients compared to healthy individuals (Cellular Signaling 43 (2018) 47-54). In addition, information on a clinical trial aimed at confirming the effects of tocilizumab (anti-IL-6 receptor antibody) on mild to moderate atopic asthma (Trial ID: ACTRN12614000123640) (NPL 7: anzctr.org.au/Trial/Registration/TrialReview.aspx?id=365668; NPL 8: qimrberghofer edu.au/_our-research/participate-in-our-re-search/clinical-trial-asthma/), and information on a clinical trial aimed at confirming the effects of sirukumab (anti-IL-6 antibody) on asthma (Clinical Trials.gov Identifier: NCT02794519) (NPL 9: clinicaltrials.gov/ct2/show/NCT02794519) have been disclosed.

However, none of the above-mentioned documents show that administration of an IL-6 inhibitor to humans results in improvement of asthma. Furthermore, the above-mentioned clinical trial for sirukumab has been cancelled before patient registration.

Furthermore, IL-6 has been reported to inhibit aeroallergen-induced responses, since increase in Th2-type cytokine production, eosinophils, and inflammation in tissues and bronchoalveolar lavage (BAL) fluid were observed in IL-6 deficient mice, but were inhibited in mice with overexpression of IL-6 in the airway (NPL 10: J Immunol Oct. 1, 2000, 165(7)4051-4061).

CITATION LIST

Non-Patent Literature

[NPL 1] The Journal of Immunology, 2013, 190:1056-1065

[NPL 2] Scientific Reports 3, Article number: 1754 (2013)

[NPL 3] Nat Med. 2016 September; 22(9):1013-22. Doi: 10.1038/nm. 4147. Epub 2016 Aug. 1.

[NPL 4] Journal of Molecular Medicine, January 2016, vol 94, Issue 1, pp 51-59

[NPL 5] Lancet Respir Med 2016; 4(7):574-84

[NPL 6] Am J Respir Crit Care Med. 2012; 186(7):598-605, Rev Port Pneumol. 2016; 22(5):255-61

[NPL 7] www anzctr.org.au/Trial/Registration/TrialReview.aspx?id=365668

[NPL 8] www qimrberghofer.edu.au/our-research/partici-pate-in-our-research/clinical-trial-asthma/

[NPL 9] https:clinicaltrials.gov/ct2/show/NCT02794519

[NPL 10] J Immunol Oct. 1, 2000, 165(7)4051-4061

SUMMARY OF INVENTION

Technical Problem

The present invention was achieved in view of the above circumstances. An objective of the present invention is to provide therapeutic agents for asthma to be administered to humans.

Solution to Problem

As a result of dedicated research, the present inventors surprisingly found that inhibition of IL-6 leads to treatment of human asthma.

The present invention is based on such findings, and specifically provides following [1] to [28]:

[1] A therapeutic agent for human asthma comprising an IL-6 inhibitor as an active ingredient.

[2] The therapeutic agent of [1], which suppresses exacerbation.

[3] The therapeutic agent of [2], wherein the suppression of exacerbation is decrease in emergency medical consultation or unscheduled medical consultation.

[4] The therapeutic agent of any one of [1] to [3], wherein the asthma is severe asthma.

[5] The therapeutic agent of any one of [1] to [4], wherein the asthma is eosinophilic asthma, non-eosinophilic asthma, obese asthma, or aspirin-induced asthma.

[6] The therapeutic agent of any one of [1] to [5], wherein the asthma is non-eosinophilic asthma or obese asthma.

[7] The therapeutic agent of any one of [1] to [6], which improves QOL of a patient.

[8] The therapeutic agent of [7], wherein the improvement of QOL is decrease in emergency medical consultation or unscheduled medical consultation.

[9] The therapeutic agent of [8], wherein QOL is judged as being improved when the Asthma Control Test (ACT) score is 20 or greater.

[10] The therapeutic agent of any one of [1] to [9], which improves or maintains the controlled state of asthma.

[11] The therapeutic agent of any one of [1] to [9], which suppresses expression of an asthmatic symptom (coughing, wheezing, expectoration, and/or dyspnea).

[12] The therapeutic agent of any one of [1] to [11], which enables reduction in the amount of steroid use.

[13] The therapeutic agent of any one of [1] to [12], which enables improvement of respiratory function.

[14] The therapeutic agent of [13], wherein the respiratory function is Peak Expiratory Flow (PEF).

[15] The therapeutic agent of any one of [1] to [14], wherein the IL-6 inhibitor is an IL-6 receptor antibody or an IL-6 antibody.

[16] The therapeutic agent of [15], wherein the IL-6 receptor antibody or the IL-6 antibody is a human antibody, a humanized antibody, or a chimeric antibody.

[17] The therapeutic agent of [15] or [16], wherein the IL-6 receptor antibody is tocilizumab or an antibody that binds to the same epitope as tocilizumab.

[18] The therapeutic agent of any one of [15] to [17], wherein the IL-6 receptor antibody is an antibody comprising the heavy chain variable region of SEQ ID NO: 1 and the light chain variable region of SEQ ID NO: 2, or an antibody comprising the heavy chain variable region of SEQ ID NO: 5 and the light chain variable region of SEQ ID NO: 6.

[19] The therapeutic agent of any one of [15] to [17], wherein the IL-6 receptor antibody is an antibody comprising the heavy chain of SEQ ID NO: 3 and the light chain of SEQ ID NO: 4, or an antibody comprising the heavy chain of SEQ ID NO: 7 and the light chain of SEQ ID NO: 8.

[20] The therapeutic agent of any one of [1] to [19] characterized in that an effective amount of the IL-6 inhibitor is administered.

[21] The therapeutic agent of any one of [1] to [20], wherein the asthma is adult asthma.

[22] The therapeutic agent of any one of [1] to [21], wherein the asthma is asthma excluding severe childhood asthma carrying an IL-4R$^{576}$ mutation.

[23] The therapeutic agent of any one of [1] to [22], wherein the asthma is asthma in a patient with rheumatoid arthritis.

[24] The therapeutic agent of any one of [1] to [23], wherein the asthma is asthma in a patient with chronic rheumatoid arthritis.

[25] The therapeutic agent of any one of [1] to [24], which is administered in combination with an inhaled steroid.

[26] The therapeutic agent of any one of [1] to [25], which is administered in combination with an additional long-acting β2-agonist.

[27] The therapeutic agent of any one of [1] to [25], which is administered in combination with an additional long-acting control agent.

[28] The therapeutic agent of any one of [1] to [27], which is administered in combination with an additional systemic steroid.

The present invention also provides following [A] to [D].

[A] Use of an IL-6 inhibitor in the manufacture of a pharmaceutical composition for treating human asthma.

[B] Use of an IL-6 inhibitor in treating human asthma.

[C] A method for treating human asthma, comprising administering an IL-6 inhibitor to a subject who needs asthma treatment.

[D] A method for manufacturing a pharmaceutical composition for treating human asthma, comprising mixing an IL-6 inhibitor and a pharmaceutically acceptable carrier.

The present invention also provides following [E1] to [E22].

[E1] The use of [A] or [B], which is for suppressing exacerbation.

[E2] The use of [E1], wherein the suppression of exacerbation is decrease in unscheduled medical consultation or emergency medical consultation.

[E3] The use of [A], [B], [E1], or [E2], wherein the asthma is severe asthma.

[E4] The use of any one of [A], [B], and [E1] to [E3], wherein the asthma is eosinophilic asthma, non-eosinophilic asthma, obese asthma, or aspirin-induced asthma.

[E5] The use of any one of [A], [B], and [E1] to [E4], wherein the asthma is non-eosinophilic asthma or obese asthma.

[E6] The use of any one of [A], [B], and [E1] to [E5], which is for improving QOL of a patient.

[E7] The use of [E6], wherein the improvement of QOL is decrease in emergency medical consultation or unscheduled medical consultation.

[E8] The use of [E7], wherein QOL is judged as being improved when the Asthma Control Test (ACT) score is 20 or greater.

[E9] The use of any one of [A], [B], and [E1] to [E8], which is for improving or maintaining a controlled state of asthma.

[E10] The use of any one of [A], [B], and [E1] to [E9], which is for suppressing expression of an asthmatic symptom (coughing, wheezing, expectoration, and/or dyspnea).

[E11] The use of any one of [A], [B], and [E1] to [E10], which is for enabling reduction in the amount of steroid use.

[E12] The use of any one of [A], [B], and [E1] to [E11], which is for enabling improvement of respiratory function.

[E13] The use of [E12], wherein the respiratory function is Peak Expiratory Flow (PEF).

[E14] The use of any one of [A], [B], and [E1] to [E13], wherein the IL-6 inhibitor is an IL-6 receptor antibody or an IL-6 antibody.

[E15] The use of [E14], wherein the IL-6 receptor antibody or the IL-6 antibody is a human antibody, a humanized antibody, or a chimeric antibody.

[E16] The use of [E14] or [E15], wherein the IL-6 receptor antibody is tocilizumab or an antibody that binds to the same epitope as tocilizumab.

[E17] The use of any one of [E14] to [E16], wherein the IL-6 receptor antibody is an antibody comprising the heavy chain variable region of SEQ ID NO: 1 and the light chain variable region of SEQ ID NO: 2, or an antibody comprising the heavy chain variable region of SEQ ID NO: 5 and the light chain variable region of SEQ ID NO: 6.

[E18] The use of any one of [E14] to [E16], wherein the IL-6 receptor antibody is an antibody comprising the heavy chain of SEQ ID NO: 3 and the light chain of SEQ ID NO: 4, or an antibody comprising the heavy chain of SEQ ID NO: 7 and the light chain of SEQ ID NO: 8.

[E19] The use of any one of [A], [B], and [E1] to [E18] characterized in that an effective amount of an IL-6 inhibitor is administered.

[E20] The use of any one of [A], [B], and [E1] to [E19], wherein the asthma is adult asthma.

[E21] The use of any one of [A], [B], and [E1] to [E20], wherein the asthma is asthma excluding severe childhood asthma carrying an IL-4R576 mutation.

[E22] The use of any one of [A], [B], and [E1] to [E21], wherein the asthma is asthma in a patient with rheumatoid arthritis.

[E23] The use of any one of [A], [B], and [E1] to [E22], wherein the asthma is asthma in a patient with chronic rheumatoid arthritis.

Effects of the Invention

The present inventors succeeded in confirming therapeutic effects of the administration of IL-6 inhibitors on human asthma.

DESCRIPTION OF EMBODIMENTS

In the present invention, "asthma" and "bronchial asthma" have the same meaning. Examples of specific phenotypes of "asthma" and "bronchial asthma" include eosinophilic asthma, non-eosinophilic asthma, obese asthma, and aspirin-induced asthma.

In one aspect, a therapeutic agent of the present invention suppresses exacerbation. In the present invention, "exacerbation" means asthmatic symptom (coughing, expectoration, wheezing, and/or dyspnea) of a patient requiring (1) use of a systemic steroid for three or more days; (2) hospitalization; or (3) emergency medical consultation or unscheduled medical consultation. In the present invention, "suppression of exacerbation" means decreasing the frequency of exacerbations. Suppression of exacerbation does not necessarily require complete prevention of exacerbation development, and it is sufficient if exacerbation frequency is decreased compared to that when a therapeutic agent of the present invention is not used.

In another aspect, a therapeutic agent of the present invention improves the QOL of asthma patients. In the present invention, "improvement of QOL" is evaluated by the frequency of emergency medical consultations or unscheduled medical consultations, bronchial asthmatic symptoms, respiratory function, asthma control test (ACT), asthma control questionnaire (ACQ), asthma quality of life questionnaire (AQLQ), and/or St. George's Respiratory Questionnaire (SGRQ), etc.

In one embodiment, improvement of QOL is indicated by decrease in the frequency of emergency medical consultations or unscheduled medical consultations.

In another embodiment, improvement of QOL is indicated, for example by the Asthma Control Test (ACT) score of 20 to 25. In another embodiment, improvement of QOL is indicated by improvement of respiratory functions. In the present invention, "improvement of respiratory functions" means, for example, improvement of FEV1 or PEF.

In another aspect, a therapeutic agent of the present invention improves or maintains a controlled state of asthma. In the present invention, "improves or maintains a controlled state of asthma" means that expression of (bronchial) asthmatic symptoms (coughing, expectoration, wheezing, and/or dyspnea) is suppressed, and daily lives can be led without problems.

In another aspect, IL-6 inhibitors treat severe asthma. In the present invention, "severe asthma" and "refractory asthma" have the same meaning, and the both means asthma that requires administration of high dose inhaled corticosteroid (ICS) (in terms of fluticasone propionate, 500 μg/day or more (according to the GINA guideline) or 800 μg/day or more (according to the Japanese guideline (JGL)) plus a long-acting control agent (multiple pharmaceutical agents selected from long-acting β2-agonists, leukotriene receptor antagonists, controlled-release theophylline formulations, long-acting anticholinergics, oral steroid agents, anti-IgE antibodies, anti-IL-5 antibodies, and such) for controlling asthmatic symptoms, or asthma of which asthmatic symptoms remain uncontrolled despite such treatments. Here, the aforementioned "uncontrolled" means no improvement of (bronchial) asthmatic symptoms (coughing, expectoration, wheezing, and/or dyspnea).

Alternatively, "severe asthma" means severe asthma as defined by the ERS/ATS severe asthma guidelines.

That is, in addition to the above, "severe asthma" and "refractory asthma" in the present invention include asthma described in any one of following (1) to (4):

(1) asthma that required treatment suggested for asthma of Global Initiative for Asthma (GINA) guideline steps 4-5 (high-dose ICS plus LABA or LTRA/theophylline agent) for the previous year to prevent it from becoming "uncontrolled" (here, "high-dose ICS plus LABA or LTRA/theophylline agent" means combination of one or more pharmaceutical agents selected from LABA, LTRA, and theophylline with high-dose ICS);

(2) asthma for which the number of days requiring systemic steroid agents reached 50% or more than that of the previous year;

(3) asthma which remains "uncontrolled" despite the treatments described above in (1) and (2), wherein the asthma is regarded as "uncontrolled" if at least one of the following apply:

1. Poor symptom control: ACQ score consistently ≥1.5, and/or ACT score<20 (or "not well controlled" according to the NEAPP/GINA guideline);

2. Frequent severe exacerbations: two or more bursts of systemic steroid agents (≥3 days each) in the previous year;

3. Serious exacerbations: at least one hospitalization, ICU stay, or mechanical ventilation in the previous year; and 4. Airflow limitation: FEV1 of less than 80% predicted (FEV1/FVC defined as less than the lower limit of normal) following a withhold of bronchodilators; and (4) asthma in patients with asthma which is controlled by high-dose ICS or systemic steroid agent (or addition of a biological formulation), but worsens on gradual reduction of the dose.

Examples of the inhaled steroids (inhaled corticosteroids (ICS)) include fluticasone propionate, budesonide, and ciclesonide; examples of long-acting β2-agonist (LABA) include salmeterol xinafoate, tulobuterol, and formoterol fumaric acid hydrate; examples of leukotriene receptor antagonists (LTRA) include montelukast sodium and pranlukast hydrate; an example of a long-acting anticholinergic agent (long-acting muscarinic antagonist (LAMA)) is tiotropium bromide hydrate; an example of oral steroids (oral corticosteroids (OCS)) is prednisolone; an example of an anti-IgE antibody is omalizumab; and an example of an anti-IL-5 antibody is mepolizumab, but are not limited thereto.

Examples of other therapeutic agents for asthma include short-acting β2-agonists (SABA) and IL-5R antibodies. Examples of SABA include procaterol hydrochloride hydrate, salbutamol sulfate, and terbutaline sulfate, and an example of IL-5R antibody is benralizumab.

Specific examples of "severe asthma" and "refractory asthma" include non-eosinophilic asthma, obese asthma, and aspirin-induced asthma.

In the present invention, "eosinophilic asthma" means asthma with strong eosinophilic airway inflammation. Generally, in patients with eosinophilic asthma, the proportion of eosinophils in the expectoration is high, or the number of eosinophils in the peripheral blood is high (Nat. Med. 2012 May 4, 18(5):716-25; N. Engl. J. Med. 2017 Sep. 7, 377 (10):965-976; J. Asthma Allergy. 2014 Apr. 11, 7:53-65; Ann. Am. Thorac. Soc. 2013 December, 10 Suppl: S143-9; and Clin. Exp. Allergy. 2017 February, 47(2):161-175). Specific examples of eosinophilic asthma include asthma in patients whose percentage of the number of eosinophils relative to all white blood cells in the expectoration is 2% or more, whose percentage of the number of eosinophils relative to all white blood cells in the expectoration is 3% or more, and whose number of eosinophils in the peripheral blood is 300/μL or more. Other specific examples of eosinophilic asthma include, but are not limited to, asthma in which the proportion of the number of eosinophils relative to all white blood cells in the peripheral blood is 5% or more.

In the present invention "non-eosinophilic asthma" means asthma other than eosinophilic asthma.

In the present invention, "obese asthma" means asthma in patients whose BMI values are 25 kg/m2 or more. More specifically, it means asthma in Japanese asthma patients whose BMI values are 25 kg/m2 or more, and European and American asthma patients whose BMI values are 30 kg/m2 or more.

For example, the therapeutic agent of the present invention was confirmed to be effective for a subject having BMI of 27.9. Therefore, therapeutic effects of the therapeutic agent of the present invention on obese asthma was confirmed.

In one aspect, therapeutic agents of the present invention may be administered to asthma patients whose IL-6 is above normal level in the blood, expectoration, airway secretory fluid, or bronchoalveolar lavage (BAL) fluid.

In another aspect, therapeutic agents of the present invention may be administered to asthma patients whose blood C-reactive protein (CRP) is above normal level. IL-6 stimulates the acute-phase response in the liver, and this results in increased CRP production and higher serum CRP level. For this reason, C-reactive protein (CRP) has been reported to serve as a surrogate marker for IL-6 activity. Blood CRP concentration can be measured easily, for example, by ELISA.

The present invention involves selecting severe asthma patients based on the above-mentioned criteria and provides IL-6 inhibitors for administration to the selected patients. Alternatively, the present invention provides methods for treating severe asthma, which comprises the steps of selecting severe asthma patients based on the above-mentioned criteria and administering IL-6 inhibitors to the selected patients. Furthermore, the present invention involves selecting severe asthma patients based on the above-mentioned criteria, and relates to uses of an IL-6 inhibitor in the manufacture of a pharmaceutical composition for administration to those selected patients.

In the present invention, the asthma can be regarded as severe asthma when it satisfies at least one of the criteria selected from the following:

(1) asthma which requires administration of a combination of high-dose ICS and long-acting control agents to control its symptoms, or asthma which remains uncontrolled despite such treatment;

(2) asthma that required high-dose ICS plus one or more pharmaceutical agents selected from LABA, LTRA, and theophylline, for the previous year;

(3) asthma for which the number of days requiring a systemic steroid agent reached 50% or more than that of the previous year;

(4) asthma which remains "uncontrolled" despite the treatment described in (2) or (3), wherein asthma in patients for which at least one of the following conditions apply:

1. Poor symptom control: ACQ score consistently ≥1.5, and/or ACT score<20 (or "not well controlled" according to the NEAPP/GINA guideline);

2. Frequent severe exacerbations: two or more bursts of systemic steroid agents (≥3 days each) in the previous year;

3. Serious exacerbations: at least one hospitalization, ICU stay, or mechanical ventilation in the previous year; and 4. Airflow limitation: FEV1 of less than 80% predicted (FEV1/FVC defined as less than the lower limit of normal) following a withhold of bronchodilators; and (5) asthma in patients with asthma which is controlled by high-dose ICS plus one or more pharmaceutical agents selected from systemic steroid agents and biological formulations, but worsens on gradual reduction of the dose.

Examples of the high-dose ICS in (1) of the above-mentioned criteria include doses of 500 μg/day or more (according to the GINA guideline) or 800 μg/day or more (according to the Japanese guideline (JGL)), converted into terms of fluticasone propionate. Furthermore, in the present invention, long-acting control agents may indicate two or more pharmaceutical agents selected from the group consisting of long-acting β2-agonist (LABA), leukotriene receptor antagonists (LTRA), controlled-release theophylline formulations, long-acting anticholinergics (LAMA), oral steroid agents (OCS), anti-IgE antibodies, anti-IL-5 antibodies, and anti-IL-5 receptor antibodies. High-dose ICS in (2) and (5) of the above-mentioned criteria means 500 μg/day or more (according to the ERS/ATS severe asthma guidelines), converted into terms of fluticasone propionate. Furthermore, "ICS plus one or more pharmaceutical agents selected from LABA, LTRA, and theophylline" in (2) of the above-mentioned criteria means use of one or more pharmaceutical agents selected from LABA, LTRA, and theophylline, in addition to ICS. "ICS plus one or more pharmaceutical agents selected from systemic steroid agents and biological formulations" in (5) of the above-mentioned criteria means use of a systemic steroid agent or a biological formulation or both, in addition to ICS.

In certain embodiments, severe asthma patients of the present invention do not include patients already receiving IL-6 inhibitors for treatment of rheumatoid. That is, the present invention may include the step of selecting severe asthma patients based on the above-mentioned criteria, from asthma patients who have not received IL-6 inhibitor administration.

In one aspect, the therapeutic agent of the present invention may be formulated as a unit dosage form containing an effective amount of an IL-6 inhibitor. Herein, "effective amount" refers to an amount at the necessary dose and over the necessary period that is effective for achieving the desired therapeutic result.

The times the therapeutic agent of the present invention is administered can be appropriately determined according to the condition of the subject receiving the administration, the administration method, and such. The therapeutic agent of the present invention is administered, for example, once to four times a week.

Therapeutic agents of the present invention are intended to be administered to humans.

Therapeutic agents of the present invention comprise an IL-6 inhibitor as an active ingredient.

"IL-6 inhibitors" of the present invention are substances that block signal transduction by IL-6, and inhibit the biological activities of IL-6. IL-6 inhibitors are preferably substances that have inhibitory effects against binding to any one of IL-6, IL-6 receptor, and gp130.

Examples of an IL-6 inhibitor of the present invention include, but are not particularly limited to, anti-IL-6 antibodies, anti-IL-6 receptor antibodies, anti-gp130 antibodies, IL-6 variants, soluble IL-6 receptor variants, or partial peptides of IL-6 or IL-6 receptor, and low-molecular-weight substances showing a similar activity. Examples of an IL-6 inhibitor of the present invention may be preferably IL-6 receptor-recognizing antibodies.

IL-6 transmits its biological activity via two types of proteins on cells. One of them is the IL-6 receptor, which is a ligand-binding protein that has a molecular weight of approximately 80 kD to which IL-6 binds (NPLs 4 and 5). The IL-6 receptor exists as a soluble IL-6 receptor, which is mainly composed of its extracellular region, in addition to a membrane-bound form expressed on the cell membrane and penetrates through the cell membrane.

The other one is non-ligand-binding membrane protein gp130, which has a molecular weight of about 130 kDa and is involved in signal transduction. The biological activity of IL-6 is transmitted into a cell through formation of an IL-6/IL-6 receptor complex by IL-6 and the IL-6 receptor, followed by binding of the complex with gp130 (Taga, T. et al, Cell (1989) 58, 573-581).

IL-6 inhibitors are substances that inhibit the transmission of IL-6 biological activity. So far, antibodies against IL-6 (anti-IL-6 antibodies), antibodies against the IL-6 receptor (anti-IL-6 receptor antibodies), antibodies against gp130 (anti-gp130 antibodies), IL-6 variants, partial peptides of IL-6 or the IL-6 receptor, and such have been known.

The origin of the antibodies of the present invention is not particularly limited, but it is preferably a mammal and more preferably human.

An anti-IL-6 antibody used in the present invention can be obtained as either a polyclonal or monoclonal antibody using known methods. A monoclonal antibody derived from a mammal is particularly preferred for the anti-IL-6 antibody used in the present invention. The monoclonal antibodies derived from a mammal include those produced by a hybridoma and those produced by a host transformed with an expression vector containing an antibody gene using genetic engineering methods. By binding to IL-6, this antibody inhibits the binding of IL-6 to an IL-6 receptor, and blocks transduction of the IL-6 biological activity into cells.

Examples of such an antibody include the MH166 antibody (Matsuda, T. et al., Eur. J. Immunol. (1988) 18, 951-956) and the SK2 antibody (Sato, K. et al., The abstracts of the 21st Annual Meeting of the Japanese Society for Immunology (1991) 21, 166).

Basically, hybridomas that produce an anti-IL-6 antibody can be produced using known techniques as below. Specifically, the hybridomas can be produced by performing immunization by a conventional immunization method using IL-6 as a sensitizing antigen, fusing the resulting immune cells with known parent cells by a conventional cell fusion method, and then screening for cells that produce monoclonal antibodies using a conventional screening method.

Specifically, anti-IL-6 antibodies can be produced as below. Human IL-6 to be used as a sensitizing antigen for obtaining antibodies can be obtained by, for example, using the IL-6 gene/amino acid sequences disclosed in Eur. J. Biochem (1987) 168, 543-550; J. Immunol. (1988) 140, 1534-1541; and Agr. Biol. Chem. (1990) 54, 2685-2688.

After an appropriate host cell is transformed with a known expression vector system inserted with an IL-6 gene sequence, the target IL-6 protein is purified from the inside of the host cell or from the culture supernatant using a known method. This purified IL-6 protein may be used as a sensitizing antigen. Alternatively, a fusion protein of the IL-6 protein and another protein may be used as a sensitizing antigen.

An anti-IL-6 receptor antibody used in the present invention can be obtained as either a polyclonal or monoclonal antibody using known methods. A monoclonal antibody derived from a mammal is particularly preferred for the anti-IL-6 receptor antibody used in the present invention. The monoclonal antibodies derived from a mammal include those produced by a hybridoma and those produced by a host transformed with an expression vector containing an antibody gene using genetic engineering methods. By binding to an IL-6 receptor, this antibody inhibits the binding of IL-6 to an IL-6 receptor, and blocks transduction of the IL-6 biological activity into cells.

Examples of such an antibody include the MR16-1 antibody (Tamura, T. et al. Proc. Natl. Acad. Sci. USA (1993) 90, 11924-11928), PM-1 antibody (Hirata, Y. et al., J. Immunol. (1989) 143, 2900-2906), AUK12-20 antibody, AUK64-7 antibody, and AUK146-15 antibody (International Patent Application Publication No. WO 92-19759). Among them, the PM-1 antibody is listed as an example of a preferred monoclonal antibody against the human IL-6 receptor, and the MR16-1 antibody is listed as an example of a preferred monoclonal antibody against the mouse IL-6 receptor.

Basically, hybridomas that produce an anti-IL-6 receptor monoclonal antibody can be produced using known techniques as below. Specifically, the hybridomas can be produced by performing immunization by a conventional immunization method using an IL-6 receptor as a sensitizing antigen, fusing the resulting immune cells with known parent cells by a conventional cell fusion method, and then screening for cells that produce monoclonal antibodies using a conventional screening method.

Specifically, anti-IL-6 receptor antibodies can be produced as below. A human IL-6 receptor or mouse IL-6 receptor to be used as a sensitizing antigen for obtaining antibodies can be obtained by, for example, using the IL-6 receptor gene and/or amino acid sequences respectively disclosed in European Patent Application Publication No. EP 325474 and Japanese Patent Application Kokai Publication No. (JP-A) H03-155795 (unexamined, published Japanese patent application).

There are two types of IL-6 receptor proteins: one expressed on the cell membrane and the other separated from the cell membrane (soluble IL-6 receptor) (Yasukawa, K. et al., J. Biochem. (1990) 108, 673-676). The soluble IL-6 receptor is essentially composed of the extracellular region of the IL-6 receptor bound to the cell membrane, and differs from the membrane-bound IL-6 receptor in that it lacks the transmembrane region or both the transmembrane and intracellular regions. Any IL-6 receptor may be employed as the IL-6 receptor protein, as long as it can be used as a sensitizing antigen for producing an anti-IL-6 receptor antibody to be used in the present invention.

After an appropriate host cell is transformed with a known expression vector system inserted with an IL-6 receptor gene sequence, the target IL-6 receptor protein is purified from the inside of the host cell or from the culture supernatant using a known method. This purified IL-6 receptor protein may be used as a sensitizing antigen. Alternatively, a cell expressing the IL-6 receptor or a fusion protein of the IL-6 receptor protein and another protein may be used as a sensitizing antigen.

An anti-gp130 antibody used in the present invention can be obtained as either a polyclonal or monoclonal antibody using known methods. A monoclonal antibody derived from a mammal is particularly preferred for the anti-gp130 antibody used in the present invention. The monoclonal antibodies derived from a mammal include those produced by a hybridoma and those produced by a host transformed with an expression vector containing an antibody gene using a genetic engineering method. By binding to gp130, this antibody inhibits the binding of an IL-6/IL-6-receptor complex to gp130, and blocks transduction of the IL-6 biological activity into cells.

Examples of such an antibody include the AM64 antibody (JP-A (Kokai) H03-219894), 4B11 and 2H4 antibodies (U.S. Pat. No. 5,571,513), and the B-S12 and B-P8 antibodies (JP-A (Kokai) H08-291199).

Basically, hybridomas that produce an anti-gp130 monoclonal antibody can be produced using known techniques as below. Specifically, the hybridomas can be produced by performing immunization by a conventional immunization method using gp130 as a sensitizing antigen, fusing the resulting immune cells with known parent cells by a conventional cell fusion method, and then screening for cells that produce monoclonal antibodies using a conventional screening method.

Specifically, the monoclonal antibodies can be produced as below. For example, gp130 to be used as a sensitizing antigen for obtaining antibodies can be obtained by using the gp130 gene and/or amino acid sequences disclosed in European Patent Application Publication No. EP 411946.

After an appropriate host cell is transformed with a known expression vector system inserted with a gp130 gene sequence, the target gp130 protein is purified from the inside of the host cell or from the culture supernatant using a known method. This purified gp130 protein may be used as a sensitizing antigen. Alternatively, a gp130-expressing cell or a fusion protein of the gp130 protein and another protein may be used as a sensitizing antigen.

Mammals to be immunized with a sensitizing antigen are not particularly limited, but are preferably selected in consideration of the compatibility with parent cells used for cell fusion. Typically, rodents such as mice, rats, and hamsters are used.

Animals are immunized with a sensitizing antigen according to known methods. Typically, immunization is performed by, for example, intraperitoneal or subcutaneous injection of the sensitizing antigen to a mammal. Specifically, it is preferable to dilute or suspend the sensitizing antigen in Phosphate-Buffered Saline (PBS), physiological saline, and such, to an appropriate volume, and mix it with an appropriate amount of a conventional adjuvant such as Freund's complete adjuvant if desired and emulsify, and then administer to the mammal every four to 21 days for several times. An appropriate carrier may also be used for immunization with the sensitizing antigen.

After immunizing the mammal in this manner, and confirming that the serum level of a desired antibody has increased, immunized cells are removed from the mammal and subjected to cell fusion. Spleen cells are particularly preferred as the immunized cells to be subjected to cell fusion.

Myeloma cells from mammals are used as parent cells to be fused with the immunized cells. So far, various known cell lines such as P3X63Ag8.653 (Kearney, J. F. et al., J. Immunol (1979) 123, 1548-1550), P3X63Ag8U.1 (Current Topics in Microbiology and Immunology (1978) 81, 1-7), NS-1 (Kohler, G. and Milstein, C., Eur. J. Immunol. (1976) 6, 511-519), MPC-11 (Margulies, D. H. et al., Cell (1976) 8, 405-415), SP2/0 (Shulman, M. et al., Nature (1978) 276, 269-270), FO (de St. Groth, S. F. et al., J. Immunol. Methods (1980) 35, 1-21), 5194 (Trowbridge, I. S., J. Exp. Med. (1978) 148, 313-323), and 8210 (Galfre, G. et al., Nature (1979) 277, 131-133) are suitably used.

Basically, cell fusion of the aforementioned immune cells with myeloma cells can be performed according to known methods such as the method of Milstein et al. (Kohler, G. and Milstein, C., Methods Enzymol. (1981) 73, 3-46).

More specifically, the cell fusion is performed, for example, in a conventional nutrient culture medium in the presence of a cell fusion promoter. For example, polyethylene glycol (PEG) or Sendai virus (HVJ) is used as the fusion promoter, and if desired, an adjuvant such as dimethyl sulfoxide can be further added for use in improving the fusion efficiency.

The ratio of immune cells to myeloma cells used is preferably, for example, 1 to 10 immune cells for each myeloma cell. The culture medium used for the cell fusion is, for example, an RPMI1640 or MEM culture medium suitable for the proliferation of the myeloma cell lines. Other conventional culture media used for this type of cell culture can also be used. Furthermore, serum supplements such as fetal calf serum (FCS) can also be used in combination.

For cell fusion, the fusion cells (hybridomas) of interest are formed by thoroughly mixing predetermined amounts of the aforementioned immune cell and myeloma cell in the aforementioned culture medium, adding a PEG solution (for example, a solution of PEG with an average molecular weight of about 1,000 to 6,000) pre-heated to about 37° C., usually at a concentration of 30% to 60% (w/v), and then mixing them. Then, cell fusion agents and such that are unsuitable for the growth of hybridomas can be removed by repeating the operation of sequentially adding an appropriate culture medium and removing the supernatant by centrifugation.

The hybridomas are selected by culturing in a general selection culture medium, for example, the HAT culture medium (a culture medium containing hypoxanthine, aminopterin, and thymidine). Culturing in the HAT culture medium is continued for a sufficient period, generally from several days to several weeks, to kill cells other than the hybridomas of interest (unfused cells). Then, a standard limiting dilution method is performed to screen for and clone hybridomas that produce an antibody of interest.

Besides obtaining the hybridomas by immunizing non-human animals with an antigen, desired human antibodies having a binding activity to a desired antigen or antigen-expressing cell can be obtained by sensitizing a human lymphocyte with a desired antigen protein or antigen-expressing cell in vitro, and fusing the sensitized B lymphocyte with a human myeloma cell such as U266 (see, Japanese Patent Application Kokoku Publication No. (JP-B) H01-59878 (examined, approved Japanese patent application published for opposition)). Further, an antigen or antigen-expressing cell may be administered to a transgenic animal having a repertoire of human antibody genes, and then a desired human antibody may be obtained following the aforementioned method (see, International Patent Application Publication Nos. WO 93/12227, WO 92/03918, WO 94/02602, WO 94/25585, WO 96/34096, and WO 96/33735).

The hybridomas prepared as such that produce monoclonal antibodies can be subcultured in a conventional culture medium and stored in liquid nitrogen for a long period.

To obtain monoclonal antibodies from the hybridomas, the following methods may be employed: culturing the hybridomas according to conventional methods and obtaining the antibodies as a culture supernatant or proliferating the hybridomas by administering them to a compatible mammal and obtaining the antibodies from ascites; and so on. The former method is suitable for obtaining antibodies with high purity, and the latter is suitable for large-scale antibody production.

For example, hybridomas that produce anti-IL-6 receptor antibodies can be prepared by the method disclosed in JP-A (Kokai) H03-139293. Such a preparation can be carried out by injecting hybridomas that produce PM-1 antibodies into the abdominal cavity of a BALB/c mouse, obtaining ascites, and then purifying the PM-1 antibodies from the ascites; or by culturing the hybridomas in an appropriate medium (such as an RPMI 1640 medium containing 10% fetal bovine serum, and 5% BM-Condimed H1 (Boehringer Mannheim); the hybridoma SFM medium (GIBCO-BRL); or the PFHM-II medium (GIBCO-BRL)) and then purifying the PM-1 antibodies from the culture supernatant.

Recombinant antibodies can be used as the monoclonal antibodies of the present invention, wherein the recombinant antibodies are produced using genetic recombination techniques by cloning an antibody gene from a hybridoma, inserting the gene into an appropriate vector, and then introducing the vector into a host (see, for example, Borrebaeck, C. A. K. and Larrick, J. W., THERAPEUTIC MONOCLONAL ANTIBODIES, Published in the United Kingdom by MACMILLAN PUBLISHERS LTD, 1990).

More specifically, mRNAs coding for antibody variable (V) regions are isolated from cells that produce antibodies of interest, such as hybridomas. mRNAs can be isolated by preparing total RNAs according to known methods, such as the guanidine ultracentrifugation method (Chirgwin, J. M. et al., Biochemistry (1979) 18, 5294-5299) and the AGPC method (Chomczynski, P. et al., Anal. Biochem. (1987) 162, 156-159), and preparing mRNAs using an mRNA Purification Kit (Pharmacia) and such. Alternatively, mRNAs can be directly prepared using the QuickPrep mRNA Purification Kit (Pharmacia).

cDNAs of the antibody V regions are synthesized from the obtained mRNAs using reverse transcriptase. cDNAs may be synthesized using the AMV Reverse Transcriptase First-strand cDNA Synthesis Kit and such. Further, to synthesize and amplify the cDNAs, the 5'-RACE method (Frohman, M. A. et al., Proc. Natl. Acad. Sci. USA (1988) 85, 8998-9002; Belyaysky, A. et al., Nucleic Acids Res. (1989) 17, 2919-2932) using 5'-Ampli FINDER RACE Kit (Clontech) and PCR may be used. A DNA fragment of interest is purified from the obtained PCR products and then ligated with a vector DNA. Then, a recombinant vector is prepared by using the above, and introduced into *Escherichia coli* and such, and then its colonies are selected to prepare a desired recombinant vector. The nucleotide sequence of the DNA of interest is confirmed by a known method such as the dideoxy method.

When a DNA encoding the V region of the antibody of interest is obtained, the DNA is ligated with a DNA encoding the constant region (C region) of a desired antibody, and inserted into an expression vector. Alternatively, a DNA encoding an antibody V region may be inserted into an expression vector comprising a DNA of an antibody C region.

To produce an antibody to be used in the present invention, an antibody gene is inserted into an expression vector such that it is expressed under the control of an expression-regulating region such as an enhancer and promoter, as described below. Then, the antibody can be expressed by transforming a host cell with this expression vector.

In the present invention, artificially modified recombinant antibodies, for example, chimeric antibodies, humanized antibodies, or human antibodies can be used, for example, to reduce heteroantigenicity against humans. These modified antibodies can be prepared using known methods.

A chimeric antibody can be obtained by ligating a DNA encoding an antibody V region obtained as above with a DNA encoding a human antibody C region, inserting it into an expression vector, and introducing the vector into a host to produce the chimeric antibody (see, European Patent Application Publication No. EP 125023; International Patent Application Publication No. WO 92-19759). This known method can be used to obtain chimeric antibodies useful for the present invention.

Humanized antibodies are also referred to as reshaped human antibodies or antibodies made into the human type. They are produced by transplanting the complementarity determining regions (CDRs) of an antibody from a non-human mammal (for example, a mouse) into the CDRs of a human antibody. General methods for this gene recombination are also known (see, European Patent Application Publication No. EP 125023, International Patent Application Publication No. WO 92-19759).

More specifically, DNA sequences designed to ligate the CDRs of a mouse antibody with the framework regions (FRs) of a human antibody are synthesized by PCR from several oligonucleotides produced to contain overlapping portions at their termini. The obtained DNA is ligated with a DNA encoding a human antibody C region and inserted into an expression vector, and the expression vector is introduced into a host to produce the humanized antibody (see, European Patent Application Publication No. EP 239400, International Patent Application Publication No. WO 92-19759).

Human antibody FRs to be ligated via the CDRs are selected so that the CDRs form satisfactory antigen binding sites. The amino acid(s) within the framework regions of the antibody variable regions may be substituted as necessary so that the CDRs of the reshaped human antibody form appropriate antigen binding sites (Sato, K. et al., Cancer Res. (1993) 53, 851-856).

Human antibody C regions are used for the chimeric and humanized antibodies. Examples of human antibody C regions include Cγ, and for example, Cγ1, Cγ2, Cγ3, or Cγ4 may be used. Furthermore, to improve the stability of the antibodies or their production, the human antibody C regions may be modified.

Chimeric antibodies are composed of the variable region of an antibody derived from a non-human mammal and the C region derived from a human antibody; and humanized antibodies are composed of the CDRs of an antibody derived from a non-human mammal and the framework regions and C regions derived from a human antibody. Their antigenicity in the human body is reduced, and thus they are useful as antibodies for use in the present invention.

Preferred specific examples of humanized antibodies for use in the present invention include a humanized PM-1 antibody (see, International Patent Application Publication No. WO 92-19759).

Furthermore, in addition to the aforementioned methods for obtaining human antibodies, techniques for obtaining human antibodies by panning using a human antibody library are also known. For example, the variable region of a human antibody can be expressed on a phage surface as a single chain antibody (scFv) by using the phage display method, and antigen-binding phages can then be selected. By analyzing the genes of the selected phages, the DNA sequence encoding the variable region of the human antibody which binds to the antigen can be determined. Once the DNA sequence of an scFv which binds to the antigen is revealed, an appropriate expression vector comprising the sequence can be prepared to obtain a human antibody. These methods are already known, and the publications, WO 92/01047, WO 92/20791, WO93/06213, WO 93/11236, WO 93/19172, WO 95/01438, and WO 95/15388, can be used as references.

The antibody gene constructed as described above can be expressed according to known methods. When a mammalian cell is used, the antibody gene can be expressed by using a DNA in which a commonly used effective promoter gene, the antibody gene to be expressed, and a poly A signal on the 3' side (downstream) of the antibody gene are operatively linked together, or by using a vector comprising the DNA. Examples of a promoter/enhancer include the human cytomegalovirus immediate early promoter/enhancer.

Furthermore, other promoters/enhancers that can be used for expressing the antibodies for use in the present invention include viral promoters/enhancers from retroviruses, polyoma viruses, adenoviruses, simian virus 40 (SV40), and such; and mammalian cell-derived promoters/enhancers such as human elongation factor 1α (HEF1α).

The expression can be easily performed, for example, by following the method in Mulligan et al. (Mulligan, R. C. et al., Nature (1979) 277, 108-114) when using the SV40 promoter/enhancer, or by following the method in Mizushima et al. (Mizushima, S. and Nagata S., Nucleic Acids Res. (1990) 18, 5322) when using the HEF1α promoter/enhancer.

When *E. coli* is used, the antibody gene can be expressed by operatively linking a commonly used effective promoter gene, a signal sequence for antibody secretion, and the antibody gene to be expressed. Examples of the promoter include a lacZ promoter and an araB promoter. A lacZ promoter can be used according to the method of Ward et al. (Ward, E. S. et al., Nature (1989) 341, 544-546; Ward, E. S. et al., FASEB J. (1992) 6, 2422-2427); and an araB promoter can be used according to the method of Better et al. (Better, M. et al., Science (1988) 240, 1041-1043).

When the antibody is produced into the periplasm of *E. coli*, the pel B signal sequence (Lei, S. P. et al., J. Bacteriol. (1987) 169, 4379-4383) may be used as a signal sequence for antibody secretion. The antibody produced into the periplasm is isolated, and then appropriately refolded the antibody structure to be used (see, for example, WO 96/30394).

As the replication origin, those derived from SV40, polyoma virus, adenovirus, bovine papilloma virus (BPV) and such may be used. In addition, to increase the gene copy number in a host cell system, the expression vector may comprise the aminoglycoside phosphotransferase (APH) gene, thymidine kinase (TK) gene, *E. coli* xanthine-guanine phosphoribosyltransferase (Ecogpt) gene, dihydrofolate reductase (dhfr) gene, and such, as a selection marker.

Any production system may be used to prepare the antibodies for use in the present invention. The production systems for antibody preparation include in vitro and in vivo production systems. In vitro production systems include those using eukaryotic cells or those using prokaryotic cells.

When eukaryotic cells are used, the production systems include those using animal cells, plant cells, or fungal cells. Such animal cells include (1) mammalian cells such as CHO, COS, myeloma, baby hamster kidney (BHK), HeLa, and Vero; (2) amphibian cells such as *Xenopus* oocytes; and (3) insect cells such as sf9, sf21, and Tn5. Known plant cells include cells derived from *Nicotiana tabacum*, which may be cultured in callus. Known fungal cells include yeasts such as *Saccharomyces* (e.g., *Saccharomyces cerevisiae*) and mold fungi such as *Aspergillus* (e.g., *Aspergillus niger*).

When prokaryotic cells are used, production systems include those using bacterial cells. Known bacterial cells include *E. coli* and *Bacillus subtilis*.

Antibodies can be obtained by introducing the antibody gene of interest into these cells by transformation, and then culturing the transformed cells in vitro. Cells are cultured according to known methods. For example, DMEM, MEM, RPMI 1640, or IMDM may be used as the culture medium, and serum supplements such as fetal calf serum (FCS) may be used in combination. Alternatively, cells introduced with the antibody gene may be transferred into the abdominal cavity and such of an animal to produce the antibodies in vivo.

Meanwhile, in vivo production systems include those using animals or those using plants. When using animals, production systems include those using mammals or insects.

Mammals that can be used include goats, pigs, sheep, mice, and bovines (Vicki Glaser, SPECTRUM Biotechnology Applications, 1993). Further, insects that can be used include silkworms. When using plants, tobacco and such may be used.

An antibody gene is introduced into these animals or plants, and the antibodies are produced in the body of the animals or plants and then recovered. For example, an antibody gene can be prepared as a fusion gene by inserting it into the middle of a gene encoding a protein uniquely produced into milk, such as goat β casein. DNA fragments comprising the fusion gene, which includes the inserted antibody gene, are injected into goat embryos, and the embryos are introduced into female goats. The desired antibodies are obtained from milk produced by transgenic goats born from the goats that received the embryos, or their progenies. When appropriate, the transgenic goats may be given hormones to increase the volume of milk containing the desired antibodies that they produce (Ebert, K. M. et al., Bio/Technology (1994) 12, 699-702).

When silkworms are used, the silkworms are infected with a baculovirus inserted with the antibody gene of interest, and the desired antibodies are obtained from the body fluids of these silkworms (Maeda, S. et al., Nature (1985) 315, 592-594). Moreover, when tobacco is used, the antibody gene of interest is inserted into a plant expression vector such as pMON530, and the vector is introduced into bacteria such as *Agrobacterium tumefaciens*. This bacterium is used to infect tobacco such as *Nicotiana tabacum*, and then the desired antibody is obtained from the leaves of this tobacco (Julian, K.-C. Ma et al., Eur. J. Immunol. (1994) 24, 131-138).

When producing antibodies using in vitro or in vivo production systems as described above, DNAs encoding an antibody heavy chain (H chain) and light chain (L chain) may be inserted into separate expression vectors, and a host is then co-transformed with the vectors. Alternatively, the H chain-encoding DNA and L chain-encoding DNA may be inserted into a single expression vector for transforming a host (see International Patent Application Publication No. WO 94-11523).

The antibodies used in the present invention may be antibody fragments or modified products thereof, as long as they can be suitably used in the present invention. For example, antibody fragments include Fab, F(ab')2, Fv, and single chain Fv (scFv) in which the Fvs of the H and L chains are linked via an appropriate linker.

Specifically, the antibody fragments are produced by treating antibodies with enzymes such as papain or pepsin, or alternatively, by constructing genes encoding these antibody fragments and introducing them into expression vectors, and then expressing the vectors in appropriate host cells (see, for example, Co, M. S. et al., J. Immunol. (1994) 152, 2968-2976; Better, M. & Horwitz, A. H., Methods in Enzymology (1989) 178, 476-496; Plueckthun, A. & Skerra, A., Methods in Enzymology (1989) 178, 497-515; Lamoyi, E., Methods in Enzymology (1989) 121, 652-663; Rousseaux, J. et al., Methods in Enzymology (1989) 121, 663-666; and Bird, R. E. et al., TIBTECH (1991) 9, 132-137).

An scFv can be obtained by linking the H-chain V region and the L-chain V region of an antibody. In this scFv, the H-chain V region and the L-chain V region are linked via a linker, preferably via a peptide linker (Huston, J. S. et al., Proc. Natl. Acad. Sci. USA (1988) 85, 5879-5883). The V regions of the H and L chains in an scFv may be derived from any of the antibodies described above. Peptide linkers for linking the V regions include, for example, an arbitrary single chain peptide consisting of 12 to 19 amino acid residues.

A DNA encoding an scFv can be obtained by amplifying a DNA portion that encodes the desired amino acid sequence in template sequences with PCR using a primer pair which defines the termini of the portion, wherein a DNA encoding an H chain or an H-chain V region and a DNA encoding an L chain or an L-chain V region of the aforementioned antibodies are used as the templates, and then further amplifying the amplified DNA portion with a DNA that encodes a peptide linker portion and a primer pair that defines both ends of the linker so that it may be linked to each of the H and L chains.

Once an scFv-encoding DNA has been prepared, an expression vector comprising the DNA and a host transformed with the expression vector can be obtained according to conventional methods. In addition, an scFv can be obtained according to conventional methods by using the host.

Similar to the above, the antibody fragments can be produced by obtaining their genes, expressing them, and then using a host. An "antibody" as used herein encompasses such antibody fragments.

Antibodies bound to various molecules such as polyethylene glycol (PEG) may also be used as modified antibodies. An "antibody" as used herein encompasses such modified antibodies. These modified antibodies can be obtained by chemically modifying the obtained antibodies. Such methods are already established in the art.

Antibodies produced and expressed as above can be isolated from the inside or outside of the cells or from the hosts, and then purified to homogeneity. The antibodies for use in the present invention can be isolated and purified by affinity chromatography. Columns used for the affinity chromatography include protein A columns and protein G columns.

Carriers used for the protein A columns include HyperD, POROS, and Sepharose F.F. Other methods used for the isolation and/or purification of ordinary proteins may be used without limitation.

For example, the antibodies used for the present invention may be isolated and purified by appropriately selecting and combining chromatographies other than the above-described affinity chromatography, filtration, ultrafiltration, salting-out, dialysis, and such. Examples of chromatographies include ion-exchange chromatography, hydrophobic chromatography, and gel filtration. These chromatographies can be applied to high performance liquid chromatography (HPLC). Alternatively, reverse phase HPLC may be used.

The concentration of the antibodies obtained as above can be determined by absorbance measurement, ELISA, and such. Specifically, when using absorbance measurement, the concentration can be determined by appropriately diluting the antibody solution with PBS(−), measuring its absorbance at 280 nm, and calculating the concentration by using the conversion factor 1.35 OD/1 mg/ml. Alternatively, when using ELISA, the concentration can be determined as below. Specifically, 100 □l of goat anti-human IgG (TAG) diluted to 1 □g/ml with 0.1 M bicarbonate buffer (pH 9.6) is added to a 96-well plate (Nunc) and incubated overnight at 4° C. to immobilize the antibody. After blocking, 100 □l of an appropriately diluted antibody to be used in the present invention or an appropriately diluted sample comprising the antibody, or human IgG (CAPPEL) as a standard is added, and the plate is incubated for one hour at room temperature.

After washing, 100 □l of 5,000× diluted alkaline phosphatase-labeled anti-human IgG (BIO SOURCE) is added, and the plate is incubated for one hour at room temperature. After another wash, the substrate solution is added, the plate is incubated, and absorbance at 405 nm is measured using MICROPLATE READER Model 3550 (Bio-Rad) to calculate the concentration of the antibody of interest.

The IL-6 variants used in the present invention are substances that have binding activity to an IL-6 receptor and which do not transmit IL-6 biological activity. That is, the IL-6 variants compete with IL-6 for binding to an IL-6 receptor, but do not transmit IL-6 biological activity, and thus block IL-6-mediated signal transduction.

The IL-6 variants are produced by introducing mutation(s) by substituting amino acid residue(s) in the amino acid sequence of IL-6. Any IL-6 from which the IL-6 variant is derived can be used, but human IL-6 is preferred, considering antigenicity and such.

More specifically, the amino acid substitutions are performed by predicting the secondary structure of IL-6 from the IL-6 amino acid sequence using known molecular modeling programs such as WHATIF (Vriend et al., J. Mol. Graphics (1990) 8, 52-56), and further assessing the influence of the substituted amino acid residue(s) on the whole molecule. After determining the appropriate amino acid residue(s) to be substituted, mutation(s) are introduced by a commonly performed PCR method using a vector comprising a nucleotide sequence encoding a human IL-6 gene as a template to cause amino acid substitution(s), and the gene encoding the IL-6 variant is thereby obtained. If needed, this gene is inserted into an appropriate expression vector, and the IL-6 variant can be obtained according to the aforementioned methods for expression, production, and purification of recombinant antibodies.

Specific examples of the IL-6 variants are disclosed in Brakenhoff et al., J. Biol. Chem. (1994) 269, 86-93; Savino et al., EMBO J. (1994) 13, 1357-1367; WO 96-18648; and WO 96-17869.

Partial peptides of IL-6 or the IL-6 receptor to be used in the present invention are substances that have a binding activity to the IL-6 receptor or IL-6, respectively, and which do not transmit the IL-6 biological activities. That is, the partial peptides of IL-6 or the IL-6 receptor bind to and capture the IL-6 receptor or IL-6, and thereby specifically inhibit binding of IL-6 to the IL-6 receptor. As a result, the IL-6 biological activities are not transmitted, and thus, IL-6-mediated signal transduction is blocked.

Partial peptides of IL-6 or the IL-6 receptor are peptides that are composed of the whole amino acid sequence of the region of the IL-6 or IL-6 receptor amino acid sequence or a part thereof involved in the binding between IL-6 and the IL-6 receptor. Such peptides are usually composed of 10 to 80, preferably 20 to 50, more preferably 20 to 40 amino acid residues.

Partial peptides of IL-6 or the IL-6 receptor can be produced by specifying the region of the IL-6 or IL-6 receptor amino acid sequence involved in the binding between IL-6 and the IL-6 receptor, and applying generally known methods such as genetic engineering techniques and peptide synthesis methods to the whole amino acid sequence of the specified region or a portion thereof.

To prepare a partial peptide of IL-6 or an IL-6 receptor by genetic engineering methods, a DNA sequence encoding the desired peptide is inserted into an expression vector, and then the peptide can be obtained by applying the aforementioned methods for expressing, producing, and purifying recombinant antibodies.

To produce a partial peptide of IL-6 or an IL-6 receptor by peptide synthesis methods, generally used peptide synthesis methods such as solid phase synthesis methods and liquid phase synthesis methods may be used.

Specifically, the peptides can be synthesized according to the method described in "The sequel of Development of Pharmaceuticals (Zoku Iyakuhin no Kaihatsu), Vol. 14, Peptide Synthesis (ed. Haruaki Yajima, 1991, Hirokawa Shoten)". As a solid phase synthesis method, the following method and such can be employed: binding the amino acid corresponding to the C terminus of the peptide to be synthesized to a support that is insoluble in organic solvents, and then elongating the peptide strand by alternately repeating: the reaction of condensing amino acids whose α-amino groups and branch chain functional groups are protected with appropriate protecting groups, one at a time in a C terminus to N terminus direction; and the reaction of removing the protecting groups from the α-amino groups of the resin-bound amino acids or peptides. Solid-phase peptide synthesis is broadly classified into the Boc method and the Fmoc method, depending on the type of protecting groups used.

After synthesizing the peptide of interest as above, deprotection reaction and cleavage reaction of the peptide strand from the support are carried out. For the cleavage reaction of the peptide strand, hydrogen fluoride or trifluoromethane sulfonic acid is generally used for the Boc method, and TFA is generally used for the Fmoc method. In the Boc method, for example, the protected peptide-bound resin is treated with hydrogen fluoride in the presence of anisole. Then, the peptide is recovered by removing the protecting groups and cleaving the peptide from its support. By freeze-drying the recovered peptide, a crude peptide can be obtained. In the Fmoc method, the deprotection reaction and the cleavage reaction of the peptide strand from the support can be performed in TFA and such by operations similar to those described above.

The obtained crude peptides can be separated and purified by applying HPLC. Elution may be performed under optimum conditions using a water-acetonitrile solvent system, which is generally used for protein purification. The fractions corresponding to the peaks of the obtained chromatographic profile are collected and freeze-dried. Peptide fractions purified this way are identified by molecular weight analysis via mass spectrum analysis, amino acid composition analysis, amino acid sequence analysis, and such.

Specific examples of the partial peptides of IL-6 and the IL-6 receptor are disclosed in JP-A (Kokai) H02-188600, JP-A (Kokai) H07-324097, JP-A (Kokai) H08-311098, and U.S. Pat. No. 5,210,075.

The antibodies used in the present invention may be conjugate antibodies that are bound to various molecules such as polyethylene glycol (PEG), radioactive substances, and toxins. Such conjugate antibodies can be obtained by chemically modifying the obtained antibodies. Methods for antibody modification have been already established in this field. Accordingly, the term "antibody" as used herein encompasses such conjugate antibodies.

"Antibodies" of the present invention include those that have been post-translationally modified. Post-translational modifications include, but are not limited to, modification of a heavy-chain or light-chain N-terminal glutamine or glutamic acid into a pyroglutamic acid by pyroglutamylation.

Preferred examples of the "IL-6 receptor antibody" of the present invention include tocilizumab which is a humanized anti-IL-6 receptor IgG1 antibody, humanized anti-IL-6 receptor antibodies produced by modifying the constant and variable regions of tocilizumab, and antibodies that bind to the same epitope bound by tocilizumab.

Specific examples include an antibody containing the heavy chain variable region of SEQ ID NO: 1 (heavy chain variable region of tocilizumab) and the light chain variable region of SEQ ID NO: 2 (light chain variable region of tocilizumab), and an antibody containing the heavy chain variable region of SEQ ID NO: 5 (heavy chain variable region of SA237) and the light chain variable region of SEQ ID NO: 6 (light chain variable region of SA237).

More specifically, examples include an antibody containing the heavy chain of SEQ ID NO: 3 (heavy chain of tocilizumab) and the light chain of SEQ ID NO: 4 (light chain of tocilizumab), and an antibody containing the heavy chain of SEQ ID NO: 7 (heavy chain of SA237) and the light chain of SEQ ID NO: 8 (light chain of SA237).

Such antibodies can be obtained according to the methods described in WO2010/035769, WO2010/107108, WO2010/106812, and such. Specifically, antibodies can be produced using genetic recombination techniques known to those skilled in the art, based on the sequence of the above-mentioned IL-6 receptor antibody (see, for example, Borrebaeck C A K and Larrick J W, THERAPEUTIC MONOCLONAL ANTIBODIES, Published in the United Kingdom by MACMILLAN PUBLISHERS LTD, 1990). A recombinant antibody can be obtained by cloning a DNA encoding the antibody from a hybridoma or an antibody-producing cell such as an antibody-producing sensitized lymphocyte, inserting the DNA into an appropriate vector, and introducing the vector into a host (host cell) to produce the antibody.

Such antibodies can be isolated and purified using isolation and purification methods conventionally used for antibody purification, without limitation. For example, the antibodies can be isolated and purified by appropriately selecting and combining column chromatography, filtration, ultrafiltration, salting-out, solvent precipitation, solvent extraction, distillation, immunoprecipitation, SDS-polyacrylamide gel electrophoresis, isoelectric focusing, dialysis, recrystallization, and such.

I-07 An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. Specifically, an "antibody that binds to the same epitope" as a reference antibody refers to an antibody that blocks binding of the reference antibody to its antigen in a competition assay by 60% or more, by 70% or more, by 80% or more, or by 90% or more.

IIC03 In another aspect, competition assays may be used to identify an antibody that competes with tocilizumab for binding to IL-6 receptor. In certain embodiments, such a competing antibody binds to the same epitope (e.g., a linear or a conformational epitope) that is bound by tocilizumab. Detailed exemplary methods for mapping an epitope to which an antibody binds are provided in Morris (1996) "Epitope Mapping Protocols" in Methods in Molecular Biology vol. 66 (Humana Press, Totowa, NJ).

IIC04 In an exemplary competition assay, immobilized IL-6 receptor is incubated in a solution comprising a first labeled antibody that binds to IL-6 receptor (e.g., tocilizumab) and a second unlabeled antibody that is being tested for its ability to compete with the first antibody for binding to IL-6 receptor. The second antibody may be present in a hybridoma supernatant. As a control, immobilized IL-6 receptor is incubated in a solution comprising the first labeled antibody but not the second unlabeled antibody. After incubation under conditions permissive for binding of the first antibody to IL-6 receptor, excess unbound antibody is removed, and the amount of label associated with immobilized IL-6 receptor is measured. If the amount of label associated with immobilized IL-6 receptor is substantially reduced in the test sample relative to the control sample, then that indicates that the second antibody is competing with the first antibody for binding to IL-6 receptor. See

23

Harlow and Lane (1988) Antibodies: A Laboratory Manual ch. 14 (Cold Spring Harbor Laboratory, Cold Spring Harbor, NY).

Therapeutic agents of the present invention can be formulated to produce freeze-dried formulations or solution formulations by mixing, if necessary, with suitable pharmaceutically acceptable carriers, vehicles, and such. The suitable pharmaceutically acceptable carriers and vehicles include, for example, sterilized water, physiological saline, stabilizers, excipients, antioxidants (such as ascorbic acid), buffers (such as phosphate, citrate, histidine, and other organic acids), antiseptics, surfactants (such as PEG and Tween), chelating agents (such as EDTA), and binders. Other low-molecular-weight polypeptides, proteins such as serum albumin, gelatin, and immunoglobulins, amino acids such as glycine, glutamine, asparagine, glutamic acid, aspartic acid, methionine, arginine, and lysine, sugars and carbohydrates such as polysaccharides and monosaccharides, and sugar alcohols such as mannitol and sorbitol may also be contained. When preparing an aqueous solution for injection, physiological saline and isotonic solutions comprising glucose and other adjuvants such as D-sorbitol, D-mannose, D-mannitol, and sodium chloride may be used; and appropriate solubilizers such as alcohol (for example, ethanol), polyalcohols (such as propylene glycol and PEG), and nonionic surfactants (such as polysorbate 80, polysorbate 20, poloxamer 188, and HCO-50) may be used in combination. By mixing hyaluronidase into the formulation, a larger fluid volume can be administered subcutaneously (Expert Opin. Drug Deliv. 2007 July; 4(4): 427-40). Furthermore, syringes may be prefilled with the pharmaceutical composition of the present invention. Solution formulations can be prepared according to the method described in WO2011/090088.

If necessary, the therapeutic agents of the present invention may be encapsulated in microcapsules (e.g., those made of hydroxymethylcellulose, gelatin, and poly(methylmetacrylate)), or incorporated into colloidal drug delivery systems (e.g., liposomes, albumin microspheres, microemulsion, nanoparticles, and nanocapsules) (see, for example, "Remington's Pharmaceutical Science 16th edition", Oslo Ed. (1980)). Methods for preparing the pharmaceutical agents as controlled-release pharmaceutical agents are also known, and such methods may be applied to the therapeutic agents of the present invention (Langer et al., J. Biomed. Mater. Res. 15: 267-277 (1981); Langer, Chemtech. 12: 98-105 (1982); U.S. Pat. No. 3,773,919; European Patent Application Publication No. EP 58,481; Sidman et al., Biopolymers 22: 547-556 (1983); and EP 133,988).

The therapeutic agent of the present invention can be administered to a patient via any appropriate route. For example, it can be administered to a patient intravenously by bolus injection or by continuous infusion, intramuscularly, intraperitoneally, intracerebrospinally, transdermally, subcutaneously, intracutaneouly, intraarticularly, sublingually, intrasynovially, orally, by inhalation, locally, or externally, for a certain period of time.

The dose can be selected, for example, in the range of 0.0001 mg to 100 mg of active ingredient per kg body weight per dose. Alternatively, for example, when administering to a human patient, the active ingredient per patient may be selected in the range of 0.001 mg to 1000 mg per 1 kg body weight. Regarding an IL-6 inhibitor, the active ingredient of which is an antibody, the amount included in a single dose is preferably, for example, approximately 0.01 mg to 50 mg per kg body weight.

In the present invention, an IL-6 inhibitor may be administered by combining the IL-6 inhibitor with a known asthma treatment regimen. For example, the IL-6 inhibitor can be combined with systemic administration of a steroid or an inhaled steroid. Furthermore, long-acting β2-agonists, typically ICS-LABA and such, can also be combined. Known asthma treatment regimens include those described in Guidelines for Prevention and Control of Asthma, 2015; the ERS/ATS severe asthma guideline; the Japanese guideline (JGL); or the GINA guideline.

All prior art references cited herein are incorporated by reference into the present specification.

EXAMPLES

The subject was a 48-year old female patient with bronchial asthma which was difficult to control despite adding systemic steroid to inhaled steroid plus long-acting β2-agonist inhalation (ICS-LABA). After the administration of an anti-IL-6 receptor antibody (tocilizumab), which was administered against the accompanying chronic rheumatoid arthritis (RA), improvement of bronchial asthmatic symptoms was observed along with improvement of rheumatic symptoms. Temporal withdrawal of tocilizumab administration was found to exacerbate rheumatic symptoms as well as bronchial asthmatic symptoms, but resuming tocilizumab administration improved the bronchial asthmatic symptoms again. After tocilizumab administration, the dose of systemic steroid administration was reduced, and the number of inhalations of short-acting β2-agonists (SABA) also decreased remarkably.

The above-mentioned patient was a case which was difficult to control despite adding systemic steroid to high-dose inhaled steroid plus long-acting β2-agonist inhalation (ICS-LABA), therefore, is regarded as a severe asthma patient.

| (Case) 48-year old woman | |
|---|---|
| (Chief complaint) | coughing, wheezing |
| (Complications) | RA |
| | chronic hepatitis |
| (Past history) | anal fistula surgery |
| (Family history) | non-contributory |
| (Smoking history) | none |
| (Physical findings) | height: 156 cm |
| | body weight: 68 kg |
| | BMI: 27.9 |
| (Accompanying allergic disorder) | non-contributory |

The female patient was introduced to a pulmonary medicine clinic, since coughing and wheezing occurred when she was attending a local otorhinolaryngology clinic for chronic sinusitis. Upon chest auscultation, rhonchi and wheezing were heard in the total lung field during inspiration. The patient had no smoking history, and there were no abnormal findings in chest x-ray. Since paroxysmal dyspnea and coughing were frequently observed and positive findings were obtained from respiration function reversibility testing, the patient was diagnosed with bronchial asthma. The blood test (Table 1) found no eosinophilia, IgE value within normal limit, and negative RAST score in the measured range.

Initiation of administration of budesonide plus formoterol (four inhalations per day) did not improve bronchial asthmatic symptoms. Changing of the therapeutic agents to ciclesonide 800 μg plus tulobuterol tape 2 mg, in combination with oral steroid (prednisolone 5 mg) as needed basis, improved the symptoms only slightly, but did not eliminate unscheduled medical consultations and did not reduce the number of administration of SABA (short-acting β2-agonists).

In the following year, the patient consulted an orthopedic clinic for lasting wrist pain and diagnosed with RA, and tocilizumab administration at 162 mg by subcutaneous injection every two weeks was initiated (Administration of ciclesonide 800 μg plus tulobuterol tape 2 mg was being continued from the previous year). After eight weeks from administration of tocilizumab, improvement of bronchial asthmatic symptoms, improvement of respiratory function, and decrease in the number of SABA use were observed. Decrease in unscheduled medical consultation was also observed.

The year after next, due to improvement of RA symptoms, tocilizumab administration was withdrawn by the orthopedic surgeon. From the same time, bronchial asthmatic symptoms exacerbated, the number of SABA inhalations increased, administration of a systemic steroid (30 mg of prednisolone for three days, two or more times a month) became necessary from an unscheduled medical consultation, and respiratory function testing showed aggravation again (Table 2) (Administration of ciclesonide 800 μg plus tulobuterol tape 2 mg was being continued from the previous year). After withdrawal of tocilizumab, RA symptoms also exacerbated, and tocilizumab administration was resumed by the orthopedic surgeon. Promptly after the administration, bronchial asthmatic symptoms improved again, respiratory function testing results improved (Table 2), frequency of SABA use decreased, and systemic steroid administration became unnecessary. Furthermore, unscheduled medical consultations were eliminated. Currently, tocilizumab administration is being continued, RA became stable, and bronchial asthma also became stable by administration of ciclesonide 400 μg plus tulobuterol tape 2 mg.

Discussion

In this case, a regulated amount of tocilizumab was administered by the orthopedic surgeon, and although blood IL-6 concentrations were not measured, bronchial asthmatic symptoms improved promptly after tocilizumab administration, exacerbated upon withdrawal of the administration, and improved again upon resuming the administration, and thereafter, bronchial asthma continues to be well-controlled during continued tocilizumab administration. Accordingly, involvement of IL-6 in bronchial asthma is inferred for this patient.

Besides the above-mentioned case, therapeutic effects of tocilizumab were confirmed in two severe asthma patients. In these patients, the blood eosinophil concentrations were within the normal range, and they were confirmed to have non-eosinophilic asthma.

TABLE 1

| Clinical Test Data | |
| --- | --- |
| Urine | |
| Specific gravity | 1.014 |
| pH | 7 |
| Protein | (−) |
| Glucose | (−) |
| Ketones | (+−) |
| Occult blood reaction | (−) |

TABLE 1-continued

| Clinical Test Data | |
| --- | --- |
| Urobilinogen | (+−) |
| Bilirubin | (−) |
| Nitrite | (−) |
| White blood cells | (++) |

| Blood | Standard values |
| --- | --- |
| Neutrophils 28-72 | 69.2 (%) |
| Lymphocytes 18-58 | 19.9 (%) |
| Monocytes 0-12 | 5.9 (%) |
| Eosinophils 0-5 | 4.8 (%) |
| Basophils 0-2 | 0.2 (%) |
| AST 8-38 | 12 U/L |
| ALT 4-44 | 12 U/L |
| ALP 104-338 | 285 U/L |
| LDH 106-211 | 97 U/L |
| γ-GTP 16-73 | 25 U/L |
| CholinE 229-521 | 292 U/L |
| Tprot 6.7-8.3 | 7.2 g/dL |
| Albumin 3.9-4.9 | 3.3 g/dL |
| BUN 8.0-20 | 7 mg/dL |
| Creat 0.43-0.72 | 0.43 mg/dL |
| eGFR | 118.8 ml/min |
| UA 2.4-5.6 | 5.5 mg/dL |
| HDL-chol 40-105 | 50 mg/dL |
| Na 136-145 | 138 mEq/L |
| K 3.5-5 | 3.8 mEq/L |
| Cl 100-106 | 104 mEq/L |
| Ca 8.8-10.2 | 8.9 mg/dL |
| Glucose 70-110 | 90 mg/dL |
| Fe 43-172 | 63 μg/dL |
| Tbil 0.22-1.2 | 0.6 mg/dL |
| LDL-chol 70-139 | 84 mg/dL |
| CRP <0.3 | 3.27 mg/dL |
| IgE <173 | 68.4 IU/mL |
| Cradosporium | Class0 |
| Aspergillus | Class0 |
| Arterunalia | Class0 |
| Candida | Class0 |
| D1 | Class0 |
| D2 | Class0 |
| HD1 | Class0 |
| HD2 | Class0 |

TABLE 2

| Respiratory Function Test | | | | | |
| --- | --- | --- | --- | --- | --- |
| | | At the initial visit | After tocilizumab administration | Immediately after withdrawal of tocilizumab | After resuming tocilizumab |
| VC | L | 2.56 | 2.31 | 1.96 | 2.44 |
| % VC | % | 96.2 | 86.2 | 75.1 | 94.2 |
| IC | L | 1.55 | 1.91 | 1.56 | 2.07 |
| FVC | L | 2.56 | 2.31 | 1.92 | 2.44 |
| FEV1 | L | 1.63 | 1.68 | 0.82 | 1.5 |
| FEV1(%) | % | 63.7 | 72.7 | 42.7 | 61.5 |
| PEF | L/sec | 2.19 | 2.44 | 0.96 | 1.85 |
| % V25 | % | 14 | 30.2 | 10.9 | 18 |

VC (Vital Capacity): lung capacity
% VC (Percentage Vital Capacity): percentage lung capacity
IC (Inspiratory Capacity): maximum inspiratory capacity
FVC (Forced Vital Capacity): forced lung capacity
FEV1 (Forced Expiratory Volume in 1 second): volume in one second
FEV1(%) (Percentage FEV1.0 of FVC (%)): percentage in one second
PEF (Peak Expiratory Flow): maximum expiratory flow
% V25 (Percentage Forced Expiratory Flow at 75% of the FVC)

INDUSTRIAL APPLICABILITY

The therapeutic agents of the present invention provide new means for treating asthma.

The invention claimed is:

1. A method for treating human severe non-eosinophilic asthma, comprising administering 162 mg of an anti-IL-6 receptor antibody to a human adult subject in need thereof, wherein the anti-IL-6 receptor antibody is tocilizumab.

2. The method of claim 1, wherein tocilizumab comprises:
   a) the heavy chain variable region of SEQ ID NO: 1 and the light chain variable region of SEQ ID NO: 2; or
   b) the heavy chain variable region of SEQ ID NO: 5 and the light chain variable region of SEQ ID NO: 6.

3. The method of claim 1, wherein tocilizumab comprises:
   a) the heavy chain of SEQ ID NO: 3 and the light chain of SEQ ID NO: 4, or
   b) the heavy chain of SEQ ID NO: 7 and the light chain of SEQ ID NO: 8.

4. The method of claim 1, wherein the blood C-reactive protein (CRP) of the subject administered the anti-IL-6 receptor antibody is above normal level.

5. The method of claim 1, wherein the subject has rheumatoid arthritis.

6. The method of claim 1, wherein the administration results in:
   suppression of at least one asthmatic symptom in the subject selected from coughing, wheezing, expectoration, and dyspnea;
   a) improvement of respiratory function of the subject as measured by Peak Expiratory Flow (PEF); or
   b) reduction in the amount of steroid use by the subject.

7. The method of claim 1, wherein the administration results in an improved Asthma Control Test (ACT) score in the subject and wherein the improved ACT score is 20 or greater.

8. The method of claim 1, wherein the anti-IL-6 receptor antibody is administered in combination with an inhaled steroid or a systemic steroid.

9. The method of claim 1, wherein the anti-IL-6 receptor antibody is administered in combination with an additional long-acting β2-agonist.

* * * * *